US011149075B2

(12) United States Patent
Gieffers et al.

(10) Patent No.: US 11,149,075 B2

(45) **Date of Patent: *Oct. 19, 2021**

(54) SINGLE-CHAIN GLUCOCORTICOID-INDUCED TUMOR NECROSIS FACTOR RECEPTOR (GITR) RECEPTOR AGONIST PROTEINS

(71) Applicant: Apogenix AG, Heidelberg (DE)

(72) Inventors: Christian Gieffers, Dossenheim (DE); Oliver Hill, Neckarsteinach (DE); Meinolf Thiemann, Schriesheim (DE); Tim Schnyder, Igersheim (DE)

(73) Assignee: APOGENIX AG, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/732,854

(22) Filed: Jan. 2, 2020

(65) Prior Publication Data

US 2020/0123223 A1 Apr. 23, 2020

Related U.S. Application Data

(63) Continuation of application No. 15/957,279, filed on Apr. 19, 2018, now Pat. No. 10,533,043, which is a continuation of application No. PCT/EP2016/075552, filed on Oct. 24, 2016.

(60) Provisional application No. 62/245,815, filed on Oct. 23, 2015.

(51) Int. Cl.

| | |
|---|---|
| ***C07K 14/705*** | (2006.01) |
| ***C12N 15/00*** | (2006.01) |
| ***A61K 38/00*** | (2006.01) |

(52) U.S. Cl.

CPC ........ *C07K 14/70575* (2013.01); *C12N 15/00* (2013.01); *A61K 38/00* (2013.01); *C07K 2319/00* (2013.01); *C07K 2319/22* (2013.01); *C07K 2319/30* (2013.01); *C07K 2319/32* (2013.01); *C07K 2319/35* (2013.01); *C07K 2319/74* (2013.01)

(58) Field of Classification Search

CPC .......... C07K 14/70575; C07K 2319/00; C07K 2319/22; C07K 2319/30; C07K 2319/32; C07K 2319/35; C07K 2319/74; C12N 15/00; A61K 38/00; A61P 37/06; A61P 35/00; A61P 31/04; A61P 3/00; A61P 29/00; A61P 25/00; A61P 19/02

See application file for complete search history.

(56) References Cited

FOREIGN PATENT DOCUMENTS

| | | | | |
|---|---|---|---|---|
| CN | 102250250 | A | 11/2011 | |
| EP | 1746161 | A1 | 1/2007 | |
| JP | 2008-167678 | A | 7/2008 | |
| WO | 99/66054 | A2 | 12/1999 | |
| WO | 00/11033 | A2 | 3/2000 | |
| WO | 2005103077 | A1 | 11/2005 | |
| WO | 2009/007120 | A2 | 1/2009 | |
| WO | 2010010051 | A1 | 1/2010 | |
| WO | 2010/078966 | A1 | 7/2010 | |
| WO | 2013092983 | A2 | 6/2013 | |
| WO | WO-2015164588 | A1 * | 10/2015 | ............. A61P 25/00 |

OTHER PUBLICATIONS

Chattopadhyay, Kausik, et al. , "Assembly and structural properties of glucocorticoid-induced TNF receptor ligand: Implications for function", Proceedings of the National Academy of Sciences , 19452-19457, vol. 104, No. 49, US, (Dec. 4, 2007).

International Search Report and Written Opinion of the International Searching Authority dated Jan. 5, 2017 issued in PCT/EP2016/075552.

Suvas et al., "In Vivo Kinetics of GITR and GITR Ligand Expression and Their Functional Significance in Regulating Viral Immunopathology"; Journal of Virology, 2005, pp. 11935-11942.

* cited by examiner

*Primary Examiner* — Robert S Landsman

(74) *Attorney, Agent, or Firm* — Perkins Coie LLP; Viola T. Kung

(57) ABSTRACT

Provided herein are specific GITR receptor agonist proteins, nucleic acids encoding the same, and methods of treating a subject having a GITRL-associated disease or disorder. The GITR receptor agonist proteins provided herein comprise three soluble GITRL domains and an Fc fragment. The GITR receptor agonist proteins are substantially non-aggregating and suitable for therapeutic, diagnostic and/or research applications.

21 Claims, 8 Drawing Sheets

Specification includes a Sequence Listing.

| Lane | |
|---|---|
| 1 | Marker |
| 2 | Protein A, non reduced |
| 3 | Protein B, non reduced |
| 4 | Protein C, non reduced |
| 5 | Protein A, reduced |
| 6 | Protein B, reduced |
| 7 | Protein C, reduced |

SEQUENCE LISTING

```
<160> NUMBER OF SEQ ID NOS: 50

<210> SEQ ID NO 1
<211> LENGTH: 177
<212> TYPE: PRT
<213> ORGANISM: Homo sapiens
<220> FEATURE:
<223> OTHER INFORMATION: GITR Ligand WT

<400> SEQUENCE: 1

Met Cys Leu Ser His Leu Glu Asn Met Pro Leu Ser His Ser Arg Thr
1               5                   10                  15

Gln Gly Ala Gln Arg Ser Ser Trp Lys Leu Trp Leu Phe Cys Ser Ile
            20                  25                  30

Val Met Leu Leu Phe Leu Cys Ser Phe Ser Trp Leu Ile Phe Ile Phe
        35                  40                  45

Leu Gln Leu Glu Thr Ala Lys Glu Pro Cys Met Ala Lys Phe Gly Pro
    50                  55                  60

Leu Pro Ser Lys Trp Gln Met Ala Ser Ser Glu Pro Pro Cys Val Asn
65                  70                  75                  80

Lys Val Ser Asp Trp Lys Leu Glu Ile Leu Gln Asn Gly Leu Tyr Leu
                85                  90                  95

Ile Tyr Gly Gln Val Ala Pro Asn Ala Asn Tyr Asn Asp Val Ala Pro
            100                 105                 110

Phe Glu Val Arg Leu Tyr Lys Asn Lys Asp Met Ile Gln Thr Leu Thr
        115                 120                 125

Asn Lys Ser Lys Ile Gln Asn Val Gly Gly Thr Tyr Glu Leu His Val
    130                 135                 140

Gly Asp Thr Ile Asp Leu Ile Phe Asn Ser Glu His Gln Val Leu Lys
145                 150                 155                 160

Asn Asn Thr Tyr Trp Gly Ile Ile Leu Leu Ala Asn Pro Gln Phe Ile
                165                 170                 175

Ser


<210> SEQ ID NO 2
<211> LENGTH: 8
<212> TYPE: PRT
<213> ORGANISM: Artificial Sequence
<220> FEATURE:
<223> OTHER INFORMATION: linker

<400> SEQUENCE: 2

Gly Ser Gly Ser Gly Asn Gly Ser
1               5


<210> SEQ ID NO 3
<211> LENGTH: 8
<212> TYPE: PRT
<213> ORGANISM: Artificial Sequence
<220> FEATURE:
<223> OTHER INFORMATION: linker
```

-continued

<400> SEQUENCE: 3

Gly Ser Gly Ser Gly Ser Gly Ser
1 5

<210> SEQ ID NO 4
<211> LENGTH: 8
<212> TYPE: PRT
<213> ORGANISM: Artificial Sequence
<220> FEATURE:
<223> OTHER INFORMATION: linker

<400> SEQUENCE: 4

Gly Gly Ser Gly Ser Gly Ser Gly
1 5

<210> SEQ ID NO 5
<211> LENGTH: 6
<212> TYPE: PRT
<213> ORGANISM: Artificial Sequence
<220> FEATURE:
<223> OTHER INFORMATION: linker

<400> SEQUENCE: 5

Gly Gly Ser Gly Ser Gly
1 5

<210> SEQ ID NO 6
<211> LENGTH: 4
<212> TYPE: PRT
<213> ORGANISM: Artificial Sequence
<220> FEATURE:
<223> OTHER INFORMATION: linker

<400> SEQUENCE: 6

Gly Gly Ser Gly
1

<210> SEQ ID NO 7
<211> LENGTH: 8
<212> TYPE: PRT
<213> ORGANISM: Artificial Sequence
<220> FEATURE:
<223> OTHER INFORMATION: linker

<400> SEQUENCE: 7

Gly Gly Ser Gly Asn Gly Ser Gly
1 5

<210> SEQ ID NO 8
<211> LENGTH: 8
<212> TYPE: PRT
<213> ORGANISM: Artificial Sequence
<220> FEATURE:
<223> OTHER INFORMATION: linker

<400> SEQUENCE: 8

Gly Gly Asn Gly Ser Gly Ser Gly
1 5

<210> SEQ ID NO 9
<211> LENGTH: 6
<212> TYPE: PRT
<213> ORGANISM: Artificial Sequence
<220> FEATURE:
<223> OTHER INFORMATION: linker

<400> SEQUENCE: 9

Gly Gly Asn Gly Ser Gly
1 5

<210> SEQ ID NO 10
<211> LENGTH: 6
<212> TYPE: PRT
<213> ORGANISM: Artificial Sequence
<220> FEATURE:
<223> OTHER INFORMATION: linker

<400> SEQUENCE: 10

Gly Ser Gly Ser Gly Ser
1 5

<210> SEQ ID NO 11
<211> LENGTH: 4
<212> TYPE: PRT
<213> ORGANISM: Artificial Sequence
<220> FEATURE:
<223> OTHER INFORMATION: linker

<400> SEQUENCE: 11

Gly Ser Gly Ser
1

<210> SEQ ID NO 12
<211> LENGTH: 3
<212> TYPE: PRT
<213> ORGANISM: Artificial Sequence
<220> FEATURE:
<223> OTHER INFORMATION: linker

<400> SEQUENCE: 12

Gly Ser Gly
1

<210> SEQ ID NO 13
<211> LENGTH: 218
<212> TYPE: PRT
<213> ORGANISM: Artificial Sequence
<220> FEATURE:
<223> OTHER INFORMATION: IGG1-Fc N297S

<400> SEQUENCE: 13

Pro Ala Pro Glu Leu Leu Gly Gly Pro Ser Val Phe Leu Phe Pro Pro
1 5 10 15

Lys Pro Lys Asp Thr Leu Met Ile Ser Arg Thr Pro Glu Val Thr Cys
20 25 30

Val Val Val Asp Val Ser His Glu Asp Pro Glu Val Lys Phe Asn Trp
35 40 45

Tyr Val Asp Gly Val Glu Val His Asn Ala Lys Thr Lys Pro Arg Glu
50 55 60

Glu Gln Tyr Ser Ser Thr Tyr Arg Val Val Ser Val Leu Thr Val Leu
65 70 75 80

His Gln Asp Trp Leu Asn Gly Lys Glu Tyr Lys Cys Lys Val Ser Asn
85 90 95

Lys Ala Leu Pro Ala Pro Ile Glu Lys Thr Ile Ser Lys Ala Lys Gly
100 105 110

Gln Pro Arg Glu Pro Gln Val Tyr Thr Leu Pro Pro Ser Arg Glu Glu
115 120 125

Met Thr Lys Asn Gln Val Ser Leu Thr Cys Leu Val Lys Gly Phe Tyr
130 135 140

-continued

Pro Ser Asp Ile Ala Val Glu Trp Glu Ser Asn Gly Gln Pro Glu Asn
145 150 155 160

Asn Tyr Lys Thr Thr Pro Pro Val Leu Asp Ser Asp Gly Ser Phe Phe
165 170 175

Leu Tyr Ser Lys Leu Thr Val Asp Lys Ser Arg Trp Gln Gln Gly Asn
180 185 190

Val Phe Ser Cys Ser Val Met His Glu Ala Leu His Asn His Tyr Thr
195 200 205

Gln Lys Ser Leu Ser Leu Ser Pro Gly Lys
210 215

<210> SEQ ID NO 14
<211> LENGTH: 217
<212> TYPE: PRT
<213> ORGANISM: Artificial Sequence
<220> FEATURE:
<223> OTHER INFORMATION: IGG1-Fc WT

<400> SEQUENCE: 14

Pro Ala Pro Pro Val Ala Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Gly Leu Pro Ser Ser Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Thr Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys
210 215

<210> SEQ ID NO 15
<211> LENGTH: 667
<212> TYPE: PRT
<213> ORGANISM: Artificial Sequence
<220> FEATURE:
<223> OTHER INFORMATION: PROT A (GITRL Deglyco Fc)

<400> SEQUENCE: 15

Met Glu Thr Asp Thr Leu Leu Val Phe Val Leu Leu Val Trp Val Pro

-continued

```
1               5                   10                  15

Ala Gly Asn Gly Glu Thr Ala Lys Glu Pro Cys Met Ala Lys Phe Gly
            20                  25                  30

Pro Leu Pro Ser Lys Trp Gln Met Ala Ser Ser Glu Pro Pro Cys Val
        35                  40                  45

Asn Lys Val Ser Asp Trp Lys Leu Glu Ile Leu Gln Asn Gly Leu Tyr
    50                  55                  60

Leu Ile Tyr Gly Gln Val Ala Pro Asn Ala Asn Tyr Asn Asp Val Ala
65                  70                  75                  80

Pro Phe Glu Val Arg Leu Tyr Lys Asn Lys Asp Met Ile Gln Thr Leu
                85                  90                  95

Thr Asn Lys Ser Lys Ile Gln Asn Val Gly Gly Thr Tyr Glu Leu His
            100                 105                 110

Val Gly Asp Thr Ile Asp Leu Ile Phe Asn Ser Glu His Gln Val Leu
        115                 120                 125

Lys Asn Asn Thr Tyr Trp Gly Ile Ile Leu Leu Ala Asn Pro Gln Phe
    130                 135                 140

Ile Ser Gly Ser Gly Ser Gly Asn Gly Ser Glu Thr Ala Lys Glu Pro
145                 150                 155                 160

Cys Met Ala Lys Phe Gly Pro Leu Pro Ser Lys Trp Gln Met Ala Ser
                165                 170                 175

Ser Glu Pro Pro Cys Val Asn Lys Val Ser Asp Trp Lys Leu Glu Ile
            180                 185                 190

Leu Gln Asn Gly Leu Tyr Leu Ile Tyr Gly Gln Val Ala Pro Asn Ala
        195                 200                 205

Asn Tyr Asn Asp Val Ala Pro Phe Glu Val Arg Leu Tyr Lys Asn Lys
    210                 215                 220

Asp Met Ile Gln Thr Leu Thr Asn Lys Ser Lys Ile Gln Asn Val Gly
225                 230                 235                 240

Gly Thr Tyr Glu Leu His Val Gly Asp Thr Ile Asp Leu Ile Phe Asn
                245                 250                 255

Ser Glu His Gln Val Leu Lys Asn Asn Thr Tyr Trp Gly Ile Ile Leu
            260                 265                 270

Leu Ala Asn Pro Gln Phe Ile Ser Gly Ser Gly Ser Gly Asn Gly Ser
        275                 280                 285

Glu Thr Ala Lys Glu Pro Cys Met Ala Lys Phe Gly Pro Leu Pro Ser
    290                 295                 300

Lys Trp Gln Met Ala Ser Ser Glu Pro Pro Cys Val Asn Lys Val Ser
305                 310                 315                 320

Asp Trp Lys Leu Glu Ile Leu Gln Asn Gly Leu Tyr Leu Ile Tyr Gly
                325                 330                 335

Gln Val Ala Pro Asn Ala Asn Tyr Asn Asp Val Ala Pro Phe Glu Val
            340                 345                 350

Arg Leu Tyr Lys Asn Lys Asp Met Ile Gln Thr Leu Thr Asn Lys Ser
        355                 360                 365

Lys Ile Gln Asn Val Gly Gly Thr Tyr Glu Leu His Val Gly Asp Thr
    370                 375                 380

Ile Asp Leu Ile Phe Asn Ser Glu His Gln Val Leu Lys Asn Asn Thr
385                 390                 395                 400

Tyr Trp Gly Ile Ile Leu Leu Ala Asn Pro Gln Phe Ile Ser Gly Ser
                405                 410                 415

Ser Ser Ser Ser Ser Ser Ser Gly Ser Cys Asp Lys Thr His Thr Cys
            420                 425                 430
```

```
Pro Pro Cys Pro Ala Pro Glu Leu Leu Gly Gly Pro Ser Val Phe Leu
        435                 440                 445

Phe Pro Pro Lys Pro Lys Asp Thr Leu Met Ile Ser Arg Thr Pro Glu
    450                 455                 460

Val Thr Cys Val Val Val Asp Val Ser His Glu Asp Pro Glu Val Lys
465                 470                 475                 480

Phe Asn Trp Tyr Val Asp Gly Val Glu Val His Asn Ala Lys Thr Lys
                485                 490                 495

Pro Arg Glu Glu Gln Tyr Ser Ser Thr Tyr Arg Val Val Ser Val Leu
            500                 505                 510

Thr Val Leu His Gln Asp Trp Leu Asn Gly Lys Glu Tyr Lys Cys Lys
        515                 520                 525

Val Ser Asn Lys Ala Leu Pro Ala Pro Ile Glu Lys Thr Ile Ser Lys
    530                 535                 540

Ala Lys Gly Gln Pro Arg Glu Pro Gln Val Tyr Thr Leu Pro Pro Ser
545                 550                 555                 560

Arg Glu Glu Met Thr Lys Asn Gln Val Ser Leu Thr Cys Leu Val Lys
                565                 570                 575

Gly Phe Tyr Pro Ser Asp Ile Ala Val Glu Trp Glu Ser Asn Gly Gln
            580                 585                 590

Pro Glu Asn Asn Tyr Lys Thr Thr Pro Pro Val Leu Asp Ser Asp Gly
        595                 600                 605

Ser Phe Phe Leu Tyr Ser Lys Leu Thr Val Asp Lys Ser Arg Trp Gln
    610                 615                 620

Gln Gly Asn Val Phe Ser Cys Ser Val Met His Glu Ala Leu His Asn
625                 630                 635                 640

His Tyr Thr Gln Lys Ser Leu Ser Leu Ser Pro Gly Ser Ser Ser Ser
                645                 650                 655

Ser Ser Ala Trp Ser His Pro Gln Phe Glu Lys
            660                 665


<210> SEQ ID NO 16
<211> LENGTH: 21
<212> TYPE: PRT
<213> ORGANISM: Artificial Sequence
<220> FEATURE:
<223> OTHER INFORMATION: hinge linker

<400> SEQUENCE: 16

Gly Ser Ser Ser Ser Ser Ser Ser Ser Gly Ser Cys Asp Lys Thr His
1               5                   10                  15

Thr Cys Pro Pro Cys
            20


<210> SEQ ID NO 17
<211> LENGTH: 20
<212> TYPE: PRT
<213> ORGANISM: Artificial Sequence
<220> FEATURE:
<223> OTHER INFORMATION: universal signal peptide

<400> SEQUENCE: 17

Met Glu Thr Asp Thr Leu Leu Val Phe Val Leu Leu Val Trp Val Pro
1               5                   10                  15

Ala Gly Asn Gly
            20
```

```
<210> SEQ ID NO 18
<211> LENGTH: 15
<212> TYPE: PRT
<213> ORGANISM: Artificial Sequence
<220> FEATURE:
<223> OTHER INFORMATION: serine linker with strep tag

<400> SEQUENCE: 18

Ser Ser Ser Ser Ser Ser Ala Trp Ser His Pro Gln Phe Glu Lys
1               5                   10                  15


<210> SEQ ID NO 19
<211> LENGTH: 20
<212> TYPE: PRT
<213> ORGANISM: Artificial Sequence
<220> FEATURE:
<223> OTHER INFORMATION: hinge linker

<400> SEQUENCE: 19

Gly Ser Ser Ser Ser Ser Ser Ser Gly Ser Cys Asp Lys Thr His Thr
1               5                   10                  15

Cys Pro Pro Cys
            20


<210> SEQ ID NO 20
<211> LENGTH: 19
<212> TYPE: PRT
<213> ORGANISM: Artificial Sequence
<220> FEATURE:
<223> OTHER INFORMATION: hinge linker

<400> SEQUENCE: 20

Gly Ser Ser Ser Ser Ser Ser Gly Ser Cys Asp Lys Thr His Thr Cys
1               5                   10                  15

Pro Pro Cys


<210> SEQ ID NO 21
<211> LENGTH: 18
<212> TYPE: PRT
<213> ORGANISM: Artificial Sequence
<220> FEATURE:
<223> OTHER INFORMATION: hinge linker

<400> SEQUENCE: 21

Gly Ser Ser Ser Ser Ser Gly Ser Cys Asp Lys Thr His Thr Cys Pro
1               5                   10                  15

Pro Cys


<210> SEQ ID NO 22
<211> LENGTH: 16
<212> TYPE: PRT
<213> ORGANISM: Artificial Sequence
<220> FEATURE:
<223> OTHER INFORMATION: hinge linker

<400> SEQUENCE: 22

Gly Ser Ser Ser Gly Ser Cys Asp Lys Thr His Thr Cys Pro Pro Cys
1               5                   10                  15


<210> SEQ ID NO 23
<211> LENGTH: 18
<212> TYPE: PRT
<213> ORGANISM: Artificial Sequence
<220> FEATURE:
<223> OTHER INFORMATION: hinge linker
```

<400> SEQUENCE: 23

Gly Ser Ser Ser Gly Ser Cys Asp Lys Thr His Thr Cys Pro Pro Cys
1               5                   10                  15

Gly Ser

<210> SEQ ID NO 24
<211> LENGTH: 20
<212> TYPE: PRT
<213> ORGANISM: Artificial Sequence
<220> FEATURE:
<223> OTHER INFORMATION: hinge linker

<400> SEQUENCE: 24

Gly Ser Ser Ser Gly Ser Cys Asp Lys Thr His Thr Cys Pro Pro Cys
1               5                   10                  15

Gly Ser Gly Ser
            20

<210> SEQ ID NO 25
<211> LENGTH: 653
<212> TYPE: PRT
<213> ORGANISM: Artificial Sequence
<220> FEATURE:
<223> OTHER INFORMATION: PROTEIN A - no strep tag

<400> SEQUENCE: 25

Met Glu Thr Asp Thr Leu Leu Val Phe Val Leu Leu Val Trp Val Pro
1               5                   10                  15

Ala Gly Asn Gly Glu Thr Ala Lys Glu Pro Cys Met Ala Lys Phe Gly
            20                  25                  30

Pro Leu Pro Ser Lys Trp Gln Met Ala Ser Ser Glu Pro Pro Cys Val
        35                  40                  45

Asn Lys Val Ser Asp Trp Lys Leu Glu Ile Leu Gln Asn Gly Leu Tyr
    50                  55                  60

Leu Ile Tyr Gly Gln Val Ala Pro Asn Ala Asn Tyr Asn Asp Val Ala
65                  70                  75                  80

Pro Phe Glu Val Arg Leu Tyr Lys Asn Lys Asp Met Ile Gln Thr Leu
                85                  90                  95

Thr Asn Lys Ser Lys Ile Gln Asn Val Gly Gly Thr Tyr Glu Leu His
            100                 105                 110

Val Gly Asp Thr Ile Asp Leu Ile Phe Asn Ser Glu His Gln Val Leu
        115                 120                 125

Lys Asn Asn Thr Tyr Trp Gly Ile Ile Leu Leu Ala Asn Pro Gln Phe
    130                 135                 140

Ile Ser Gly Ser Gly Ser Gly Asn Gly Ser Glu Thr Ala Lys Glu Pro
145                 150                 155                 160

Cys Met Ala Lys Phe Gly Pro Leu Pro Ser Lys Trp Gln Met Ala Ser
                165                 170                 175

Ser Glu Pro Pro Cys Val Asn Lys Val Ser Asp Trp Lys Leu Glu Ile
            180                 185                 190

Leu Gln Asn Gly Leu Tyr Leu Ile Tyr Gly Gln Val Ala Pro Asn Ala
        195                 200                 205

Asn Tyr Asn Asp Val Ala Pro Phe Glu Val Arg Leu Tyr Lys Asn Lys
    210                 215                 220

Asp Met Ile Gln Thr Leu Thr Asn Lys Ser Lys Ile Gln Asn Val Gly
225                 230                 235                 240

Gly Thr Tyr Glu Leu His Val Gly Asp Thr Ile Asp Leu Ile Phe Asn

-continued

```
                245                 250                 255

Ser Glu His Gln Val Leu Lys Asn Asn Thr Tyr Trp Gly Ile Ile Leu
            260                 265                 270

Leu Ala Asn Pro Gln Phe Ile Ser Gly Ser Gly Ser Gly Asn Gly Ser
        275                 280                 285

Glu Thr Ala Lys Glu Pro Cys Met Ala Lys Phe Gly Pro Leu Pro Ser
    290                 295                 300

Lys Trp Gln Met Ala Ser Ser Glu Pro Pro Cys Val Asn Lys Val Ser
305                 310                 315                 320

Asp Trp Lys Leu Glu Ile Leu Gln Asn Gly Leu Tyr Leu Ile Tyr Gly
                325                 330                 335

Gln Val Ala Pro Asn Ala Asn Tyr Asn Asp Val Ala Pro Phe Glu Val
            340                 345                 350

Arg Leu Tyr Lys Asn Lys Asp Met Ile Gln Thr Leu Thr Asn Lys Ser
        355                 360                 365

Lys Ile Gln Asn Val Gly Gly Thr Tyr Glu Leu His Val Gly Asp Thr
    370                 375                 380

Ile Asp Leu Ile Phe Asn Ser Glu His Gln Val Leu Lys Asn Asn Thr
385                 390                 395                 400

Tyr Trp Gly Ile Ile Leu Leu Ala Asn Pro Gln Phe Ile Ser Gly Ser
                405                 410                 415

Ser Ser Ser Ser Ser Ser Ser Gly Ser Cys Asp Lys Thr His Thr Cys
            420                 425                 430

Pro Pro Cys Pro Ala Pro Glu Leu Leu Gly Gly Pro Ser Val Phe Leu
        435                 440                 445

Phe Pro Pro Lys Pro Lys Asp Thr Leu Met Ile Ser Arg Thr Pro Glu
    450                 455                 460

Val Thr Cys Val Val Val Asp Val Ser His Glu Asp Pro Glu Val Lys
465                 470                 475                 480

Phe Asn Trp Tyr Val Asp Gly Val Glu Val His Asn Ala Lys Thr Lys
                485                 490                 495

Pro Arg Glu Glu Gln Tyr Ser Ser Thr Tyr Arg Val Val Ser Val Leu
            500                 505                 510

Thr Val Leu His Gln Asp Trp Leu Asn Gly Lys Glu Tyr Lys Cys Lys
        515                 520                 525

Val Ser Asn Lys Ala Leu Pro Ala Pro Ile Glu Lys Thr Ile Ser Lys
    530                 535                 540

Ala Lys Gly Gln Pro Arg Glu Pro Gln Val Tyr Thr Leu Pro Pro Ser
545                 550                 555                 560

Arg Glu Glu Met Thr Lys Asn Gln Val Ser Leu Thr Cys Leu Val Lys
                565                 570                 575

Gly Phe Tyr Pro Ser Asp Ile Ala Val Glu Trp Glu Ser Asn Gly Gln
            580                 585                 590

Pro Glu Asn Asn Tyr Lys Thr Thr Pro Pro Val Leu Asp Ser Asp Gly
        595                 600                 605

Ser Phe Phe Leu Tyr Ser Lys Leu Thr Val Asp Lys Ser Arg Trp Gln
    610                 615                 620

Gln Gly Asn Val Phe Ser Cys Ser Val Met His Glu Ala Leu His Asn
625                 630                 635                 640

His Tyr Thr Gln Lys Ser Leu Ser Leu Ser Pro Gly Lys
                645                 650
```

<210> SEQ ID NO 26

-continued

<211> LENGTH: 652
<212> TYPE: PRT
<213> ORGANISM: Artificial Sequence
<220> FEATURE:
<223> OTHER INFORMATION: GITRL-wt fused to Seq_14

<400> SEQUENCE: 26

Met Glu Thr Asp Thr Leu Leu Val Phe Val Leu Leu Val Trp Val Pro
1 5 10 15

Ala Gly Asn Gly Glu Thr Ala Lys Glu Pro Cys Met Ala Lys Phe Gly
20 25 30

Pro Leu Pro Ser Lys Trp Gln Met Ala Ser Ser Glu Pro Pro Cys Val
35 40 45

Asn Lys Val Ser Asp Trp Lys Leu Glu Ile Leu Gln Asn Gly Leu Tyr
50 55 60

Leu Ile Tyr Gly Gln Val Ala Pro Asn Ala Asn Tyr Asn Asp Val Ala
65 70 75 80

Pro Phe Glu Val Arg Leu Tyr Lys Asn Lys Asp Met Ile Gln Thr Leu
85 90 95

Thr Asn Lys Ser Lys Ile Gln Asn Val Gly Gly Thr Tyr Glu Leu His
100 105 110

Val Gly Asp Thr Ile Asp Leu Ile Phe Asn Ser Glu His Gln Val Leu
115 120 125

Lys Asn Asn Thr Tyr Trp Gly Ile Ile Leu Leu Ala Asn Pro Gln Phe
130 135 140

Ile Ser Gly Ser Gly Ser Gly Asn Gly Ser Glu Thr Ala Lys Glu Pro
145 150 155 160

Cys Met Ala Lys Phe Gly Pro Leu Pro Ser Lys Trp Gln Met Ala Ser
165 170 175

Ser Glu Pro Pro Cys Val Asn Lys Val Ser Asp Trp Lys Leu Glu Ile
180 185 190

Leu Gln Asn Gly Leu Tyr Leu Ile Tyr Gly Gln Val Ala Pro Asn Ala
195 200 205

Asn Tyr Asn Asp Val Ala Pro Phe Glu Val Arg Leu Tyr Lys Asn Lys
210 215 220

Asp Met Ile Gln Thr Leu Thr Asn Lys Ser Lys Ile Gln Asn Val Gly
225 230 235 240

Gly Thr Tyr Glu Leu His Val Gly Asp Thr Ile Asp Leu Ile Phe Asn
245 250 255

Ser Glu His Gln Val Leu Lys Asn Asn Thr Tyr Trp Gly Ile Ile Leu
260 265 270

Leu Ala Asn Pro Gln Phe Ile Ser Gly Ser Gly Ser Gly Asn Gly Ser
275 280 285

Glu Thr Ala Lys Glu Pro Cys Met Ala Lys Phe Gly Pro Leu Pro Ser
290 295 300

Lys Trp Gln Met Ala Ser Ser Glu Pro Pro Cys Val Asn Lys Val Ser
305 310 315 320

Asp Trp Lys Leu Glu Ile Leu Gln Asn Gly Leu Tyr Leu Ile Tyr Gly
325 330 335

Gln Val Ala Pro Asn Ala Asn Tyr Asn Asp Val Ala Pro Phe Glu Val
340 345 350

Arg Leu Tyr Lys Asn Lys Asp Met Ile Gln Thr Leu Thr Asn Lys Ser
355 360 365

Lys Ile Gln Asn Val Gly Gly Thr Tyr Glu Leu His Val Gly Asp Thr
370 375 380

```
Ile Asp Leu Ile Phe Asn Ser Glu His Gln Val Leu Lys Asn Asn Thr
385                 390                 395                 400

Tyr Trp Gly Ile Ile Leu Leu Ala Asn Pro Gln Phe Ile Ser Gly Ser
                405                 410                 415

Ser Ser Ser Ser Ser Ser Ser Gly Ser Cys Asp Lys Thr His Thr Cys
            420                 425                 430

Pro Pro Cys Pro Ala Pro Pro Val Ala Gly Pro Ser Val Phe Leu Phe
        435                 440                 445

Pro Pro Lys Pro Lys Asp Thr Leu Met Ile Ser Arg Thr Pro Glu Val
    450                 455                 460

Thr Cys Val Val Val Asp Val Ser His Glu Asp Pro Glu Val Lys Phe
465                 470                 475                 480

Asn Trp Tyr Val Asp Gly Val Glu Val His Asn Ala Lys Thr Lys Pro
                485                 490                 495

Arg Glu Glu Gln Tyr Asn Ser Thr Tyr Arg Val Val Ser Val Leu Thr
            500                 505                 510

Val Leu His Gln Asp Trp Leu Asn Gly Lys Glu Tyr Lys Cys Lys Val
        515                 520                 525

Ser Asn Lys Gly Leu Pro Ser Ser Ile Glu Lys Thr Ile Ser Lys Ala
    530                 535                 540

Lys Gly Gln Pro Arg Glu Pro Gln Val Tyr Thr Leu Pro Pro Ser Arg
545                 550                 555                 560

Glu Glu Met Thr Lys Asn Gln Val Ser Leu Thr Cys Leu Val Lys Gly
                565                 570                 575

Phe Tyr Pro Ser Asp Ile Ala Val Glu Trp Glu Ser Asn Gly Gln Pro
            580                 585                 590

Glu Asn Asn Tyr Lys Thr Thr Pro Pro Val Leu Asp Ser Asp Gly Ser
        595                 600                 605

Phe Phe Leu Tyr Ser Lys Leu Thr Val Asp Lys Ser Arg Trp Gln Gln
    610                 615                 620

Gly Asn Val Phe Ser Cys Ser Val Met His Glu Ala Leu His Asn His
625                 630                 635                 640

Tyr Thr Gln Lys Ser Leu Ser Leu Ser Pro Gly Lys
                645                 650


<210> SEQ ID NO 27
<211> LENGTH: 633
<212> TYPE: PRT
<213> ORGANISM: Artificial Sequence
<220> FEATURE:
<223> OTHER INFORMATION: GITRL-wt fused to Seq_13 (no sig, no strep tag,
      no glyco)

<400> SEQUENCE: 27

Glu Thr Ala Lys Glu Pro Cys Met Ala Lys Phe Gly Pro Leu Pro Ser
1               5                   10                  15

Lys Trp Gln Met Ala Ser Ser Glu Pro Pro Cys Val Asn Lys Val Ser
            20                  25                  30

Asp Trp Lys Leu Glu Ile Leu Gln Asn Gly Leu Tyr Leu Ile Tyr Gly
        35                  40                  45

Gln Val Ala Pro Asn Ala Asn Tyr Asn Asp Val Ala Pro Phe Glu Val
    50                  55                  60

Arg Leu Tyr Lys Asn Lys Asp Met Ile Gln Thr Leu Thr Asn Lys Ser
65                  70                  75                  80

Lys Ile Gln Asn Val Gly Gly Thr Tyr Glu Leu His Val Gly Asp Thr
```

-continued

```
                85                  90                  95

Ile Asp Leu Ile Phe Asn Ser Glu His Gln Val Leu Lys Asn Asn Thr
            100                 105                 110

Tyr Trp Gly Ile Ile Leu Leu Ala Asn Pro Gln Phe Ile Ser Gly Ser
        115                 120                 125

Gly Ser Gly Asn Gly Ser Glu Thr Ala Lys Glu Pro Cys Met Ala Lys
    130                 135                 140

Phe Gly Pro Leu Pro Ser Lys Trp Gln Met Ala Ser Ser Glu Pro Pro
145                 150                 155                 160

Cys Val Asn Lys Val Ser Asp Trp Lys Leu Glu Ile Leu Gln Asn Gly
                165                 170                 175

Leu Tyr Leu Ile Tyr Gly Gln Val Ala Pro Asn Ala Asn Tyr Asn Asp
            180                 185                 190

Val Ala Pro Phe Glu Val Arg Leu Tyr Lys Asn Lys Asp Met Ile Gln
        195                 200                 205

Thr Leu Thr Asn Lys Ser Lys Ile Gln Asn Val Gly Gly Thr Tyr Glu
    210                 215                 220

Leu His Val Gly Asp Thr Ile Asp Leu Ile Phe Asn Ser Glu His Gln
225                 230                 235                 240

Val Leu Lys Asn Asn Thr Tyr Trp Gly Ile Ile Leu Leu Ala Asn Pro
                245                 250                 255

Gln Phe Ile Ser Gly Ser Gly Ser Gly Asn Gly Ser Glu Thr Ala Lys
            260                 265                 270

Glu Pro Cys Met Ala Lys Phe Gly Pro Leu Pro Ser Lys Trp Gln Met
        275                 280                 285

Ala Ser Ser Glu Pro Pro Cys Val Asn Lys Val Ser Asp Trp Lys Leu
    290                 295                 300

Glu Ile Leu Gln Asn Gly Leu Tyr Leu Ile Tyr Gly Gln Val Ala Pro
305                 310                 315                 320

Asn Ala Asn Tyr Asn Asp Val Ala Pro Phe Glu Val Arg Leu Tyr Lys
                325                 330                 335

Asn Lys Asp Met Ile Gln Thr Leu Thr Asn Lys Ser Lys Ile Gln Asn
            340                 345                 350

Val Gly Gly Thr Tyr Glu Leu His Val Gly Asp Thr Ile Asp Leu Ile
        355                 360                 365

Phe Asn Ser Glu His Gln Val Leu Lys Asn Asn Thr Tyr Trp Gly Ile
    370                 375                 380

Ile Leu Leu Ala Asn Pro Gln Phe Ile Ser Gly Ser Ser Ser Ser Ser
385                 390                 395                 400

Ser Ser Ser Gly Ser Cys Asp Lys Thr His Thr Cys Pro Pro Cys Pro
                405                 410                 415

Ala Pro Glu Leu Leu Gly Gly Pro Ser Val Phe Leu Phe Pro Pro Lys
            420                 425                 430

Pro Lys Asp Thr Leu Met Ile Ser Arg Thr Pro Glu Val Thr Cys Val
        435                 440                 445

Val Val Asp Val Ser His Glu Asp Pro Glu Val Lys Phe Asn Trp Tyr
    450                 455                 460

Val Asp Gly Val Glu Val His Asn Ala Lys Thr Lys Pro Arg Glu Glu
465                 470                 475                 480

Gln Tyr Ser Ser Thr Tyr Arg Val Val Ser Val Leu Thr Val Leu His
                485                 490                 495

Gln Asp Trp Leu Asn Gly Lys Glu Tyr Lys Cys Lys Val Ser Asn Lys
            500                 505                 510
```

```
Ala Leu Pro Ala Pro Ile Glu Lys Thr Ile Ser Lys Ala Lys Gly Gln
        515                 520                 525

Pro Arg Glu Pro Gln Val Tyr Thr Leu Pro Pro Ser Arg Glu Glu Met
    530                 535                 540

Thr Lys Asn Gln Val Ser Leu Thr Cys Leu Val Lys Gly Phe Tyr Pro
545                 550                 555                 560

Ser Asp Ile Ala Val Glu Trp Glu Ser Asn Gly Gln Pro Glu Asn Asn
                565                 570                 575

Tyr Lys Thr Thr Pro Pro Val Leu Asp Ser Asp Gly Ser Phe Phe Leu
            580                 585                 590

Tyr Ser Lys Leu Thr Val Asp Lys Ser Arg Trp Gln Gln Gly Asn Val
        595                 600                 605

Phe Ser Cys Ser Val Met His Glu Ala Leu His Asn His Tyr Thr Gln
    610                 615                 620

Lys Ser Leu Ser Leu Ser Pro Gly Lys
625                 630


<210> SEQ ID NO 28
<211> LENGTH: 647
<212> TYPE: PRT
<213> ORGANISM: Artificial Sequence
<220> FEATURE:
<223> OTHER INFORMATION: GITRL-wt fused to Seq_13 (no sig, no glyco)

<400> SEQUENCE: 28

Glu Thr Ala Lys Glu Pro Cys Met Ala Lys Phe Gly Pro Leu Pro Ser
1               5                   10                  15

Lys Trp Gln Met Ala Ser Ser Glu Pro Pro Cys Val Asn Lys Val Ser
            20                  25                  30

Asp Trp Lys Leu Glu Ile Leu Gln Asn Gly Leu Tyr Leu Ile Tyr Gly
        35                  40                  45

Gln Val Ala Pro Asn Ala Asn Tyr Asn Asp Val Ala Pro Phe Glu Val
    50                  55                  60

Arg Leu Tyr Lys Asn Lys Asp Met Ile Gln Thr Leu Thr Asn Lys Ser
65                  70                  75                  80

Lys Ile Gln Asn Val Gly Gly Thr Tyr Glu Leu His Val Gly Asp Thr
                85                  90                  95

Ile Asp Leu Ile Phe Asn Ser Glu His Gln Val Leu Lys Asn Asn Thr
            100                 105                 110

Tyr Trp Gly Ile Ile Leu Leu Ala Asn Pro Gln Phe Ile Ser Gly Ser
        115                 120                 125

Gly Ser Gly Asn Gly Ser Glu Thr Ala Lys Glu Pro Cys Met Ala Lys
    130                 135                 140

Phe Gly Pro Leu Pro Ser Lys Trp Gln Met Ala Ser Ser Glu Pro Pro
145                 150                 155                 160

Cys Val Asn Lys Val Ser Asp Trp Lys Leu Glu Ile Leu Gln Asn Gly
                165                 170                 175

Leu Tyr Leu Ile Tyr Gly Gln Val Ala Pro Asn Ala Asn Tyr Asn Asp
            180                 185                 190

Val Ala Pro Phe Glu Val Arg Leu Tyr Lys Asn Lys Asp Met Ile Gln
        195                 200                 205

Thr Leu Thr Asn Lys Ser Lys Ile Gln Asn Val Gly Gly Thr Tyr Glu
    210                 215                 220

Leu His Val Gly Asp Thr Ile Asp Leu Ile Phe Asn Ser Glu His Gln
225                 230                 235                 240
```

```
Val Leu Lys Asn Asn Thr Tyr Trp Gly Ile Ile Leu Leu Ala Asn Pro
                245                 250                 255

Gln Phe Ile Ser Gly Ser Gly Ser Gly Asn Gly Ser Glu Thr Ala Lys
            260                 265                 270

Glu Pro Cys Met Ala Lys Phe Gly Pro Leu Pro Ser Lys Trp Gln Met
        275                 280                 285

Ala Ser Ser Glu Pro Pro Cys Val Asn Lys Val Ser Asp Trp Lys Leu
    290                 295                 300

Glu Ile Leu Gln Asn Gly Leu Tyr Leu Ile Tyr Gly Gln Val Ala Pro
305                 310                 315                 320

Asn Ala Asn Tyr Asn Asp Val Ala Pro Phe Glu Val Arg Leu Tyr Lys
                325                 330                 335

Asn Lys Asp Met Ile Gln Thr Leu Thr Asn Lys Ser Lys Ile Gln Asn
            340                 345                 350

Val Gly Gly Thr Tyr Glu Leu His Val Gly Asp Thr Ile Asp Leu Ile
        355                 360                 365

Phe Asn Ser Glu His Gln Val Leu Lys Asn Asn Thr Tyr Trp Gly Ile
    370                 375                 380

Ile Leu Leu Ala Asn Pro Gln Phe Ile Ser Gly Ser Ser Ser Ser Ser
385                 390                 395                 400

Ser Ser Ser Gly Ser Cys Asp Lys Thr His Thr Cys Pro Pro Cys Pro
                405                 410                 415

Ala Pro Glu Leu Leu Gly Gly Pro Ser Val Phe Leu Phe Pro Pro Lys
            420                 425                 430

Pro Lys Asp Thr Leu Met Ile Ser Arg Thr Pro Glu Val Thr Cys Val
        435                 440                 445

Val Val Asp Val Ser His Glu Asp Pro Glu Val Lys Phe Asn Trp Tyr
    450                 455                 460

Val Asp Gly Val Glu Val His Asn Ala Lys Thr Lys Pro Arg Glu Glu
465                 470                 475                 480

Gln Tyr Ser Ser Thr Tyr Arg Val Val Ser Val Leu Thr Val Leu His
                485                 490                 495

Gln Asp Trp Leu Asn Gly Lys Glu Tyr Lys Cys Lys Val Ser Asn Lys
            500                 505                 510

Ala Leu Pro Ala Pro Ile Glu Lys Thr Ile Ser Lys Ala Lys Gly Gln
        515                 520                 525

Pro Arg Glu Pro Gln Val Tyr Thr Leu Pro Pro Ser Arg Glu Glu Met
    530                 535                 540

Thr Lys Asn Gln Val Ser Leu Thr Cys Leu Val Lys Gly Phe Tyr Pro
545                 550                 555                 560

Ser Asp Ile Ala Val Glu Trp Glu Ser Asn Gly Gln Pro Glu Asn Asn
                565                 570                 575

Tyr Lys Thr Thr Pro Pro Val Leu Asp Ser Asp Gly Ser Phe Phe Leu
            580                 585                 590

Tyr Ser Lys Leu Thr Val Asp Lys Ser Arg Trp Gln Gln Gly Asn Val
        595                 600                 605

Phe Ser Cys Ser Val Met His Glu Ala Leu His Asn His Tyr Thr Gln
    610                 615                 620

Lys Ser Leu Ser Leu Ser Pro Gly Ser Ser Ser Ser Ser Ser Ala Trp
625                 630                 635                 640

Ser His Pro Gln Phe Glu Lys
                645
```

<210> SEQ ID NO 29
<211> LENGTH: 632
<212> TYPE: PRT
<213> ORGANISM: Artificial Sequence
<220> FEATURE:
<223> OTHER INFORMATION: GITRL-wt fused to Seq14 (no sig, no strep tag)

<400> SEQUENCE: 29

```
Glu Thr Ala Lys Glu Pro Cys Met Ala Lys Phe Gly Pro Leu Pro Ser
1               5                   10                  15

Lys Trp Gln Met Ala Ser Ser Glu Pro Pro Cys Val Asn Lys Val Ser
            20                  25                  30

Asp Trp Lys Leu Glu Ile Leu Gln Asn Gly Leu Tyr Leu Ile Tyr Gly
        35                  40                  45

Gln Val Ala Pro Asn Ala Asn Tyr Asn Asp Val Ala Pro Phe Glu Val
    50                  55                  60

Arg Leu Tyr Lys Asn Lys Asp Met Ile Gln Thr Leu Thr Asn Lys Ser
65                  70                  75                  80

Lys Ile Gln Asn Val Gly Gly Thr Tyr Glu Leu His Val Gly Asp Thr
                85                  90                  95

Ile Asp Leu Ile Phe Asn Ser Glu His Gln Val Leu Lys Asn Asn Thr
            100                 105                 110

Tyr Trp Gly Ile Ile Leu Leu Ala Asn Pro Gln Phe Ile Ser Gly Ser
        115                 120                 125

Gly Ser Gly Asn Gly Ser Glu Thr Ala Lys Glu Pro Cys Met Ala Lys
    130                 135                 140

Phe Gly Pro Leu Pro Ser Lys Trp Gln Met Ala Ser Ser Glu Pro Pro
145                 150                 155                 160

Cys Val Asn Lys Val Ser Asp Trp Lys Leu Glu Ile Leu Gln Asn Gly
                165                 170                 175

Leu Tyr Leu Ile Tyr Gly Gln Val Ala Pro Asn Ala Asn Tyr Asn Asp
            180                 185                 190

Val Ala Pro Phe Glu Val Arg Leu Tyr Lys Asn Lys Asp Met Ile Gln
        195                 200                 205

Thr Leu Thr Asn Lys Ser Lys Ile Gln Asn Val Gly Gly Thr Tyr Glu
    210                 215                 220

Leu His Val Gly Asp Thr Ile Asp Leu Ile Phe Asn Ser Glu His Gln
225                 230                 235                 240

Val Leu Lys Asn Asn Thr Tyr Trp Gly Ile Ile Leu Leu Ala Asn Pro
                245                 250                 255

Gln Phe Ile Ser Gly Ser Gly Ser Gly Asn Gly Ser Glu Thr Ala Lys
            260                 265                 270

Glu Pro Cys Met Ala Lys Phe Gly Pro Leu Pro Ser Lys Trp Gln Met
        275                 280                 285

Ala Ser Ser Glu Pro Pro Cys Val Asn Lys Val Ser Asp Trp Lys Leu
    290                 295                 300

Glu Ile Leu Gln Asn Gly Leu Tyr Leu Ile Tyr Gly Gln Val Ala Pro
305                 310                 315                 320

Asn Ala Asn Tyr Asn Asp Val Ala Pro Phe Glu Val Arg Leu Tyr Lys
                325                 330                 335

Asn Lys Asp Met Ile Gln Thr Leu Thr Asn Lys Ser Lys Ile Gln Asn
            340                 345                 350

Val Gly Gly Thr Tyr Glu Leu His Val Gly Asp Thr Ile Asp Leu Ile
        355                 360                 365
```

```
Phe Asn Ser Glu His Gln Val Leu Lys Asn Asn Thr Tyr Trp Gly Ile
    370                 375                 380

Ile Leu Leu Ala Asn Pro Gln Phe Ile Ser Gly Ser Ser Ser Ser Ser
385                 390                 395                 400

Ser Ser Ser Gly Ser Cys Asp Lys Thr His Thr Cys Pro Pro Cys Pro
                405                 410                 415

Ala Pro Pro Val Ala Gly Pro Ser Val Phe Leu Phe Pro Pro Lys Pro
            420                 425                 430

Lys Asp Thr Leu Met Ile Ser Arg Thr Pro Glu Val Thr Cys Val Val
        435                 440                 445

Val Asp Val Ser His Glu Asp Pro Glu Val Lys Phe Asn Trp Tyr Val
    450                 455                 460

Asp Gly Val Glu Val His Asn Ala Lys Thr Lys Pro Arg Glu Glu Gln
465                 470                 475                 480

Tyr Asn Ser Thr Tyr Arg Val Val Ser Val Leu Thr Val Leu His Gln
                485                 490                 495

Asp Trp Leu Asn Gly Lys Glu Tyr Lys Cys Lys Val Ser Asn Lys Gly
            500                 505                 510

Leu Pro Ser Ser Ile Glu Lys Thr Ile Ser Lys Ala Lys Gly Gln Pro
        515                 520                 525

Arg Glu Pro Gln Val Tyr Thr Leu Pro Pro Ser Arg Glu Glu Met Thr
    530                 535                 540

Lys Asn Gln Val Ser Leu Thr Cys Leu Val Lys Gly Phe Tyr Pro Ser
545                 550                 555                 560

Asp Ile Ala Val Glu Trp Glu Ser Asn Gly Gln Pro Glu Asn Asn Tyr
                565                 570                 575

Lys Thr Thr Pro Pro Val Leu Asp Ser Asp Gly Ser Phe Phe Leu Tyr
            580                 585                 590

Ser Lys Leu Thr Val Asp Lys Ser Arg Trp Gln Gln Gly Asn Val Phe
        595                 600                 605

Ser Cys Ser Val Met His Glu Ala Leu His Asn His Tyr Thr Gln Lys
    610                 615                 620

Ser Leu Ser Leu Ser Pro Gly Lys
625                 630
```

<210> SEQ ID NO 30
<211> LENGTH: 633
<212> TYPE: PRT
<213> ORGANISM: Artificial Sequence
<220> FEATURE:
<223> OTHER INFORMATION: example

<400> SEQUENCE: 30

```
Gln Thr Ala Lys Glu Pro Cys Met Ala Lys Phe Gly Pro Leu Pro Ser
1               5                   10                  15

Lys Trp Gln Met Ala Ser Ser Glu Pro Pro Cys Val Asn Lys Val Ser
            20                  25                  30

Asp Trp Lys Leu Glu Ile Leu Gln Asn Gly Leu Tyr Leu Ile Tyr Gly
        35                  40                  45

Gln Val Ala Pro Asn Ala Asn Tyr Asn Asp Val Ala Pro Phe Glu Val
    50                  55                  60

Arg Leu Tyr Lys Asn Lys Asp Met Ile Gln Thr Leu Thr Asn Lys Ser
65                  70                  75                  80

Lys Ile Gln Asn Val Gly Gly Thr Tyr Glu Leu His Val Gly Asp Thr
                85                  90                  95
```

-continued

```
Ile Asp Leu Ile Phe Asn Ser Glu His Gln Val Leu Lys Asn Asn Thr
            100                 105                 110

Tyr Trp Gly Ile Ile Leu Leu Ala Asn Pro Gln Phe Ile Ser Gly Ser
        115                 120                 125

Gly Ser Gly Asn Gly Ser Glu Thr Ala Lys Glu Pro Cys Met Ala Lys
    130                 135                 140

Phe Gly Pro Leu Pro Ser Lys Trp Gln Met Ala Ser Ser Glu Pro Pro
145                 150                 155                 160

Cys Val Asn Lys Val Ser Asp Trp Lys Leu Glu Ile Leu Gln Asn Gly
                165                 170                 175

Leu Tyr Leu Ile Tyr Gly Gln Val Ala Pro Asn Ala Asn Tyr Asn Asp
            180                 185                 190

Val Ala Pro Phe Glu Val Arg Leu Tyr Lys Asn Lys Asp Met Ile Gln
        195                 200                 205

Thr Leu Thr Asn Lys Ser Lys Ile Gln Asn Val Gly Gly Thr Tyr Glu
    210                 215                 220

Leu His Val Gly Asp Thr Ile Asp Leu Ile Phe Asn Ser Glu His Gln
225                 230                 235                 240

Val Leu Lys Asn Asn Thr Tyr Trp Gly Ile Ile Leu Leu Ala Asn Pro
                245                 250                 255

Gln Phe Ile Ser Gly Ser Gly Ser Gly Asn Gly Ser Glu Thr Ala Lys
            260                 265                 270

Glu Pro Cys Met Ala Lys Phe Gly Pro Leu Pro Ser Lys Trp Gln Met
        275                 280                 285

Ala Ser Ser Glu Pro Pro Cys Val Asn Lys Val Ser Asp Trp Lys Leu
    290                 295                 300

Glu Ile Leu Gln Asn Gly Leu Tyr Leu Ile Tyr Gly Gln Val Ala Pro
305                 310                 315                 320

Asn Ala Asn Tyr Asn Asp Val Ala Pro Phe Glu Val Arg Leu Tyr Lys
                325                 330                 335

Asn Lys Asp Met Ile Gln Thr Leu Thr Asn Lys Ser Lys Ile Gln Asn
            340                 345                 350

Val Gly Gly Thr Tyr Glu Leu His Val Gly Asp Thr Ile Asp Leu Ile
        355                 360                 365

Phe Asn Ser Glu His Gln Val Leu Lys Asn Asn Thr Tyr Trp Gly Ile
    370                 375                 380

Ile Leu Leu Ala Asn Pro Gln Phe Ile Ser Gly Ser Ser Ser Ser Ser
385                 390                 395                 400

Ser Ser Ser Gly Ser Cys Asp Lys Thr His Thr Cys Pro Pro Cys Pro
                405                 410                 415

Ala Pro Glu Leu Leu Gly Gly Pro Ser Val Phe Leu Phe Pro Pro Lys
            420                 425                 430

Pro Lys Asp Thr Leu Met Ile Ser Arg Thr Pro Glu Val Thr Cys Val
        435                 440                 445

Val Val Asp Val Ser His Glu Asp Pro Glu Val Lys Phe Asn Trp Tyr
    450                 455                 460

Val Asp Gly Val Glu Val His Asn Ala Lys Thr Lys Pro Arg Glu Glu
465                 470                 475                 480

Gln Tyr Ser Ser Thr Tyr Arg Val Val Ser Val Leu Thr Val Leu His
                485                 490                 495

Gln Asp Trp Leu Asn Gly Lys Glu Tyr Lys Cys Lys Val Ser Asn Lys
            500                 505                 510

Ala Leu Pro Ala Pro Ile Glu Lys Thr Ile Ser Lys Ala Lys Gly Gln
```

```
        515                 520                 525

Pro Arg Glu Pro Gln Val Tyr Thr Leu Pro Pro Ser Arg Glu Glu Met
    530                 535                 540

Thr Lys Asn Gln Val Ser Leu Thr Cys Leu Val Lys Gly Phe Tyr Pro
545                 550                 555                 560

Ser Asp Ile Ala Val Glu Trp Glu Ser Asn Gly Gln Pro Glu Asn Asn
                565                 570                 575

Tyr Lys Thr Thr Pro Pro Val Leu Asp Ser Asp Gly Ser Phe Phe Leu
            580                 585                 590

Tyr Ser Lys Leu Thr Val Asp Lys Ser Arg Trp Gln Gln Gly Asn Val
        595                 600                 605

Phe Ser Cys Ser Val Met His Glu Ala Leu His Asn His Tyr Thr Gln
    610                 615                 620

Lys Ser Leu Ser Leu Ser Pro Gly Lys
625                 630


<210> SEQ ID NO 31
<211> LENGTH: 619
<212> TYPE: PRT
<213> ORGANISM: Artificial Sequence
<220> FEATURE:
<223> OTHER INFORMATION: example

<400> SEQUENCE: 31

Gln Pro Cys Met Ala Lys Phe Gly Pro Leu Pro Ser Lys Trp Gln Met
1               5                   10                  15

Ala Ser Ser Glu Pro Pro Cys Val Asn Lys Val Ser Asp Trp Lys Leu
            20                  25                  30

Glu Ile Leu Gln Asn Gly Leu Tyr Leu Ile Tyr Gly Gln Val Ala Pro
        35                  40                  45

Asn Ala Asn Tyr Asn Asp Val Ala Pro Phe Glu Val Arg Leu Tyr Lys
    50                  55                  60

Asn Lys Asp Met Ile Gln Thr Leu Thr Asn Lys Ser Lys Ile Gln Asn
65                  70                  75                  80

Val Gly Gly Thr Tyr Glu Leu His Val Gly Asp Thr Ile Asp Leu Ile
                85                  90                  95

Phe Asn Ser Glu His Gln Val Leu Lys Asn Asn Thr Tyr Trp Gly Ile
            100                 105                 110

Ile Leu Leu Ala Asn Pro Gln Phe Ile Ser Gly Ser Gly Ser Gly Asn
        115                 120                 125

Gly Ser Pro Cys Met Ala Lys Phe Gly Pro Leu Pro Ser Lys Trp Gln
    130                 135                 140

Met Ala Ser Ser Glu Pro Pro Cys Val Asn Lys Val Ser Asp Trp Lys
145                 150                 155                 160

Leu Glu Ile Leu Gln Asn Gly Leu Tyr Leu Ile Tyr Gly Gln Val Ala
                165                 170                 175

Pro Asn Ala Asn Tyr Asn Asp Val Ala Pro Phe Glu Val Arg Leu Tyr
            180                 185                 190

Lys Asn Lys Asp Met Ile Gln Thr Leu Thr Asn Lys Ser Lys Ile Gln
        195                 200                 205

Asn Val Gly Gly Thr Tyr Glu Leu His Val Gly Asp Thr Ile Asp Leu
    210                 215                 220

Ile Phe Asn Ser Glu His Gln Val Leu Lys Asn Asn Thr Tyr Trp Gly
225                 230                 235                 240

Ile Ile Leu Leu Ala Asn Pro Gln Phe Ile Ser Gly Ser Gly Ser Gly
```

-continued

```
                245                 250                 255

Asn Gly Ser Pro Cys Met Ala Lys Phe Gly Pro Leu Pro Ser Lys Trp
            260                 265                 270

Gln Met Ala Ser Ser Glu Pro Pro Cys Val Asn Lys Val Ser Asp Trp
        275                 280                 285

Lys Leu Glu Ile Leu Gln Asn Gly Leu Tyr Leu Ile Tyr Gly Gln Val
    290                 295                 300

Ala Pro Asn Ala Asn Tyr Asn Asp Val Ala Pro Phe Glu Val Arg Leu
305                 310                 315                 320

Tyr Lys Asn Lys Asp Met Ile Gln Thr Leu Thr Asn Lys Ser Lys Ile
                325                 330                 335

Gln Asn Val Gly Gly Thr Tyr Glu Leu His Val Gly Asp Thr Ile Asp
            340                 345                 350

Leu Ile Phe Asn Ser Glu His Gln Val Leu Lys Asn Asn Thr Tyr Trp
        355                 360                 365

Gly Ile Ile Leu Leu Ala Asn Pro Gln Phe Ile Ser Gly Ser Ser Ser
    370                 375                 380

Ser Ser Ser Ser Ser Gly Ser Cys Asp Lys Thr His Thr Cys Pro Pro
385                 390                 395                 400

Cys Pro Ala Pro Glu Leu Leu Gly Gly Pro Ser Val Phe Leu Phe Pro
                405                 410                 415

Pro Lys Pro Lys Asp Thr Leu Met Ile Ser Arg Thr Pro Glu Val Thr
            420                 425                 430

Cys Val Val Val Asp Val Ser His Glu Asp Pro Glu Val Lys Phe Asn
        435                 440                 445

Trp Tyr Val Asp Gly Val Glu Val His Asn Ala Lys Thr Lys Pro Arg
    450                 455                 460

Glu Glu Gln Tyr Ser Ser Thr Tyr Arg Val Val Ser Val Leu Thr Val
465                 470                 475                 480

Leu His Gln Asp Trp Leu Asn Gly Lys Glu Tyr Lys Cys Lys Val Ser
                485                 490                 495

Asn Lys Ala Leu Pro Ala Pro Ile Glu Lys Thr Ile Ser Lys Ala Lys
            500                 505                 510

Gly Gln Pro Arg Glu Pro Gln Val Tyr Thr Leu Pro Pro Ser Arg Glu
        515                 520                 525

Glu Met Thr Lys Asn Gln Val Ser Leu Thr Cys Leu Val Lys Gly Phe
    530                 535                 540

Tyr Pro Ser Asp Ile Ala Val Glu Trp Glu Ser Asn Gly Gln Pro Glu
545                 550                 555                 560

Asn Asn Tyr Lys Thr Thr Pro Pro Val Leu Asp Ser Asp Gly Ser Phe
                565                 570                 575

Phe Leu Tyr Ser Lys Leu Thr Val Asp Lys Ser Arg Trp Gln Gln Gly
            580                 585                 590

Asn Val Phe Ser Cys Ser Val Met His Glu Ala Leu His Asn His Tyr
        595                 600                 605

Thr Gln Lys Ser Leu Ser Leu Ser Pro Gly Lys
    610                 615
```

<210> SEQ ID NO 32
<211> LENGTH: 618
<212> TYPE: PRT
<213> ORGANISM: Artificial Sequence
<220> FEATURE:
<223> OTHER INFORMATION: example

<400> SEQUENCE: 32

Gln Pro Cys Met Ala Lys Phe Gly Pro Leu Pro Ser Lys Trp Gln Met
1               5                   10                  15

Ala Ser Ser Glu Pro Pro Cys Val Asn Lys Val Ser Asp Trp Lys Leu
            20                  25                  30

Glu Ile Leu Gln Asn Gly Leu Tyr Leu Ile Tyr Gly Gln Val Ala Pro
        35                  40                  45

Asn Ala Asn Tyr Asn Asp Val Ala Pro Phe Glu Val Arg Leu Tyr Lys
    50                  55                  60

Asn Lys Asp Met Ile Gln Thr Leu Thr Asn Lys Ser Lys Ile Gln Asn
65                  70                  75                  80

Val Gly Gly Thr Tyr Glu Leu His Val Gly Asp Thr Ile Asp Leu Ile
                85                  90                  95

Phe Asn Ser Glu His Gln Val Leu Lys Asn Asn Thr Tyr Trp Gly Ile
            100                 105                 110

Ile Leu Leu Ala Asn Pro Gln Phe Ile Ser Gly Ser Gly Ser Gly Asn
        115                 120                 125

Gly Ser Glu Pro Cys Met Ala Lys Phe Gly Pro Leu Pro Ser Lys Trp
    130                 135                 140

Gln Met Ala Ser Ser Glu Pro Pro Cys Val Asn Lys Val Ser Asp Trp
145                 150                 155                 160

Lys Leu Glu Ile Leu Gln Asn Gly Leu Tyr Leu Ile Tyr Gly Gln Val
                165                 170                 175

Ala Pro Asn Ala Asn Tyr Asn Asp Val Ala Pro Phe Glu Val Arg Leu
            180                 185                 190

Tyr Lys Asn Lys Asp Met Ile Gln Thr Leu Thr Asn Lys Ser Lys Ile
        195                 200                 205

Gln Asn Val Gly Gly Thr Tyr Glu Leu His Val Gly Asp Thr Ile Asp
    210                 215                 220

Leu Ile Phe Asn Ser Glu His Gln Val Leu Lys Asn Asn Thr Tyr Trp
225                 230                 235                 240

Gly Ile Ile Leu Leu Ala Asn Pro Gln Phe Ile Ser Gly Ser Gly Ser
                245                 250                 255

Gly Asn Gly Ser Glu Pro Cys Met Ala Lys Phe Gly Pro Leu Pro Ser
            260                 265                 270

Lys Trp Gln Met Ala Ser Ser Glu Pro Pro Cys Val Asn Lys Val Ser
        275                 280                 285

Asp Trp Lys Leu Glu Ile Leu Gln Asn Gly Leu Tyr Leu Ile Tyr Gly
    290                 295                 300

Gln Val Ala Pro Asn Ala Asn Tyr Asn Asp Val Ala Pro Phe Glu Val
305                 310                 315                 320

Arg Leu Tyr Lys Asn Lys Asp Met Ile Gln Thr Leu Thr Asn Lys Ser
                325                 330                 335

Lys Ile Gln Asn Val Gly Gly Thr Tyr Glu Leu His Val Gly Asp Thr
            340                 345                 350

Ile Asp Leu Ile Phe Asn Ser Glu His Gln Val Leu Lys Asn Asn Thr
        355                 360                 365

Tyr Trp Gly Ile Ile Leu Leu Ala Asn Pro Gln Phe Ile Ser Gly Ser
    370                 375                 380

Ser Ser Ser Ser Gly Ser Cys Asp Lys Thr His Thr Cys Pro Pro Cys
385                 390                 395                 400

Pro Ala Pro Glu Leu Leu Gly Gly Pro Ser Val Phe Leu Phe Pro Pro
                405                 410                 415

```
Lys Pro Lys Asp Thr Leu Met Ile Ser Arg Thr Pro Glu Val Thr Cys
            420                 425                 430

Val Val Val Asp Val Ser His Glu Asp Pro Glu Val Lys Phe Asn Trp
        435                 440                 445

Tyr Val Asp Gly Val Glu Val His Asn Ala Lys Thr Lys Pro Arg Glu
    450                 455                 460

Glu Gln Tyr Ser Ser Thr Tyr Arg Val Val Ser Val Leu Thr Val Leu
465                 470                 475                 480

His Gln Asp Trp Leu Asn Gly Lys Glu Tyr Lys Cys Lys Val Ser Asn
                485                 490                 495

Lys Ala Leu Pro Ala Pro Ile Glu Lys Thr Ile Ser Lys Ala Lys Gly
            500                 505                 510

Gln Pro Arg Glu Pro Gln Val Tyr Thr Leu Pro Pro Ser Arg Glu Glu
        515                 520                 525

Met Thr Lys Asn Gln Val Ser Leu Thr Cys Leu Val Lys Gly Phe Tyr
    530                 535                 540

Pro Ser Asp Ile Ala Val Glu Trp Glu Ser Asn Gly Gln Pro Glu Asn
545                 550                 555                 560

Asn Tyr Lys Thr Thr Pro Pro Val Leu Asp Ser Asp Gly Ser Phe Phe
                565                 570                 575

Leu Tyr Ser Lys Leu Thr Val Asp Lys Ser Arg Trp Gln Gln Gly Asn
            580                 585                 590

Val Phe Ser Cys Ser Val Met His Glu Ala Leu His Asn His Tyr Thr
        595                 600                 605

Gln Lys Ser Leu Ser Leu Ser Pro Gly Lys
    610                 615


<210> SEQ ID NO 33
<211> LENGTH: 601
<212> TYPE: PRT
<213> ORGANISM: Artificial Sequence
<220> FEATURE:
<223> OTHER INFORMATION: example

<400> SEQUENCE: 33

Gln Pro Cys Met Ala Lys Phe Gly Pro Leu Pro Ser Lys Trp Gln Met
1               5                   10                  15

Ala Ser Ser Glu Pro Pro Cys Val Asn Lys Val Ser Asp Trp Lys Leu
            20                  25                  30

Glu Ile Leu Gln Asn Gly Leu Tyr Leu Ile Tyr Gly Gln Val Ala Pro
        35                  40                  45

Asn Ala Asn Tyr Asn Asp Val Ala Pro Phe Glu Val Arg Leu Tyr Lys
    50                  55                  60

Asn Lys Asp Met Ile Gln Thr Leu Thr Asn Lys Ser Lys Ile Gln Asn
65                  70                  75                  80

Val Gly Gly Thr Tyr Glu Leu His Val Gly Asp Thr Ile Asp Leu Ile
                85                  90                  95

Phe Asn Ser Glu His Gln Val Leu Lys Asn Asn Thr Tyr Trp Gly Ile
            100                 105                 110

Ile Leu Leu Ala Gly Ser Gly Ser Gly Asn Gly Ser Pro Cys Met Ala
        115                 120                 125

Lys Phe Gly Pro Leu Pro Ser Lys Trp Gln Met Ala Ser Ser Glu Pro
    130                 135                 140

Pro Cys Val Asn Lys Val Ser Asp Trp Lys Leu Glu Ile Leu Gln Asn
145                 150                 155                 160
```

```
Gly Leu Tyr Leu Ile Tyr Gly Gln Val Ala Pro Asn Ala Asn Tyr Asn
                165                 170                 175

Asp Val Ala Pro Phe Glu Val Arg Leu Tyr Lys Asn Lys Asp Met Ile
            180                 185                 190

Gln Thr Leu Thr Asn Lys Ser Lys Ile Gln Asn Val Gly Gly Thr Tyr
        195                 200                 205

Glu Leu His Val Gly Asp Thr Ile Asp Leu Ile Phe Asn Ser Glu His
    210                 215                 220

Gln Val Leu Lys Asn Asn Thr Tyr Trp Gly Ile Ile Leu Leu Ala Gly
225                 230                 235                 240

Ser Gly Ser Gly Asn Gly Ser Pro Cys Met Ala Lys Phe Gly Pro Leu
                245                 250                 255

Pro Ser Lys Trp Gln Met Ala Ser Ser Glu Pro Pro Cys Val Asn Lys
            260                 265                 270

Val Ser Asp Trp Lys Leu Glu Ile Leu Gln Asn Gly Leu Tyr Leu Ile
        275                 280                 285

Tyr Gly Gln Val Ala Pro Asn Ala Asn Tyr Asn Asp Val Ala Pro Phe
    290                 295                 300

Glu Val Arg Leu Tyr Lys Asn Lys Asp Met Ile Gln Thr Leu Thr Asn
305                 310                 315                 320

Lys Ser Lys Ile Gln Asn Val Gly Gly Thr Tyr Glu Leu His Val Gly
                325                 330                 335

Asp Thr Ile Asp Leu Ile Phe Asn Ser Glu His Gln Val Leu Lys Asn
            340                 345                 350

Asn Thr Tyr Trp Gly Ile Ile Leu Leu Ala Gly Ser Ser Ser Ser Ser
        355                 360                 365

Ser Ser Ser Gly Ser Cys Asp Lys Thr His Thr Cys Pro Pro Cys Pro
    370                 375                 380

Ala Pro Glu Leu Leu Gly Gly Pro Ser Val Phe Leu Phe Pro Pro Lys
385                 390                 395                 400

Pro Lys Asp Thr Leu Met Ile Ser Arg Thr Pro Glu Val Thr Cys Val
                405                 410                 415

Val Val Asp Val Ser His Glu Asp Pro Glu Val Lys Phe Asn Trp Tyr
            420                 425                 430

Val Asp Gly Val Glu Val His Asn Ala Lys Thr Lys Pro Arg Glu Glu
        435                 440                 445

Gln Tyr Ser Ser Thr Tyr Arg Val Val Ser Val Leu Thr Val Leu His
    450                 455                 460

Gln Asp Trp Leu Asn Gly Lys Glu Tyr Lys Cys Lys Val Ser Asn Lys
465                 470                 475                 480

Ala Leu Pro Ala Pro Ile Glu Lys Thr Ile Ser Lys Ala Lys Gly Gln
                485                 490                 495

Pro Arg Glu Pro Gln Val Tyr Thr Leu Pro Pro Ser Arg Glu Glu Met
            500                 505                 510

Thr Lys Asn Gln Val Ser Leu Thr Cys Leu Val Lys Gly Phe Tyr Pro
        515                 520                 525

Ser Asp Ile Ala Val Glu Trp Glu Ser Asn Gly Gln Pro Glu Asn Asn
    530                 535                 540

Tyr Lys Thr Thr Pro Pro Val Leu Asp Ser Asp Gly Ser Phe Phe Leu
545                 550                 555                 560

Tyr Ser Lys Leu Thr Val Asp Lys Ser Arg Trp Gln Gln Gly Asn Val
                565                 570                 575
```

```
Phe Ser Cys Ser Val Met His Glu Ala Leu His Asn His Tyr Thr Gln
            580                 585                 590

Lys Ser Leu Ser Leu Ser Pro Gly Lys
        595                 600


<210> SEQ ID NO 34
<211> LENGTH: 624
<212> TYPE: PRT
<213> ORGANISM: Artificial Sequence
<220> FEATURE:
<223> OTHER INFORMATION: example

<400> SEQUENCE: 34

Gln Glu Pro Cys Met Ala Lys Phe Gly Pro Leu Pro Ser Lys Trp Gln
1               5                   10                  15

Met Ala Ser Ser Glu Pro Pro Cys Val Asn Lys Val Ser Asp Trp Lys
            20                  25                  30

Leu Glu Ile Leu Gln Asn Gly Leu Tyr Leu Ile Tyr Gly Gln Val Ala
        35                  40                  45

Pro Asn Ala Asn Tyr Asn Asp Val Ala Pro Phe Glu Val Arg Leu Tyr
    50                  55                  60

Lys Asn Lys Asp Met Ile Gln Thr Leu Thr Asn Lys Ser Lys Ile Gln
65                  70                  75                  80

Asn Val Gly Gly Thr Tyr Glu Leu His Val Gly Asp Thr Ile Asp Leu
                85                  90                  95

Ile Phe Asn Ser Glu His Gln Val Leu Lys Asn Asn Thr Tyr Trp Gly
            100                 105                 110

Ile Ile Leu Leu Ala Asn Pro Gln Phe Ile Ser Gly Ser Gly Ser Gly
        115                 120                 125

Asn Gly Ser Lys Glu Pro Cys Met Ala Lys Phe Gly Pro Leu Pro Ser
    130                 135                 140

Lys Trp Gln Met Ala Ser Ser Glu Pro Pro Cys Val Asn Lys Val Ser
145                 150                 155                 160

Asp Trp Lys Leu Glu Ile Leu Gln Asn Gly Leu Tyr Leu Ile Tyr Gly
                165                 170                 175

Gln Val Ala Pro Asn Ala Asn Tyr Asn Asp Val Ala Pro Phe Glu Val
            180                 185                 190

Arg Leu Tyr Lys Asn Lys Asp Met Ile Gln Thr Leu Thr Asn Lys Ser
        195                 200                 205

Lys Ile Gln Asn Val Gly Gly Thr Tyr Glu Leu His Val Gly Asp Thr
    210                 215                 220

Ile Asp Leu Ile Phe Asn Ser Glu His Gln Val Leu Lys Asn Asn Thr
225                 230                 235                 240

Tyr Trp Gly Ile Ile Leu Leu Ala Asn Pro Gln Phe Ile Ser Gly Ser
                245                 250                 255

Gly Ser Gly Asn Gly Ser Lys Glu Pro Cys Met Ala Lys Phe Gly Pro
            260                 265                 270

Leu Pro Ser Lys Trp Gln Met Ala Ser Ser Glu Pro Pro Cys Val Asn
        275                 280                 285

Lys Val Ser Asp Trp Lys Leu Glu Ile Leu Gln Asn Gly Leu Tyr Leu
    290                 295                 300

Ile Tyr Gly Gln Val Ala Pro Asn Ala Asn Tyr Asn Asp Val Ala Pro
305                 310                 315                 320

Phe Glu Val Arg Leu Tyr Lys Asn Lys Asp Met Ile Gln Thr Leu Thr
                325                 330                 335
```

```
Asn Lys Ser Lys Ile Gln Asn Val Gly Gly Thr Tyr Glu Leu His Val
            340                 345                 350

Gly Asp Thr Ile Asp Leu Ile Phe Asn Ser Glu His Gln Val Leu Lys
        355                 360                 365

Asn Asn Thr Tyr Trp Gly Ile Ile Leu Leu Ala Asn Pro Gln Phe Ile
    370                 375                 380

Ser Gly Ser Ser Ser Ser Ser Ser Ser Ser Gly Ser Cys Asp Lys Thr
385                 390                 395                 400

His Thr Cys Pro Pro Cys Pro Ala Pro Glu Leu Leu Gly Gly Pro Ser
                405                 410                 415

Val Phe Leu Phe Pro Pro Lys Pro Lys Asp Thr Leu Met Ile Ser Arg
            420                 425                 430

Thr Pro Glu Val Thr Cys Val Val Val Asp Val Ser His Glu Asp Pro
        435                 440                 445

Glu Val Lys Phe Asn Trp Tyr Val Asp Gly Val Glu Val His Asn Ala
    450                 455                 460

Lys Thr Lys Pro Arg Glu Glu Gln Tyr Ser Ser Thr Tyr Arg Val Val
465                 470                 475                 480

Ser Val Leu Thr Val Leu His Gln Asp Trp Leu Asn Gly Lys Glu Tyr
                485                 490                 495

Lys Cys Lys Val Ser Asn Lys Ala Leu Pro Ala Pro Ile Glu Lys Thr
            500                 505                 510

Ile Ser Lys Ala Lys Gly Gln Pro Arg Glu Pro Gln Val Tyr Thr Leu
        515                 520                 525

Pro Pro Ser Arg Glu Glu Met Thr Lys Asn Gln Val Ser Leu Thr Cys
    530                 535                 540

Leu Val Lys Gly Phe Tyr Pro Ser Asp Ile Ala Val Glu Trp Glu Ser
545                 550                 555                 560

Asn Gly Gln Pro Glu Asn Asn Tyr Lys Thr Thr Pro Pro Val Leu Asp
                565                 570                 575

Ser Asp Gly Ser Phe Phe Leu Tyr Ser Lys Leu Thr Val Asp Lys Ser
            580                 585                 590

Arg Trp Gln Gln Gly Asn Val Phe Ser Cys Ser Val Met His Glu Ala
        595                 600                 605

Leu His Asn His Tyr Thr Gln Lys Ser Leu Ser Leu Ser Pro Gly Lys
    610                 615                 620
```

<210> SEQ ID NO 35
<211> LENGTH: 609
<212> TYPE: PRT
<213> ORGANISM: Artificial Sequence
<220> FEATURE:
<223> OTHER INFORMATION: example

<400> SEQUENCE: 35

```
Gln Pro Cys Met Ala Lys Phe Gly Pro Leu Pro Ser Lys Trp Gln Met
1               5                   10                  15

Ala Ser Ser Glu Pro Pro Cys Val Asn Lys Val Ser Asp Trp Lys Leu
            20                  25                  30

Glu Ile Leu Gln Asn Gly Leu Tyr Leu Ile Tyr Gly Gln Val Ala Pro
        35                  40                  45

Asn Ala Asn Tyr Asn Asp Val Ala Pro Phe Glu Val Arg Leu Tyr Lys
    50                  55                  60

Asn Lys Asp Met Ile Gln Thr Leu Thr Asn Lys Ser Lys Ile Gln Asn
65                  70                  75                  80
```

-continued

```
Val Gly Gly Thr Tyr Glu Leu His Val Gly Asp Thr Ile Asp Leu Ile
                85                  90                  95

Phe Asn Ser Glu His Gln Val Leu Lys Asn Asn Thr Tyr Trp Gly Ile
            100                 105                 110

Ile Leu Leu Ala Asn Pro Gln Gly Ser Gly Ser Gly Asn Gly Ser Pro
        115                 120                 125

Cys Met Ala Lys Phe Gly Pro Leu Pro Ser Lys Trp Gln Met Ala Ser
    130                 135                 140

Ser Glu Pro Pro Cys Val Asn Lys Val Ser Asp Trp Lys Leu Glu Ile
145                 150                 155                 160

Leu Gln Asn Gly Leu Tyr Leu Ile Tyr Gly Gln Val Ala Pro Asn Ala
                165                 170                 175

Asn Tyr Asn Asp Val Ala Pro Phe Glu Val Arg Leu Tyr Lys Asn Lys
            180                 185                 190

Asp Met Ile Gln Thr Leu Thr Asn Lys Ser Lys Ile Gln Asn Val Gly
        195                 200                 205

Gly Thr Tyr Glu Leu His Val Gly Asp Thr Ile Asp Leu Ile Phe Asn
    210                 215                 220

Ser Glu His Gln Val Leu Lys Asn Asn Thr Tyr Trp Gly Ile Ile Leu
225                 230                 235                 240

Leu Ala Asn Pro Gly Ser Gly Ser Gly Asn Gly Ser Pro Cys Met Ala
                245                 250                 255

Lys Phe Gly Pro Leu Pro Ser Lys Trp Gln Met Ala Ser Ser Glu Pro
            260                 265                 270

Pro Cys Val Asn Lys Val Ser Asp Trp Lys Leu Glu Ile Leu Gln Asn
        275                 280                 285

Gly Leu Tyr Leu Ile Tyr Gly Gln Val Ala Pro Asn Ala Asn Tyr Asn
    290                 295                 300

Asp Val Ala Pro Phe Glu Val Arg Leu Tyr Lys Asn Lys Asp Met Ile
305                 310                 315                 320

Gln Thr Leu Thr Asn Lys Ser Lys Ile Gln Asn Val Gly Gly Thr Tyr
                325                 330                 335

Glu Leu His Val Gly Asp Thr Ile Asp Leu Ile Phe Asn Ser Glu His
            340                 345                 350

Gln Val Leu Lys Asn Asn Thr Tyr Trp Gly Ile Ile Leu Leu Ala Asn
        355                 360                 365

Pro Gln Gly Ser Ser Ser Ser Ser Ser Ser Ser Gly Ser Cys Asp Lys
    370                 375                 380

Thr His Thr Cys Pro Pro Cys Pro Ala Pro Glu Leu Leu Gly Gly Pro
385                 390                 395                 400

Ser Val Phe Leu Phe Pro Pro Lys Pro Lys Asp Thr Leu Met Ile Ser
                405                 410                 415

Arg Thr Pro Glu Val Thr Cys Val Val Val Asp Val Ser His Glu Asp
            420                 425                 430

Pro Glu Val Lys Phe Asn Trp Tyr Val Asp Gly Val Glu Val His Asn
        435                 440                 445

Ala Lys Thr Lys Pro Arg Glu Glu Gln Tyr Ser Ser Thr Tyr Arg Val
    450                 455                 460

Val Ser Val Leu Thr Val Leu His Gln Asp Trp Leu Asn Gly Lys Glu
465                 470                 475                 480

Tyr Lys Cys Lys Val Ser Asn Lys Ala Leu Pro Ala Pro Ile Glu Lys
                485                 490                 495

Thr Ile Ser Lys Ala Lys Gly Gln Pro Arg Glu Pro Gln Val Tyr Thr
```

```
            500                 505                 510

Leu Pro Pro Ser Arg Glu Glu Met Thr Lys Asn Gln Val Ser Leu Thr
        515                 520                 525

Cys Leu Val Lys Gly Phe Tyr Pro Ser Asp Ile Ala Val Glu Trp Glu
    530                 535                 540

Ser Asn Gly Gln Pro Glu Asn Asn Tyr Lys Thr Thr Pro Pro Val Leu
545                 550                 555                 560

Asp Ser Asp Gly Ser Phe Phe Leu Tyr Ser Lys Leu Thr Val Asp Lys
                565                 570                 575

Ser Arg Trp Gln Gln Gly Asn Val Phe Ser Cys Ser Val Met His Glu
            580                 585                 590

Ala Leu His Asn His Tyr Thr Gln Lys Ser Leu Ser Leu Ser Pro Gly
        595                 600                 605

Lys


<210> SEQ ID NO 36
<211> LENGTH: 394
<212> TYPE: PRT
<213> ORGANISM: Artificial Sequence
<220> FEATURE:
<223> OTHER INFORMATION: example of scGITRL-RBD

<400> SEQUENCE: 36

Glu Thr Ala Lys Glu Pro Cys Met Ala Lys Phe Gly Pro Leu Pro Ser
1               5                   10                  15

Lys Trp Gln Met Ala Ser Ser Glu Pro Pro Cys Val Asn Lys Val Ser
            20                  25                  30

Asp Trp Lys Leu Glu Ile Leu Gln Asn Gly Leu Tyr Leu Ile Tyr Gly
        35                  40                  45

Gln Val Ala Pro Asn Ala Asn Tyr Asn Asp Val Ala Pro Phe Glu Val
    50                  55                  60

Arg Leu Tyr Lys Asn Lys Asp Met Ile Gln Thr Leu Thr Asn Lys Ser
65                  70                  75                  80

Lys Ile Gln Asn Val Gly Gly Thr Tyr Glu Leu His Val Gly Asp Thr
                85                  90                  95

Ile Asp Leu Ile Phe Asn Ser Glu His Gln Val Leu Lys Asn Asn Thr
            100                 105                 110

Tyr Trp Gly Ile Ile Leu Leu Ala Asn Pro Gln Phe Ile Ser Gly Ser
        115                 120                 125

Gly Ser Gly Asn Gly Ser Glu Thr Ala Lys Glu Pro Cys Met Ala Lys
    130                 135                 140

Phe Gly Pro Leu Pro Ser Lys Trp Gln Met Ala Ser Ser Glu Pro Pro
145                 150                 155                 160

Cys Val Asn Lys Val Ser Asp Trp Lys Leu Glu Ile Leu Gln Asn Gly
                165                 170                 175

Leu Tyr Leu Ile Tyr Gly Gln Val Ala Pro Asn Ala Asn Tyr Asn Asp
            180                 185                 190

Val Ala Pro Phe Glu Val Arg Leu Tyr Lys Asn Lys Asp Met Ile Gln
        195                 200                 205

Thr Leu Thr Asn Lys Ser Lys Ile Gln Asn Val Gly Gly Thr Tyr Glu
    210                 215                 220

Leu His Val Gly Asp Thr Ile Asp Leu Ile Phe Asn Ser Glu His Gln
225                 230                 235                 240

Val Leu Lys Asn Asn Thr Tyr Trp Gly Ile Ile Leu Leu Ala Asn Pro
                245                 250                 255
```

```
Gln Phe Ile Ser Gly Ser Gly Ser Gly Asn Gly Ser Glu Thr Ala Lys
            260                 265                 270

Glu Pro Cys Met Ala Lys Phe Gly Pro Leu Pro Ser Lys Trp Gln Met
        275                 280                 285

Ala Ser Ser Glu Pro Pro Cys Val Asn Lys Val Ser Asp Trp Lys Leu
    290                 295                 300

Glu Ile Leu Gln Asn Gly Leu Tyr Leu Ile Tyr Gly Gln Val Ala Pro
305                 310                 315                 320

Asn Ala Asn Tyr Asn Asp Val Ala Pro Phe Glu Val Arg Leu Tyr Lys
                325                 330                 335

Asn Lys Asp Met Ile Gln Thr Leu Thr Asn Lys Ser Lys Ile Gln Asn
            340                 345                 350

Val Gly Gly Thr Tyr Glu Leu His Val Gly Asp Thr Ile Asp Leu Ile
        355                 360                 365

Phe Asn Ser Glu His Gln Val Leu Lys Asn Asn Thr Tyr Trp Gly Ile
    370                 375                 380

Ile Leu Leu Ala Asn Pro Gln Phe Ile Ser
385                 390


<210> SEQ ID NO 37
<211> LENGTH: 2006
<212> TYPE: DNA
<213> ORGANISM: Artificial Sequence
<220> FEATURE:
<223> OTHER INFORMATION: nucl. acid sequence of GITR receptor agonist
      fusion protein

<400> SEQUENCE: 37

aagctttagg gataacaggg taatagccgc caccatggag actgacaccc tgctggtgtt     60

cgtgctgctg gtctgggtgc ctgcaggaaa tggagaaact gccaaagagc cctgtatggc    120

caagtttggc cctcttccct ctaagtggca gatggcttcc tctgaaccac catgcgtgaa    180

caaagtgagc gactggaaac tggagatctt gcagaacggg ctgtatttga tctacggcca    240

ggtggcccct aatgctaact ataacgatgt agccccattt gaggtcagac tgtataagaa    300

taaggacatg attcagactc tgaccaataa gtccaagatc cagaatgtgg gaggcactta    360

cgaattgcac gtgggtgata ccatcgattt gatcttcaac agcgaacatc aggtgctcaa    420

gaacaataca tactggggaa ttatactgct ggcaaaccca cagttcattt ccgggtccgg    480

ttctggtaac ggctctgaga cagcaaaaga gccctgcatg gcaaaattcg gtcctctgcc    540

cagtaagtgg caaatggcat catccgaacc tccctgtgtg aataaggtgt cagactggaa    600

acttgagatc cttcagaatg gactctacct catctatgga caggttgctc ctaacgctaa    660

ttacaatgat gtggctccct tcgaagttcg gctgtacaag aataaggata tgatacagac    720

ccttactaac aaaagcaaaa ttcagaacgt gggcggaaca tacgagctgc atgtcggtga    780

cacgattgat ctgatcttca actcagagca tcaggtcctg aagaataaca cctactgggg    840

cattattctg ctcgccaatc cccaatttat atccgggagc gggtcaggca acggcagtga    900

gacagccaag gaaccatgta tggctaaatt tgggcccctg ccatctaaat ggcagatggc    960

atctagcgaa cctccctgcg ttaacaaggt atccgactgg aaattggaga tcctccagaa   1020

cggactgtac ctgatctatg gccaagtcgc cccaaatgcc aattacaatg acgtagctcc   1080

ctttgaggtc aggctctata agaacaaaga catgattcaa acacttacca acaagagtaa   1140

gatacagaat gtgggcggaa cctatgaact gcacgttggg gataccattg acctgatctt   1200
```

-continued

```
caacagtgag caccaagtcc tcaagaataa cacttattgg ggtatcatcc tgctggccaa   1260

ccctcagttt atcagcggat cctcgagttc atcgtcctca tccggctcat gtgataagac   1320

ccacacctgc cctccctgtc ctgcccctga gctgctgggc ggaccttctg tgttcctgtt   1380

cccccccaag cctaaggaca ccctgatgat ctccaggacc cctgaggtga cctgtgtggt   1440

ggtggacgtg tctcacgaag atcccgaggt gaagttcaac tggtacgtgg acggcgtgga   1500

ggtccacaac gccaagacca agcctaggga ggagcagtac agctccacct accgggtggt   1560

gtctgtgctg accgtgctgc accaggattg gctgaacgga aaggagtata agtgtaaggt   1620

ctccaacaag gccctgcctg cccccatcga gaaaaccatc tccaaggcca agggccagcc   1680

tcgggagcct caggtgtaca ccctgcctcc tagcagggag gagatgacca agaaccaggt   1740

gtccctgacc tgtctggtga agggcttcta cccttccgat atcgccgtgg agtgggagtc   1800

taatggccag cccgagaaca actacaagac cacccctcct gtgctggact ctgacggctc   1860

cttcttcctg tactccaagc tgaccgtgga caagtccaga tggcagcagg gcaacgtgtt   1920

ctcctgctcc gtgatgcacg aggccctgca caatcactac acccagaagt ccctgtctct   1980

gagtccgggc aagtaatagg cgcgcc                                        2006
```

<210> SEQ ID NO 38
<211> LENGTH: 203
<212> TYPE: PRT
<213> ORGANISM: Artificial Sequence
<220> FEATURE:
<223> OTHER INFORMATION: GITRL fused to RB69 FOLDON

<400> SEQUENCE: 38

```
Met Glu Thr Asp Thr Leu Leu Val Phe Val Leu Leu Val Trp Val Pro
1               5                   10                  15

Ala Gly Asn Gly Glu Thr Ala Lys Glu Pro Cys Met Ala Lys Phe Gly
            20                  25                  30

Pro Leu Pro Ser Lys Trp Gln Met Ala Ser Ser Glu Pro Pro Cys Val
        35                  40                  45

Asn Lys Val Ser Asp Trp Lys Leu Glu Ile Leu Gln Asn Gly Leu Tyr
    50                  55                  60

Leu Ile Tyr Gly Gln Val Ala Pro Asn Ala Asn Tyr Asn Asp Val Ala
65                  70                  75                  80

Pro Phe Glu Val Arg Leu Tyr Lys Asn Lys Asp Met Ile Gln Thr Leu
                85                  90                  95

Thr Asn Lys Ser Lys Ile Gln Asn Val Gly Gly Thr Tyr Glu Leu His
            100                 105                 110

Val Gly Asp Thr Ile Asp Leu Ile Phe Asn Ser Glu His Gln Val Leu
        115                 120                 125

Lys Asn Asn Thr Tyr Trp Gly Ile Ile Leu Leu Ala Asn Pro Gln Phe
    130                 135                 140

Ile Ser Gly Ser Gly Ser Ser Gly Ser Ser Gly Ser Ser Gly Ser Gly
145                 150                 155                 160

Tyr Ile Glu Asp Ala Pro Ser Asp Gly Lys Phe Tyr Val Arg Lys Asp
                165                 170                 175

Gly Ala Trp Val Glu Leu Pro Thr Ala Ser Gly Pro Ser Ser Ser Ser
            180                 185                 190

Ser Ser Ala Trp Ser His Pro Gln Phe Glu Lys
        195                 200
```

<210> SEQ ID NO 39

<211> LENGTH: 394
<212> TYPE: PRT
<213> ORGANISM: Artificial Sequence
<220> FEATURE:
<223> OTHER INFORMATION: example of scGITRL-RBD

<400> SEQUENCE: 39

Gln Thr Ala Lys Glu Pro Cys Met Ala Lys Phe Gly Pro Leu Pro Ser
1 5 10 15

Lys Trp Gln Met Ala Ser Ser Glu Pro Pro Cys Val Asn Lys Val Ser
20 25 30

Asp Trp Lys Leu Glu Ile Leu Gln Asn Gly Leu Tyr Leu Ile Tyr Gly
35 40 45

Gln Val Ala Pro Asn Ala Asn Tyr Asn Asp Val Ala Pro Phe Glu Val
50 55 60

Arg Leu Tyr Lys Asn Lys Asp Met Ile Gln Thr Leu Thr Asn Lys Ser
65 70 75 80

Lys Ile Gln Asn Val Gly Gly Thr Tyr Glu Leu His Val Gly Asp Thr
85 90 95

Ile Asp Leu Ile Phe Asn Ser Glu His Gln Val Leu Lys Asn Asn Thr
100 105 110

Tyr Trp Gly Ile Ile Leu Leu Ala Asn Pro Gln Phe Ile Ser Gly Ser
115 120 125

Gly Ser Gly Asn Gly Ser Glu Thr Ala Lys Glu Pro Cys Met Ala Lys
130 135 140

Phe Gly Pro Leu Pro Ser Lys Trp Gln Met Ala Ser Ser Glu Pro Pro
145 150 155 160

Cys Val Asn Lys Val Ser Asp Trp Lys Leu Glu Ile Leu Gln Asn Gly
165 170 175

Leu Tyr Leu Ile Tyr Gly Gln Val Ala Pro Asn Ala Asn Tyr Asn Asp
180 185 190

Val Ala Pro Phe Glu Val Arg Leu Tyr Lys Asn Lys Asp Met Ile Gln
195 200 205

Thr Leu Thr Asn Lys Ser Lys Ile Gln Asn Val Gly Gly Thr Tyr Glu
210 215 220

Leu His Val Gly Asp Thr Ile Asp Leu Ile Phe Asn Ser Glu His Gln
225 230 235 240

Val Leu Lys Asn Asn Thr Tyr Trp Gly Ile Ile Leu Leu Ala Asn Pro
245 250 255

Gln Phe Ile Ser Gly Ser Gly Ser Gly Asn Gly Ser Glu Thr Ala Lys
260 265 270

Glu Pro Cys Met Ala Lys Phe Gly Pro Leu Pro Ser Lys Trp Gln Met
275 280 285

Ala Ser Ser Glu Pro Pro Cys Val Asn Lys Val Ser Asp Trp Lys Leu
290 295 300

Glu Ile Leu Gln Asn Gly Leu Tyr Leu Ile Tyr Gly Gln Val Ala Pro
305 310 315 320

Asn Ala Asn Tyr Asn Asp Val Ala Pro Phe Glu Val Arg Leu Tyr Lys
325 330 335

Asn Lys Asp Met Ile Gln Thr Leu Thr Asn Lys Ser Lys Ile Gln Asn
340 345 350

Val Gly Gly Thr Tyr Glu Leu His Val Gly Asp Thr Ile Asp Leu Ile
355 360 365

Phe Asn Ser Glu His Gln Val Leu Lys Asn Asn Thr Tyr Trp Gly Ile
370 375 380

```
Ile Leu Leu Ala Asn Pro Gln Phe Ile Ser
385                 390


<210> SEQ ID NO 40
<211> LENGTH: 382
<212> TYPE: PRT
<213> ORGANISM: Artificial Sequence
<220> FEATURE:
<223> OTHER INFORMATION: example of scGITRL-RBD

<400> SEQUENCE: 40

Glu Pro Cys Met Ala Lys Phe Gly Pro Leu Pro Ser Lys Trp Gln Met
1               5                   10                  15

Ala Ser Ser Glu Pro Pro Cys Val Asn Lys Val Ser Asp Trp Lys Leu
            20                  25                  30

Glu Ile Leu Gln Asn Gly Leu Tyr Leu Ile Tyr Gly Gln Val Ala Pro
        35                  40                  45

Asn Ala Asn Tyr Asn Asp Val Ala Pro Phe Glu Val Arg Leu Tyr Lys
    50                  55                  60

Asn Lys Asp Met Ile Gln Thr Leu Thr Asn Lys Ser Lys Ile Gln Asn
65                  70                  75                  80

Val Gly Gly Thr Tyr Glu Leu His Val Gly Asp Thr Ile Asp Leu Ile
                85                  90                  95

Phe Asn Ser Glu His Gln Val Leu Lys Asn Asn Thr Tyr Trp Gly Ile
            100                 105                 110

Ile Leu Leu Ala Asn Pro Gln Phe Ile Ser Gly Ser Gly Ser Gly Asn
        115                 120                 125

Gly Ser Glu Pro Cys Met Ala Lys Phe Gly Pro Leu Pro Ser Lys Trp
    130                 135                 140

Gln Met Ala Ser Ser Glu Pro Pro Cys Val Asn Lys Val Ser Asp Trp
145                 150                 155                 160

Lys Leu Glu Ile Leu Gln Asn Gly Leu Tyr Leu Ile Tyr Gly Gln Val
                165                 170                 175

Ala Pro Asn Ala Asn Tyr Asn Asp Val Ala Pro Phe Glu Val Arg Leu
            180                 185                 190

Tyr Lys Asn Lys Asp Met Ile Gln Thr Leu Thr Asn Lys Ser Lys Ile
        195                 200                 205

Gln Asn Val Gly Gly Thr Tyr Glu Leu His Val Gly Asp Thr Ile Asp
    210                 215                 220

Leu Ile Phe Asn Ser Glu His Gln Val Leu Lys Asn Asn Thr Tyr Trp
225                 230                 235                 240

Gly Ile Ile Leu Leu Ala Asn Pro Gln Phe Ile Ser Gly Ser Gly Ser
                245                 250                 255

Gly Asn Gly Ser Glu Pro Cys Met Ala Lys Phe Gly Pro Leu Pro Ser
            260                 265                 270

Lys Trp Gln Met Ala Ser Ser Glu Pro Pro Cys Val Asn Lys Val Ser
        275                 280                 285

Asp Trp Lys Leu Glu Ile Leu Gln Asn Gly Leu Tyr Leu Ile Tyr Gly
    290                 295                 300

Gln Val Ala Pro Asn Ala Asn Tyr Asn Asp Val Ala Pro Phe Glu Val
305                 310                 315                 320

Arg Leu Tyr Lys Asn Lys Asp Met Ile Gln Thr Leu Thr Asn Lys Ser
                325                 330                 335

Lys Ile Gln Asn Val Gly Gly Thr Tyr Glu Leu His Val Gly Asp Thr
            340                 345                 350
```

```
Ile Asp Leu Ile Phe Asn Ser Glu His Gln Val Leu Lys Asn Asn Thr
        355                 360                 365

Tyr Trp Gly Ile Ile Leu Leu Ala Asn Pro Gln Phe Ile Ser
    370                 375                 380


<210> SEQ ID NO 41
<211> LENGTH: 382
<212> TYPE: PRT
<213> ORGANISM: Artificial Sequence
<220> FEATURE:
<223> OTHER INFORMATION: example of scGITRL-RBD

<400> SEQUENCE: 41

Gln Pro Cys Met Ala Lys Phe Gly Pro Leu Pro Ser Lys Trp Gln Met
1               5                   10                  15

Ala Ser Ser Glu Pro Pro Cys Val Asn Lys Val Ser Asp Trp Lys Leu
            20                  25                  30

Glu Ile Leu Gln Asn Gly Leu Tyr Leu Ile Tyr Gly Gln Val Ala Pro
        35                  40                  45

Asn Ala Asn Tyr Asn Asp Val Ala Pro Phe Glu Val Arg Leu Tyr Lys
    50                  55                  60

Asn Lys Asp Met Ile Gln Thr Leu Thr Asn Lys Ser Lys Ile Gln Asn
65                  70                  75                  80

Val Gly Gly Thr Tyr Glu Leu His Val Gly Asp Thr Ile Asp Leu Ile
                85                  90                  95

Phe Asn Ser Glu His Gln Val Leu Lys Asn Asn Thr Tyr Trp Gly Ile
            100                 105                 110

Ile Leu Leu Ala Asn Pro Gln Phe Ile Ser Gly Ser Gly Ser Gly Asn
        115                 120                 125

Gly Ser Glu Pro Cys Met Ala Lys Phe Gly Pro Leu Pro Ser Lys Trp
    130                 135                 140

Gln Met Ala Ser Ser Glu Pro Pro Cys Val Asn Lys Val Ser Asp Trp
145                 150                 155                 160

Lys Leu Glu Ile Leu Gln Asn Gly Leu Tyr Leu Ile Tyr Gly Gln Val
                165                 170                 175

Ala Pro Asn Ala Asn Tyr Asn Asp Val Ala Pro Phe Glu Val Arg Leu
            180                 185                 190

Tyr Lys Asn Lys Asp Met Ile Gln Thr Leu Thr Asn Lys Ser Lys Ile
        195                 200                 205

Gln Asn Val Gly Gly Thr Tyr Glu Leu His Val Gly Asp Thr Ile Asp
    210                 215                 220

Leu Ile Phe Asn Ser Glu His Gln Val Leu Lys Asn Asn Thr Tyr Trp
225                 230                 235                 240

Gly Ile Ile Leu Leu Ala Asn Pro Gln Phe Ile Ser Gly Ser Gly Ser
                245                 250                 255

Gly Asn Gly Ser Glu Pro Cys Met Ala Lys Phe Gly Pro Leu Pro Ser
            260                 265                 270

Lys Trp Gln Met Ala Ser Ser Glu Pro Pro Cys Val Asn Lys Val Ser
        275                 280                 285

Asp Trp Lys Leu Glu Ile Leu Gln Asn Gly Leu Tyr Leu Ile Tyr Gly
    290                 295                 300

Gln Val Ala Pro Asn Ala Asn Tyr Asn Asp Val Ala Pro Phe Glu Val
305                 310                 315                 320

Arg Leu Tyr Lys Asn Lys Asp Met Ile Gln Thr Leu Thr Asn Lys Ser
                325                 330                 335
```

Lys Ile Gln Asn Val Gly Gly Thr Tyr Glu Leu His Val Gly Asp Thr
340 345 350

Ile Asp Leu Ile Phe Asn Ser Glu His Gln Val Leu Lys Asn Asn Thr
355 360 365

Tyr Trp Gly Ile Ile Leu Leu Ala Asn Pro Gln Phe Ile Ser
370 375 380

<210> SEQ ID NO 42
<211> LENGTH: 385
<212> TYPE: PRT
<213> ORGANISM: Artificial Sequence
<220> FEATURE:
<223> OTHER INFORMATION: example of scGITRL-RBD

<400> SEQUENCE: 42

Lys Glu Pro Cys Met Ala Lys Phe Gly Pro Leu Pro Ser Lys Trp Gln
1 5 10 15

Met Ala Ser Ser Glu Pro Pro Cys Val Asn Lys Val Ser Asp Trp Lys
20 25 30

Leu Glu Ile Leu Gln Asn Gly Leu Tyr Leu Ile Tyr Gly Gln Val Ala
35 40 45

Pro Asn Ala Asn Tyr Asn Asp Val Ala Pro Phe Glu Val Arg Leu Tyr
50 55 60

Lys Asn Lys Asp Met Ile Gln Thr Leu Thr Asn Lys Ser Lys Ile Gln
65 70 75 80

Asn Val Gly Gly Thr Tyr Glu Leu His Val Gly Asp Thr Ile Asp Leu
85 90 95

Ile Phe Asn Ser Glu His Gln Val Leu Lys Asn Asn Thr Tyr Trp Gly
100 105 110

Ile Ile Leu Leu Ala Asn Pro Gln Phe Ile Ser Gly Ser Gly Ser Gly
115 120 125

Asn Gly Ser Lys Glu Pro Cys Met Ala Lys Phe Gly Pro Leu Pro Ser
130 135 140

Lys Trp Gln Met Ala Ser Ser Glu Pro Pro Cys Val Asn Lys Val Ser
145 150 155 160

Asp Trp Lys Leu Glu Ile Leu Gln Asn Gly Leu Tyr Leu Ile Tyr Gly
165 170 175

Gln Val Ala Pro Asn Ala Asn Tyr Asn Asp Val Ala Pro Phe Glu Val
180 185 190

Arg Leu Tyr Lys Asn Lys Asp Met Ile Gln Thr Leu Thr Asn Lys Ser
195 200 205

Lys Ile Gln Asn Val Gly Gly Thr Tyr Glu Leu His Val Gly Asp Thr
210 215 220

Ile Asp Leu Ile Phe Asn Ser Glu His Gln Val Leu Lys Asn Asn Thr
225 230 235 240

Tyr Trp Gly Ile Ile Leu Leu Ala Asn Pro Gln Phe Ile Ser Gly Ser
245 250 255

Gly Ser Gly Asn Gly Ser Lys Glu Pro Cys Met Ala Lys Phe Gly Pro
260 265 270

Leu Pro Ser Lys Trp Gln Met Ala Ser Ser Glu Pro Pro Cys Val Asn
275 280 285

Lys Val Ser Asp Trp Lys Leu Glu Ile Leu Gln Asn Gly Leu Tyr Leu
290 295 300

Ile Tyr Gly Gln Val Ala Pro Asn Ala Asn Tyr Asn Asp Val Ala Pro
305 310 315 320

```
Phe Glu Val Arg Leu Tyr Lys Asn Lys Asp Met Ile Gln Thr Leu Thr
                325                 330                 335

Asn Lys Ser Lys Ile Gln Asn Val Gly Gly Thr Tyr Glu Leu His Val
            340                 345                 350

Gly Asp Thr Ile Asp Leu Ile Phe Asn Ser Glu His Gln Val Leu Lys
        355                 360                 365

Asn Asn Thr Tyr Trp Gly Ile Ile Leu Leu Ala Asn Pro Gln Phe Ile
    370                 375                 380

Ser
385


<210> SEQ ID NO 43
<211> LENGTH: 385
<212> TYPE: PRT
<213> ORGANISM: Artificial Sequence
<220> FEATURE:
<223> OTHER INFORMATION: example of scGITRL-RBD

<400> SEQUENCE: 43

Gln Glu Pro Cys Met Ala Lys Phe Gly Pro Leu Pro Ser Lys Trp Gln
1               5                   10                  15

Met Ala Ser Ser Glu Pro Pro Cys Val Asn Lys Val Ser Asp Trp Lys
            20                  25                  30

Leu Glu Ile Leu Gln Asn Gly Leu Tyr Leu Ile Tyr Gly Gln Val Ala
        35                  40                  45

Pro Asn Ala Asn Tyr Asn Asp Val Ala Pro Phe Glu Val Arg Leu Tyr
    50                  55                  60

Lys Asn Lys Asp Met Ile Gln Thr Leu Thr Asn Lys Ser Lys Ile Gln
65                  70                  75                  80

Asn Val Gly Gly Thr Tyr Glu Leu His Val Gly Asp Thr Ile Asp Leu
                85                  90                  95

Ile Phe Asn Ser Glu His Gln Val Leu Lys Asn Asn Thr Tyr Trp Gly
            100                 105                 110

Ile Ile Leu Leu Ala Asn Pro Gln Phe Ile Ser Gly Ser Gly Ser Gly
        115                 120                 125

Asn Gly Ser Lys Glu Pro Cys Met Ala Lys Phe Gly Pro Leu Pro Ser
    130                 135                 140

Lys Trp Gln Met Ala Ser Ser Glu Pro Pro Cys Val Asn Lys Val Ser
145                 150                 155                 160

Asp Trp Lys Leu Glu Ile Leu Gln Asn Gly Leu Tyr Leu Ile Tyr Gly
                165                 170                 175

Gln Val Ala Pro Asn Ala Asn Tyr Asn Asp Val Ala Pro Phe Glu Val
            180                 185                 190

Arg Leu Tyr Lys Asn Lys Asp Met Ile Gln Thr Leu Thr Asn Lys Ser
        195                 200                 205

Lys Ile Gln Asn Val Gly Gly Thr Tyr Glu Leu His Val Gly Asp Thr
    210                 215                 220

Ile Asp Leu Ile Phe Asn Ser Glu His Gln Val Leu Lys Asn Asn Thr
225                 230                 235                 240

Tyr Trp Gly Ile Ile Leu Leu Ala Asn Pro Gln Phe Ile Ser Gly Ser
                245                 250                 255

Gly Ser Gly Asn Gly Ser Lys Glu Pro Cys Met Ala Lys Phe Gly Pro
            260                 265                 270

Leu Pro Ser Lys Trp Gln Met Ala Ser Ser Glu Pro Pro Cys Val Asn
        275                 280                 285
```

```
Lys Val Ser Asp Trp Lys Leu Glu Ile Leu Gln Asn Gly Leu Tyr Leu
    290                 295                 300

Ile Tyr Gly Gln Val Ala Pro Asn Ala Asn Tyr Asn Asp Val Ala Pro
305                 310                 315                 320

Phe Glu Val Arg Leu Tyr Lys Asn Lys Asp Met Ile Gln Thr Leu Thr
                325                 330                 335

Asn Lys Ser Lys Ile Gln Asn Val Gly Gly Thr Tyr Glu Leu His Val
            340                 345                 350

Gly Asp Thr Ile Asp Leu Ile Phe Asn Ser Glu His Gln Val Leu Lys
        355                 360                 365

Asn Asn Thr Tyr Trp Gly Ile Ile Leu Leu Ala Asn Pro Gln Phe Ile
    370                 375                 380

Ser
385


<210> SEQ ID NO 44
<211> LENGTH: 380
<212> TYPE: PRT
<213> ORGANISM: Artificial Sequence
<220> FEATURE:
<223> OTHER INFORMATION: example of scGITRL-RBD

<400> SEQUENCE: 44

Glu Pro Cys Met Ala Lys Phe Gly Pro Leu Pro Ser Lys Trp Gln Met
1               5                   10                  15

Ala Ser Ser Glu Pro Pro Cys Val Asn Lys Val Ser Asp Trp Lys Leu
            20                  25                  30

Glu Ile Leu Gln Asn Gly Leu Tyr Leu Ile Tyr Gly Gln Val Ala Pro
        35                  40                  45

Asn Ala Asn Tyr Asn Asp Val Ala Pro Phe Glu Val Arg Leu Tyr Lys
    50                  55                  60

Asn Lys Asp Met Ile Gln Thr Leu Thr Asn Lys Ser Lys Ile Gln Asn
65                  70                  75                  80

Val Gly Gly Thr Tyr Glu Leu His Val Gly Asp Thr Ile Asp Leu Ile
                85                  90                  95

Phe Asn Ser Glu His Gln Val Leu Lys Asn Asn Thr Tyr Trp Gly Ile
            100                 105                 110

Ile Leu Leu Ala Asn Pro Gln Phe Ile Ser Gly Ser Gly Ser Gly Asn
        115                 120                 125

Gly Ser Pro Cys Met Ala Lys Phe Gly Pro Leu Pro Ser Lys Trp Gln
    130                 135                 140

Met Ala Ser Ser Glu Pro Pro Cys Val Asn Lys Val Ser Asp Trp Lys
145                 150                 155                 160

Leu Glu Ile Leu Gln Asn Gly Leu Tyr Leu Ile Tyr Gly Gln Val Ala
                165                 170                 175

Pro Asn Ala Asn Tyr Asn Asp Val Ala Pro Phe Glu Val Arg Leu Tyr
            180                 185                 190

Lys Asn Lys Asp Met Ile Gln Thr Leu Thr Asn Lys Ser Lys Ile Gln
        195                 200                 205

Asn Val Gly Gly Thr Tyr Glu Leu His Val Gly Asp Thr Ile Asp Leu
    210                 215                 220

Ile Phe Asn Ser Glu His Gln Val Leu Lys Asn Asn Thr Tyr Trp Gly
225                 230                 235                 240

Ile Ile Leu Leu Ala Asn Pro Gln Phe Ile Ser Gly Ser Gly Ser Gly
                245                 250                 255
```

```
Asn Gly Ser Pro Cys Met Ala Lys Phe Gly Pro Leu Pro Ser Lys Trp
            260                 265                 270

Gln Met Ala Ser Ser Glu Pro Pro Cys Val Asn Lys Val Ser Asp Trp
        275                 280                 285

Lys Leu Glu Ile Leu Gln Asn Gly Leu Tyr Leu Ile Tyr Gly Gln Val
    290                 295                 300

Ala Pro Asn Ala Asn Tyr Asn Asp Val Ala Pro Phe Glu Val Arg Leu
305                 310                 315                 320

Tyr Lys Asn Lys Asp Met Ile Gln Thr Leu Thr Asn Lys Ser Lys Ile
                325                 330                 335

Gln Asn Val Gly Gly Thr Tyr Glu Leu His Val Gly Asp Thr Ile Asp
            340                 345                 350

Leu Ile Phe Asn Ser Glu His Gln Val Leu Lys Asn Asn Thr Tyr Trp
        355                 360                 365

Gly Ile Ile Leu Leu Ala Asn Pro Gln Phe Ile Ser
    370                 375                 380


<210> SEQ ID NO 45
<211> LENGTH: 380
<212> TYPE: PRT
<213> ORGANISM: Artificial Sequence
<220> FEATURE:
<223> OTHER INFORMATION: example of scGITRL-RBD

<400> SEQUENCE: 45

Gln Pro Cys Met Ala Lys Phe Gly Pro Leu Pro Ser Lys Trp Gln Met
1               5                   10                  15

Ala Ser Ser Glu Pro Pro Cys Val Asn Lys Val Ser Asp Trp Lys Leu
            20                  25                  30

Glu Ile Leu Gln Asn Gly Leu Tyr Leu Ile Tyr Gly Gln Val Ala Pro
        35                  40                  45

Asn Ala Asn Tyr Asn Asp Val Ala Pro Phe Glu Val Arg Leu Tyr Lys
    50                  55                  60

Asn Lys Asp Met Ile Gln Thr Leu Thr Asn Lys Ser Lys Ile Gln Asn
65                  70                  75                  80

Val Gly Gly Thr Tyr Glu Leu His Val Gly Asp Thr Ile Asp Leu Ile
                85                  90                  95

Phe Asn Ser Glu His Gln Val Leu Lys Asn Asn Thr Tyr Trp Gly Ile
            100                 105                 110

Ile Leu Leu Ala Asn Pro Gln Phe Ile Ser Gly Ser Gly Ser Gly Asn
        115                 120                 125

Gly Ser Pro Cys Met Ala Lys Phe Gly Pro Leu Pro Ser Lys Trp Gln
    130                 135                 140

Met Ala Ser Ser Glu Pro Pro Cys Val Asn Lys Val Ser Asp Trp Lys
145                 150                 155                 160

Leu Glu Ile Leu Gln Asn Gly Leu Tyr Leu Ile Tyr Gly Gln Val Ala
                165                 170                 175

Pro Asn Ala Asn Tyr Asn Asp Val Ala Pro Phe Glu Val Arg Leu Tyr
            180                 185                 190

Lys Asn Lys Asp Met Ile Gln Thr Leu Thr Asn Lys Ser Lys Ile Gln
        195                 200                 205

Asn Val Gly Gly Thr Tyr Glu Leu His Val Gly Asp Thr Ile Asp Leu
    210                 215                 220

Ile Phe Asn Ser Glu His Gln Val Leu Lys Asn Asn Thr Tyr Trp Gly
225                 230                 235                 240
```

```
Ile Ile Leu Leu Ala Asn Pro Gln Phe Ile Ser Gly Ser Gly Ser Gly
                245                 250                 255

Asn Gly Ser Pro Cys Met Ala Lys Phe Gly Pro Leu Pro Ser Lys Trp
            260                 265                 270

Gln Met Ala Ser Ser Glu Pro Pro Cys Val Asn Lys Val Ser Asp Trp
        275                 280                 285

Lys Leu Glu Ile Leu Gln Asn Gly Leu Tyr Leu Ile Tyr Gly Gln Val
    290                 295                 300

Ala Pro Asn Ala Asn Tyr Asn Asp Val Ala Pro Phe Glu Val Arg Leu
305                 310                 315                 320

Tyr Lys Asn Lys Asp Met Ile Gln Thr Leu Thr Asn Lys Ser Lys Ile
                325                 330                 335

Gln Asn Val Gly Gly Thr Tyr Glu Leu His Val Gly Asp Thr Ile Asp
            340                 345                 350

Leu Ile Phe Asn Ser Glu His Gln Val Leu Lys Asn Asn Thr Tyr Trp
        355                 360                 365

Gly Ile Ile Leu Leu Ala Asn Pro Gln Phe Ile Ser
    370                 375                 380


<210> SEQ ID NO 46
<211> LENGTH: 362
<212> TYPE: PRT
<213> ORGANISM: Artificial Sequence
<220> FEATURE:
<223> OTHER INFORMATION: example of scGITRL-RBD

<400> SEQUENCE: 46

Gln Pro Cys Met Ala Lys Phe Gly Pro Leu Pro Ser Lys Trp Gln Met
1               5                   10                  15

Ala Ser Ser Glu Pro Pro Cys Val Asn Lys Val Ser Asp Trp Lys Leu
            20                  25                  30

Glu Ile Leu Gln Asn Gly Leu Tyr Leu Ile Tyr Gly Gln Val Ala Pro
        35                  40                  45

Asn Ala Asn Tyr Asn Asp Val Ala Pro Phe Glu Val Arg Leu Tyr Lys
    50                  55                  60

Asn Lys Asp Met Ile Gln Thr Leu Thr Asn Lys Ser Lys Ile Gln Asn
65                  70                  75                  80

Val Gly Gly Thr Tyr Glu Leu His Val Gly Asp Thr Ile Asp Leu Ile
                85                  90                  95

Phe Asn Ser Glu His Gln Val Leu Lys Asn Asn Thr Tyr Trp Gly Ile
            100                 105                 110

Ile Leu Leu Ala Gly Ser Gly Ser Gly Asn Gly Ser Pro Cys Met Ala
        115                 120                 125

Lys Phe Gly Pro Leu Pro Ser Lys Trp Gln Met Ala Ser Ser Glu Pro
    130                 135                 140

Pro Cys Val Asn Lys Val Ser Asp Trp Lys Leu Glu Ile Leu Gln Asn
145                 150                 155                 160

Gly Leu Tyr Leu Ile Tyr Gly Gln Val Ala Pro Asn Ala Asn Tyr Asn
                165                 170                 175

Asp Val Ala Pro Phe Glu Val Arg Leu Tyr Lys Asn Lys Asp Met Ile
            180                 185                 190

Gln Thr Leu Thr Asn Lys Ser Lys Ile Gln Asn Val Gly Gly Thr Tyr
        195                 200                 205

Glu Leu His Val Gly Asp Thr Ile Asp Leu Ile Phe Asn Ser Glu His
    210                 215                 220
```

Gln Val Leu Lys Asn Asn Thr Tyr Trp Gly Ile Ile Leu Leu Ala Gly
225 230 235 240

Ser Gly Ser Gly Asn Gly Ser Pro Cys Met Ala Lys Phe Gly Pro Leu
245 250 255

Pro Ser Lys Trp Gln Met Ala Ser Ser Glu Pro Pro Cys Val Asn Lys
260 265 270

Val Ser Asp Trp Lys Leu Glu Ile Leu Gln Asn Gly Leu Tyr Leu Ile
275 280 285

Tyr Gly Gln Val Ala Pro Asn Ala Asn Tyr Asn Asp Val Ala Pro Phe
290 295 300

Glu Val Arg Leu Tyr Lys Asn Lys Asp Met Ile Gln Thr Leu Thr Asn
305 310 315 320

Lys Ser Lys Ile Gln Asn Val Gly Gly Thr Tyr Glu Leu His Val Gly
325 330 335

Asp Thr Ile Asp Leu Ile Phe Asn Ser Glu His Gln Val Leu Lys Asn
340 345 350

Asn Thr Tyr Trp Gly Ile Ile Leu Leu Ala
355 360

<210> SEQ ID NO 47
<211> LENGTH: 370
<212> TYPE: PRT
<213> ORGANISM: Artificial Sequence
<220> FEATURE:
<223> OTHER INFORMATION: example of scGITRL-RBD

<400> SEQUENCE: 47

Gln Pro Cys Met Ala Lys Phe Gly Pro Leu Pro Ser Lys Trp Gln Met
1 5 10 15

Ala Ser Ser Glu Pro Pro Cys Val Asn Lys Val Ser Asp Trp Lys Leu
20 25 30

Glu Ile Leu Gln Asn Gly Leu Tyr Leu Ile Tyr Gly Gln Val Ala Pro
35 40 45

Asn Ala Asn Tyr Asn Asp Val Ala Pro Phe Glu Val Arg Leu Tyr Lys
50 55 60

Asn Lys Asp Met Ile Gln Thr Leu Thr Asn Lys Ser Lys Ile Gln Asn
65 70 75 80

Val Gly Gly Thr Tyr Glu Leu His Val Gly Asp Thr Ile Asp Leu Ile
85 90 95

Phe Asn Ser Glu His Gln Val Leu Lys Asn Asn Thr Tyr Trp Gly Ile
100 105 110

Ile Leu Leu Ala Asn Pro Gln Gly Ser Gly Ser Gly Asn Gly Ser Pro
115 120 125

Cys Met Ala Lys Phe Gly Pro Leu Pro Ser Lys Trp Gln Met Ala Ser
130 135 140

Ser Glu Pro Pro Cys Val Asn Lys Val Ser Asp Trp Lys Leu Glu Ile
145 150 155 160

Leu Gln Asn Gly Leu Tyr Leu Ile Tyr Gly Gln Val Ala Pro Asn Ala
165 170 175

Asn Tyr Asn Asp Val Ala Pro Phe Glu Val Arg Leu Tyr Lys Asn Lys
180 185 190

Asp Met Ile Gln Thr Leu Thr Asn Lys Ser Lys Ile Gln Asn Val Gly
195 200 205

Gly Thr Tyr Glu Leu His Val Gly Asp Thr Ile Asp Leu Ile Phe Asn
210 215 220

Ser Glu His Gln Val Leu Lys Asn Asn Thr Tyr Trp Gly Ile Ile Leu
225 230 235 240

Leu Ala Asn Pro Gly Ser Gly Ser Gly Asn Gly Ser Pro Cys Met Ala
245 250 255

Lys Phe Gly Pro Leu Pro Ser Lys Trp Gln Met Ala Ser Ser Glu Pro
260 265 270

Pro Cys Val Asn Lys Val Ser Asp Trp Lys Leu Glu Ile Leu Gln Asn
275 280 285

Gly Leu Tyr Leu Ile Tyr Gly Gln Val Ala Pro Asn Ala Asn Tyr Asn
290 295 300

Asp Val Ala Pro Phe Glu Val Arg Leu Tyr Lys Asn Lys Asp Met Ile
305 310 315 320

Gln Thr Leu Thr Asn Lys Ser Lys Ile Gln Asn Val Gly Gly Thr Tyr
325 330 335

Glu Leu His Val Gly Asp Thr Ile Asp Leu Ile Phe Asn Ser Glu His
340 345 350

Gln Val Leu Lys Asn Asn Thr Tyr Trp Gly Ile Ile Leu Leu Ala Asn
355 360 365

Pro Gln
370

<210> SEQ ID NO 48
<211> LENGTH: 358
<212> TYPE: PRT
<213> ORGANISM: Artificial Sequence
<220> FEATURE:
<223> OTHER INFORMATION: example of scGITRL-RBD

<400> SEQUENCE: 48

Gln Pro Cys Met Ala Lys Phe Gly Pro Leu Pro Ser Lys Trp Gln Met
1 5 10 15

Ala Ser Ser Glu Pro Pro Cys Val Asn Lys Val Ser Asp Trp Lys Leu
20 25 30

Glu Ile Leu Gln Asn Gly Leu Tyr Leu Ile Tyr Gly Gln Val Ala Pro
35 40 45

Asn Ala Asn Tyr Asn Asp Val Ala Pro Phe Glu Val Arg Leu Tyr Lys
50 55 60

Asn Lys Asp Met Ile Gln Thr Leu Thr Asn Lys Ser Lys Ile Gln Asn
65 70 75 80

Val Gly Gly Thr Tyr Glu Leu His Val Gly Asp Thr Ile Asp Leu Ile
85 90 95

Phe Asn Ser Glu His Gln Val Leu Lys Asn Asn Thr Tyr Trp Gly Ile
100 105 110

Ile Leu Leu Ala Gly Ser Gly Ser Gly Asn Gly Ser Pro Cys Met Ala
115 120 125

Lys Phe Gly Pro Leu Pro Ser Lys Trp Gln Met Ala Ser Ser Glu Pro
130 135 140

Pro Cys Val Asn Lys Val Ser Asp Trp Lys Leu Glu Ile Leu Gln Asn
145 150 155 160

Gly Leu Tyr Leu Ile Tyr Gly Gln Val Ala Pro Asn Ala Asn Tyr Asn
165 170 175

Asp Val Ala Pro Phe Glu Val Arg Leu Tyr Lys Asn Lys Asp Met Ile
180 185 190

Gln Thr Leu Thr Asn Lys Ser Lys Ile Gln Asn Val Gly Gly Thr Tyr
195 200 205

```
Glu Leu His Val Gly Asp Thr Ile Asp Leu Ile Phe Asn Ser Glu His
    210                 215                 220

Gln Val Leu Lys Asn Asn Thr Tyr Trp Gly Ile Ile Leu Leu Ala Gly
225                 230                 235                 240

Ser Gly Ser Pro Cys Met Ala Lys Phe Gly Pro Leu Pro Ser Lys Trp
                245                 250                 255

Gln Met Ala Ser Ser Glu Pro Pro Cys Val Asn Lys Val Ser Asp Trp
            260                 265                 270

Lys Leu Glu Ile Leu Gln Asn Gly Leu Tyr Leu Ile Tyr Gly Gln Val
        275                 280                 285

Ala Pro Asn Ala Asn Tyr Asn Asp Val Ala Pro Phe Glu Val Arg Leu
    290                 295                 300

Tyr Lys Asn Lys Asp Met Ile Gln Thr Leu Thr Asn Lys Ser Lys Ile
305                 310                 315                 320

Gln Asn Val Gly Gly Thr Tyr Glu Leu His Val Gly Asp Thr Ile Asp
                325                 330                 335

Leu Ile Phe Asn Ser Glu His Gln Val Leu Lys Asn Asn Thr Tyr Trp
            340                 345                 350

Gly Ile Ile Leu Leu Ala
        355


<210> SEQ ID NO 49
<211> LENGTH: 621
<212> TYPE: PRT
<213> ORGANISM: Artificial Sequence
<220> FEATURE:
<223> OTHER INFORMATION: example

<400> SEQUENCE: 49

Gln Pro Cys Met Ala Lys Phe Gly Pro Leu Pro Ser Lys Trp Gln Met
1               5                   10                  15

Ala Ser Ser Glu Pro Pro Cys Val Asn Lys Val Ser Asp Trp Lys Leu
            20                  25                  30

Glu Ile Leu Gln Asn Gly Leu Tyr Leu Ile Tyr Gly Gln Val Ala Pro
        35                  40                  45

Asn Ala Asn Tyr Asn Asp Val Ala Pro Phe Glu Val Arg Leu Tyr Lys
    50                  55                  60

Asn Lys Asp Met Ile Gln Thr Leu Thr Asn Lys Ser Lys Ile Gln Asn
65                  70                  75                  80

Val Gly Gly Thr Tyr Glu Leu His Val Gly Asp Thr Ile Asp Leu Ile
                85                  90                  95

Phe Asn Ser Glu His Gln Val Leu Lys Asn Asn Thr Tyr Trp Gly Ile
            100                 105                 110

Ile Leu Leu Ala Asn Pro Gln Phe Ile Ser Gly Ser Gly Ser Gly Asn
        115                 120                 125

Gly Ser Glu Pro Cys Met Ala Lys Phe Gly Pro Leu Pro Ser Lys Trp
    130                 135                 140

Gln Met Ala Ser Ser Glu Pro Pro Cys Val Asn Lys Val Ser Asp Trp
145                 150                 155                 160

Lys Leu Glu Ile Leu Gln Asn Gly Leu Tyr Leu Ile Tyr Gly Gln Val
                165                 170                 175

Ala Pro Asn Ala Asn Tyr Asn Asp Val Ala Pro Phe Glu Val Arg Leu
            180                 185                 190

Tyr Lys Asn Lys Asp Met Ile Gln Thr Leu Thr Asn Lys Ser Lys Ile
        195                 200                 205
```

```
Gln Asn Val Gly Gly Thr Tyr Glu Leu His Val Gly Asp Thr Ile Asp
    210                 215                 220

Leu Ile Phe Asn Ser Glu His Gln Val Leu Lys Asn Asn Thr Tyr Trp
225                 230                 235                 240

Gly Ile Ile Leu Leu Ala Asn Pro Gln Phe Ile Ser Gly Ser Gly Ser
                245                 250                 255

Gly Asn Gly Ser Glu Pro Cys Met Ala Lys Phe Gly Pro Leu Pro Ser
            260                 265                 270

Lys Trp Gln Met Ala Ser Ser Glu Pro Pro Cys Val Asn Lys Val Ser
        275                 280                 285

Asp Trp Lys Leu Glu Ile Leu Gln Asn Gly Leu Tyr Leu Ile Tyr Gly
    290                 295                 300

Gln Val Ala Pro Asn Ala Asn Tyr Asn Asp Val Ala Pro Phe Glu Val
305                 310                 315                 320

Arg Leu Tyr Lys Asn Lys Asp Met Ile Gln Thr Leu Thr Asn Lys Ser
                325                 330                 335

Lys Ile Gln Asn Val Gly Gly Thr Tyr Glu Leu His Val Gly Asp Thr
            340                 345                 350

Ile Asp Leu Ile Phe Asn Ser Glu His Gln Val Leu Lys Asn Asn Thr
        355                 360                 365

Tyr Trp Gly Ile Ile Leu Leu Ala Asn Pro Gln Phe Ile Ser Gly Ser
    370                 375                 380

Ser Ser Ser Ser Ser Ser Ser Gly Ser Cys Asp Lys Thr His Thr Cys
385                 390                 395                 400

Pro Pro Cys Pro Ala Pro Glu Leu Leu Gly Gly Pro Ser Val Phe Leu
                405                 410                 415

Phe Pro Pro Lys Pro Lys Asp Thr Leu Met Ile Ser Arg Thr Pro Glu
            420                 425                 430

Val Thr Cys Val Val Val Asp Val Ser His Glu Asp Pro Glu Val Lys
        435                 440                 445

Phe Asn Trp Tyr Val Asp Gly Val Glu Val His Asn Ala Lys Thr Lys
    450                 455                 460

Pro Arg Glu Glu Gln Tyr Ser Ser Thr Tyr Arg Val Val Ser Val Leu
465                 470                 475                 480

Thr Val Leu His Gln Asp Trp Leu Asn Gly Lys Glu Tyr Lys Cys Lys
                485                 490                 495

Val Ser Asn Lys Ala Leu Pro Ala Pro Ile Glu Lys Thr Ile Ser Lys
            500                 505                 510

Ala Lys Gly Gln Pro Arg Glu Pro Gln Val Tyr Thr Leu Pro Pro Ser
        515                 520                 525

Arg Glu Glu Met Thr Lys Asn Gln Val Ser Leu Thr Cys Leu Val Lys
    530                 535                 540

Gly Phe Tyr Pro Ser Asp Ile Ala Val Glu Trp Glu Ser Asn Gly Gln
545                 550                 555                 560

Pro Glu Asn Asn Tyr Lys Thr Thr Pro Pro Val Leu Asp Ser Asp Gly
                565                 570                 575

Ser Phe Phe Leu Tyr Ser Lys Leu Thr Val Asp Lys Ser Arg Trp Gln
            580                 585                 590

Gln Gly Asn Val Phe Ser Cys Ser Val Met His Glu Ala Leu His Asn
        595                 600                 605

His Tyr Thr Gln Lys Ser Leu Ser Leu Ser Pro Gly Lys
    610                 615                 620
```

<210> SEQ ID NO 50
<211> LENGTH: 597
<212> TYPE: PRT
<213> ORGANISM: Artificial Sequence
<220> FEATURE:
<223> OTHER INFORMATION: example

<400> SEQUENCE: 50

Gln Pro Cys Met Ala Lys Phe Gly Pro Leu Pro Ser Lys Trp Gln Met
1               5                   10                  15

Ala Ser Ser Glu Pro Pro Cys Val Asn Lys Val Ser Asp Trp Lys Leu
            20                  25                  30

Glu Ile Leu Gln Asn Gly Leu Tyr Leu Ile Tyr Gly Gln Val Ala Pro
        35                  40                  45

Asn Ala Asn Tyr Asn Asp Val Ala Pro Phe Glu Val Arg Leu Tyr Lys
    50                  55                  60

Asn Lys Asp Met Ile Gln Thr Leu Thr Asn Lys Ser Lys Ile Gln Asn
65                  70                  75                  80

Val Gly Gly Thr Tyr Glu Leu His Val Gly Asp Thr Ile Asp Leu Ile
                85                  90                  95

Phe Asn Ser Glu His Gln Val Leu Lys Asn Asn Thr Tyr Trp Gly Ile
            100                 105                 110

Ile Leu Leu Ala Gly Ser Gly Ser Gly Asn Gly Ser Pro Cys Met Ala
        115                 120                 125

Lys Phe Gly Pro Leu Pro Ser Lys Trp Gln Met Ala Ser Ser Glu Pro
    130                 135                 140

Pro Cys Val Asn Lys Val Ser Asp Trp Lys Leu Glu Ile Leu Gln Asn
145                 150                 155                 160

Gly Leu Tyr Leu Ile Tyr Gly Gln Val Ala Pro Asn Ala Asn Tyr Asn
                165                 170                 175

Asp Val Ala Pro Phe Glu Val Arg Leu Tyr Lys Asn Lys Asp Met Ile
            180                 185                 190

Gln Thr Leu Thr Asn Lys Ser Lys Ile Gln Asn Val Gly Gly Thr Tyr
        195                 200                 205

Glu Leu His Val Gly Asp Thr Ile Asp Leu Ile Phe Asn Ser Glu His
    210                 215                 220

Gln Val Leu Lys Asn Asn Thr Tyr Trp Gly Ile Ile Leu Leu Ala Gly
225                 230                 235                 240

Ser Gly Ser Pro Cys Met Ala Lys Phe Gly Pro Leu Pro Ser Lys Trp
                245                 250                 255

Gln Met Ala Ser Ser Glu Pro Pro Cys Val Asn Lys Val Ser Asp Trp
            260                 265                 270

Lys Leu Glu Ile Leu Gln Asn Gly Leu Tyr Leu Ile Tyr Gly Gln Val
        275                 280                 285

Ala Pro Asn Ala Asn Tyr Asn Asp Val Ala Pro Phe Glu Val Arg Leu
    290                 295                 300

Tyr Lys Asn Lys Asp Met Ile Gln Thr Leu Thr Asn Lys Ser Lys Ile
305                 310                 315                 320

Gln Asn Val Gly Gly Thr Tyr Glu Leu His Val Gly Asp Thr Ile Asp
                325                 330                 335

Leu Ile Phe Asn Ser Glu His Gln Val Leu Lys Asn Asn Thr Tyr Trp
            340                 345                 350

Gly Ile Ile Leu Leu Ala Gly Ser Ser Ser Ser Ser Ser Ser Ser Gly
        355                 360                 365

-continued

| | | | | | | | | | | | | | | | |
|---|---|---|---|---|---|---|---|---|---|---|---|---|---|---|---|
| Ser | Cys | Asp | Lys | Thr | His | Thr | Cys | Pro | Pro | Cys | Pro | Ala | Pro | Glu | Leu |
| | 370 | | | | | 375 | | | | | 380 | | | | |
| Leu | Gly | Gly | Pro | Ser | Val | Phe | Leu | Phe | Pro | Pro | Lys | Pro | Lys | Asp | Thr |
| 385 | | | | | 390 | | | | | 395 | | | | | 400 |
| Leu | Met | Ile | Ser | Arg | Thr | Pro | Glu | Val | Thr | Cys | Val | Val | Val | Asp | Val |
| | | | | 405 | | | | | 410 | | | | | 415 | |
| Ser | His | Glu | Asp | Pro | Glu | Val | Lys | Phe | Asn | Trp | Tyr | Val | Asp | Gly | Val |
| | | | 420 | | | | | 425 | | | | | 430 | | |
| Glu | Val | His | Asn | Ala | Lys | Thr | Lys | Pro | Arg | Glu | Glu | Gln | Tyr | Ser | Ser |
| | | 435 | | | | | 440 | | | | | 445 | | | |
| Thr | Tyr | Arg | Val | Val | Ser | Val | Leu | Thr | Val | Leu | His | Gln | Asp | Trp | Leu |
| | 450 | | | | | 455 | | | | | 460 | | | | |
| Asn | Gly | Lys | Glu | Tyr | Lys | Cys | Lys | Val | Ser | Asn | Lys | Ala | Leu | Pro | Ala |
| 465 | | | | | 470 | | | | | 475 | | | | | 480 |
| Pro | Ile | Glu | Lys | Thr | Ile | Ser | Lys | Ala | Lys | Gly | Gln | Pro | Arg | Glu | Pro |
| | | | | 485 | | | | | 490 | | | | | 495 | |
| Gln | Val | Tyr | Thr | Leu | Pro | Pro | Ser | Arg | Glu | Glu | Met | Thr | Lys | Asn | Gln |
| | | | 500 | | | | | 505 | | | | | 510 | | |
| Val | Ser | Leu | Thr | Cys | Leu | Val | Lys | Gly | Phe | Tyr | Pro | Ser | Asp | Ile | Ala |
| | | 515 | | | | | 520 | | | | | 525 | | | |
| Val | Glu | Trp | Glu | Ser | Asn | Gly | Gln | Pro | Glu | Asn | Asn | Tyr | Lys | Thr | Thr |
| | 530 | | | | | 535 | | | | | 540 | | | | |
| Pro | Pro | Val | Leu | Asp | Ser | Asp | Gly | Ser | Phe | Phe | Leu | Tyr | Ser | Lys | Leu |
| 545 | | | | | 550 | | | | | 555 | | | | | 560 |
| Thr | Val | Asp | Lys | Ser | Arg | Trp | Gln | Gln | Gly | Asn | Val | Phe | Ser | Cys | Ser |
| | | | | 565 | | | | | 570 | | | | | 575 | |
| Val | Met | His | Glu | Ala | Leu | His | Asn | His | Tyr | Thr | Gln | Lys | Ser | Leu | Ser |
| | | | 580 | | | | | 585 | | | | | 590 | | |
| Leu | Ser | Pro | Gly | Lys | | | | | | | | | | | |
| | | 595 | | | | | | | | | | | | | |

SINGLE-CHAIN GLUCOCORTICOID-INDUCED TUMOR NECROSIS FACTOR RECEPTOR (GITR) RECEPTOR AGONIST PROTEINS

This application is a continuation of U.S. application Ser. No. 15/957,279, filed Apr. 19, 2018, now U.S. Pat. No. 10,533,043; which is a continuation of PCT/EP2016/075552, filed Oct. 24, 2016; which claims priority to U.S. Provisional Application No. 62/245,815, filed Oct. 23, 2015. The contents of the above applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence_Listing.txt with a creation date of Apr. 11, 2018, and a size of 121 kilobytes. The Sequence Listing filed via EFS-Web is part of the specification and is hereby incorporated in its entirety by reference herein.

FIELD OF THE INVENTION

The present invention provides specific GITR receptor agonist proteins comprising three soluble GITRL domains and an Fc fragment, nucleic acid molecules encoding the GITR receptor agonist proteins, and uses thereof. The GITR receptor agonist proteins are substantially non-aggregating and suitable for therapeutic, diagnostic and/or research applications.

BACKGROUND OF THE INVENTION

It is known that trimerization of TNF superfamily (TNFSF) cytokines is required for efficient receptor binding and activation. Trimeric complexes of TNF superfamily cytokines, however, are difficult to prepare from recombinant monomeric units. WO 01/49866 and WO 02/09055 disclose recombinant fusion proteins comprising a TNF cytokine and a multimerization component, particularly a protein from the C1q protein family or a collectin. A disadvantage of these fusion proteins is, however, that the trimerization domain usually has a large molecular weight and/or that the trimerization is rather inefficient.

Schneider et al. (J Exp Med 187 (1989), 1205-1213) describe that trimers of TNF cytokines are stabilized by N-terminally positioned stabilization motifs. In CD95L, the stabilization of the receptor binding domain trimer is presumably caused by N-terminal amino acid domains which are located near the cytoplasmic membrane.

Shiraishi et al. (Biochem Biophys Res Commun 322 (2004), 197-202) describe that the receptor binding domain of CD95L may be stabilized by N-terminally positioned artificial α-helical coiled-coil (leucine zipper) motifs. It was found, however, that the orientation of the polypeptide chains to each other, e.g. parallel or antiparallel orientation, can hardly be predicted. Further, the optimal number of heptad-repeats in the coiled-coil zipper motif are difficult to determine. In addition, coiled-coil structures have the tendency to form macromolecular aggregates after alteration of pH and/or ionic strength.

WO 01/25277 relates to single-chain oligomeric polypeptides which bind to an extracellular ligand binding domain of a cellular receptor, wherein the polypeptide comprises at least three receptor binding sites of which at least one is capable of binding to a ligand binding domain of the cellular receptor and at least one is incapable of effectively binding to a ligand binding domain of the cellular receptor, whereby the single-chain oligomeric polypeptides are capable of binding to the receptor, but incapable of activating the receptor. For example, the monomers are derived from cytokine ligands of the TNF family, particularly from TNF-α.

WO 2005/103077 discloses single-chain fusion polypeptides comprising at least three monomers of a TNF family ligand member and at least two peptide linkers that link the monomers of the TNF ligand family members to one another. Recent experiments, however, have shown that these single-chain fusion polypeptides show undesired aggregation.

WO 2010/010051 discloses single-chain fusion polypeptides comprising three soluble TNF family cytokine domains and at least two peptide linkers. The described fusion polypeptides are substantially non-aggregating.

Recent studies have shown that the in vivo anti-tumor activity of an anti-GITR-mAb is dependent on Fc-gamma-R driven mechanisms and does not rely on agonistic activity only. Bulliard, Y., R. Jolicoeur, M. Windman, S. M. Rue, S. Ettenberg, D. A. Knee, N. S. Wilson, G. Dranoff and J. L. Brogdon (2013). "Activating Fc gamma receptors contribute to the antitumor activities of immunoregulatory receptor-targeting antibodies." J Exp Med 210(9): 1685-1693.

There is a need in the art for novel GITR receptor agonists that exhibit high biological activity independent of Fc-gamma-R based crosslinking in vivo, high stability, and allow for efficient recombinant manufacturing.

SUMMARY OF THE INVENTION

The present invention provides specific GITR receptor agonist proteins that mimic the GITR:GITRL interaction in vivo, exhibit low proteolytic degradation and a shorter in vivo half-life as compared to agonistic monoclonal antibodies.

The GITR receptor agonist proteins of the instant invention generally comprise: (i) a first soluble GITRL cytokine domain; (ii) a first peptide linker; (iii) a second soluble GITRL domain; (iv) a second peptide linker; (v) a third soluble GITRL domain; (vi) a third peptide linker (e.g., a hinge-linker) and (vii) an antibody Fc fragment.

In one embodiment, the antibody Fc fragment (vii) is located N terminal to the first GITRL domain (i) and/or C-terminal to the third GITRL domain (v). In another embodiment the antibody Fc fragment is located C-terminally to the third GITRL domain (v). In one embodiment, the polypeptide is substantially non-aggregating. In another embodiment, the second and/or third soluble GITRL domain is an N-terminally shortened domain which optionally comprises amino acid sequence mutations. In another embodiment, the soluble GITRL domains (i), (ii) and (iii) are an C-terminally shortened domain which optionally comprises amino acid sequence mutations.

In one embodiment, at least one of the soluble GITRL domains, particularly at least one of the soluble GITRL domains (iii) and (v), is a soluble GITRL domain with an N-terminal sequence which starts at amino acid E52 or A54 or K55 or E56 or P57 of human GITRL and wherein E52 or A54 or K55 or E56 may be replaced by a neutral amino acid, e.g., Ser or Gly. In another embodiment, at least one of the soluble GITRL domains, particularly at least one of the soluble GITRL domains (iii) and (v), is a soluble GITRL domain with an N-terminal sequences selected from (a) E52-P57 and (b) (Gly/Ser)56-P57. In one embodiment, the soluble GITRL domain ends with amino acid S177 of human GITRL and/or optionally comprises one or more mutation at positions E52, A54, K55, L65A, P66A, K68A, P77, N80, V82, E88, L90, Q91, N106, N120, N129, K121, D122, V144, L159, N161, N172, P173, Q174. In one embodiment, the soluble GITRL domains (i), (iii) and (v) comprise amino acids E52-S177 of human GITRL according to SEQ ID NO: 1.

In one embodiment, at least one of the soluble GITRL domains, particularly at least the soluble GITRL domains (i), is a soluble GITRL domain with an N-terminal sequence which starts at amino acid E56 and wherein E56 may be replaced by Gln, Ser or Gly. In one embodiment, at least one of the soluble GITRL domains, particularly at least the soluble GITRL domain (iii), is a soluble C-terminal shortened GITRL domain ending with A170. In another embodiment, at least one of the soluble GITRL domains, particularly at least the soluble GITRL domains (iii), is a soluble C-terminal shortened GITRL domain ending with P171. In still another embodiment, at least one of the soluble GITRL domains, particularly at least the soluble GITRL domains (iii), is a soluble C-terminal shortened GITRL domain ending with Q174.

In one embodiment, the first and second peptide linkers (ii) and (iv) independently have a length of 3-8 amino acids, particularly a length of 3, 4, 5, 6, 7, or 8 amino acids, and preferably are glycine/serine linkers, optionally comprising an asparagine residue which may be glycosylated. In one embodiment, the first and the second peptide linkers (ii) and (iv) consist of the amino acid sequence according to SEQ ID NO: 2. In another embodiment, the polypeptide additionally comprises an N-terminal signal peptide domain, e.g., of SEQ ID NO: 17, which may comprise a protease cleavage site, and/or which additionally comprises a C-terminal element which may comprise and/or connect to a recognition/purification domain, e.g., a Strep-tag attached to a serine linker according to SEQ ID NO: 18.

In one embodiment, the antibody Fc fragment (vii) is fused to the soluble GITRL domain (i) and/or (v) via a hinge-linker, preferably of SEQ ID NO: 16. In another embodiment, the antibody Fc fragment (vii) consists of the amino acid sequence as shown in SEQ ID NO: 13 or 14.

In one embodiment, the single-chain fusion polypeptide of the present invention comprises the amino acid sequence selected from the group consisting of SEQ ID NO: 15, and 25-35.

In one embodiment, the present invention provides a GITR receptor agonist protein comprising a dimer of two single-chain fusion polypeptides each having the amino acid sequence set forth in SEQ ID NO: 27. In one embodiment, the two polypeptides are covalently linked through three interchain disulfide bonds formed between cysteine residues 406, 412, and 415 of each polypeptide. Similar cysteine residues are positions 406, 412 and 415 of SEQ ID NO: 28, 29 or 30, positions 392, 398 and 401 of SEQ ID NO: 31, positions 391, 397 and 400 of SEQ ID NO: 32, positions 374, 380 and 383 of SEQ ID NO: 33, positions 397, 403 and 406 of SEQ ID NO: 34 and positions 382, 388 and 391 of SEQ ID NO: 35.

In one embodiment, one or more of the asparagine residues at positions 132 and 266 of the mature polypeptide(s) SEQ ID NO: 27, 28, 29 or 30 are N-glycosylated. In another embodiment, the asparagine residues at positions 132 and 266 of the polypeptide(s) are both N-glycosylated. Similar asparagine residues are positions 128 and 257 of SEQ ID NO: 31, positions 128 and 258 of SEQ ID NO: 32, positions 122 and 245 of SEQ ID NO: 33, positions 129 and 260 of SEQ ID NO: 34 and positions 125 and 250 of SEQ ID NO: 35.

In another embodiment, the polypeptide(s) are further post-translationally modified. In another embodiment, the post-translational modification comprises the N-terminal glutamine of the E52Q mutein of the first soluble domain (i) modified to pyroglutamate. In still another embodiment, the post-translational modification comprises the N-terminal glutamine of the E56Q mutein of the first soluble domain (i) modified to pyroglutamate.

■ ■ ■ Cell membrane, N-terminus located within the cell, 1. anti-parallel β-fold of receptor-binding domain (RBD),
2. interface of RBD and cell membrane,
3. protease cleavage site.

Figure 1:
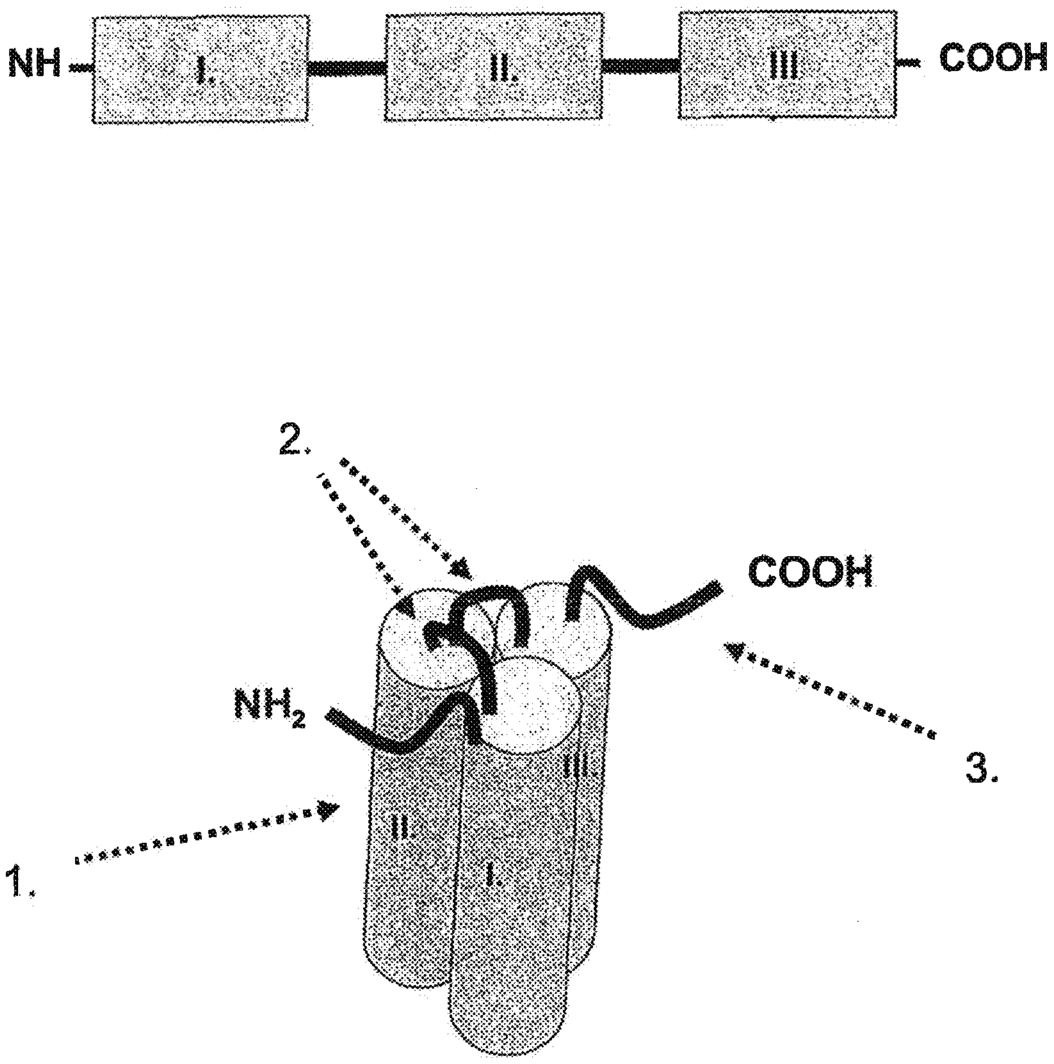
FIG. 1 Domain structure of a single-chain fusion polypeptide comprising three GITRL domains. I., II., III. Soluble GITRL domains.
Figure 2:
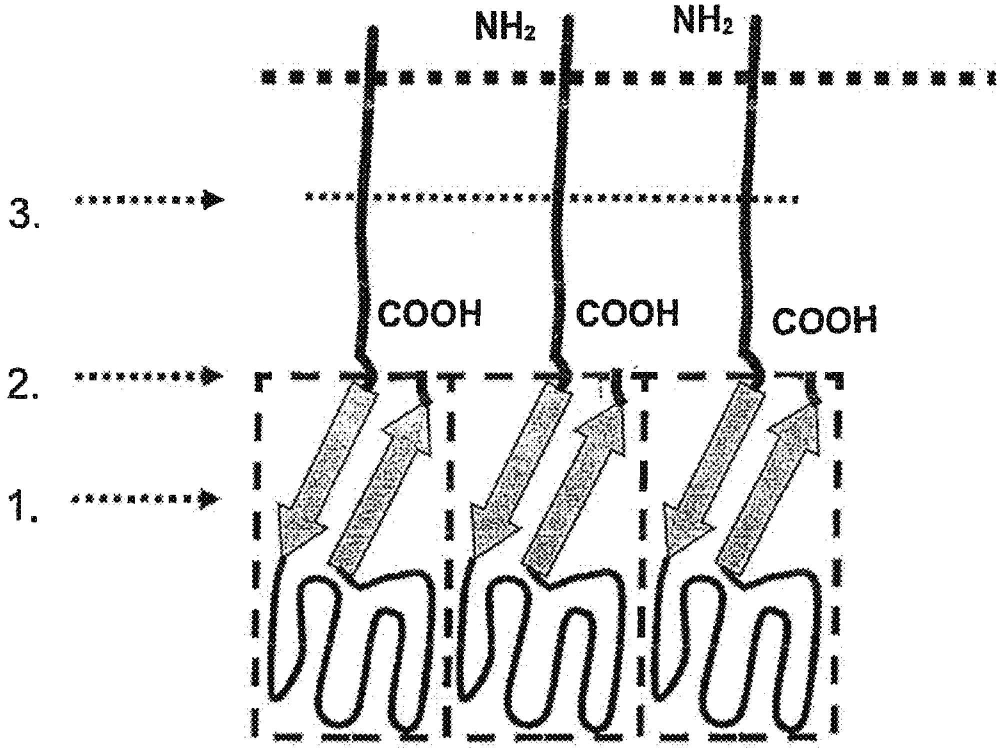
FIG. 2 Schematic picture representing the general structure of GITRL.
Figure 3:
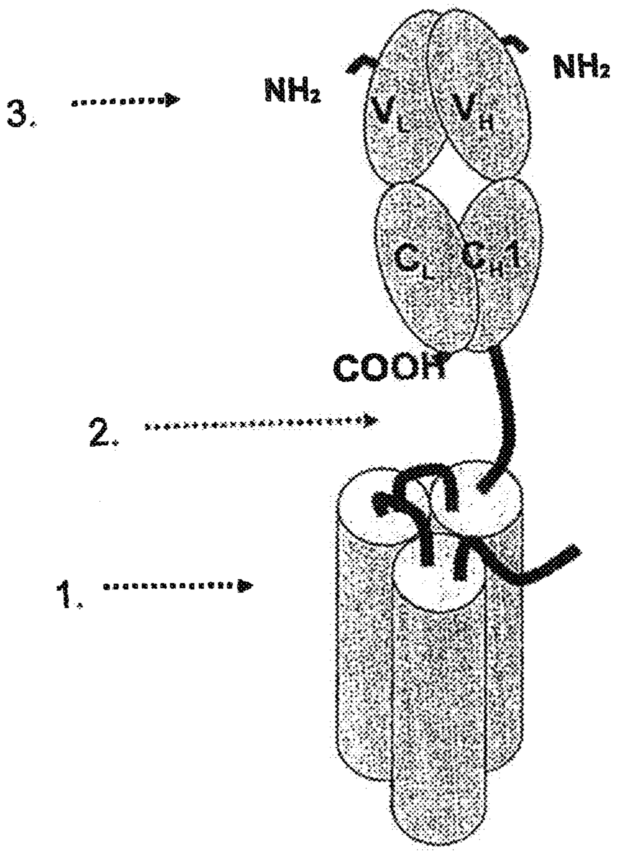

FIG. 3 Single-chain fusion polypeptide comprising an additional Fab antibody fragment.

Figure 4:
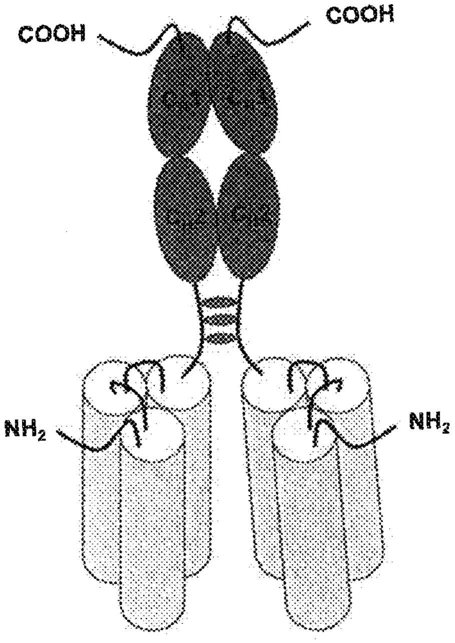

FIG. 4 Dimerization of two C-terminally fused single-chain Fc fusion polypeptides via three disulfide bridges.

Figure 5:
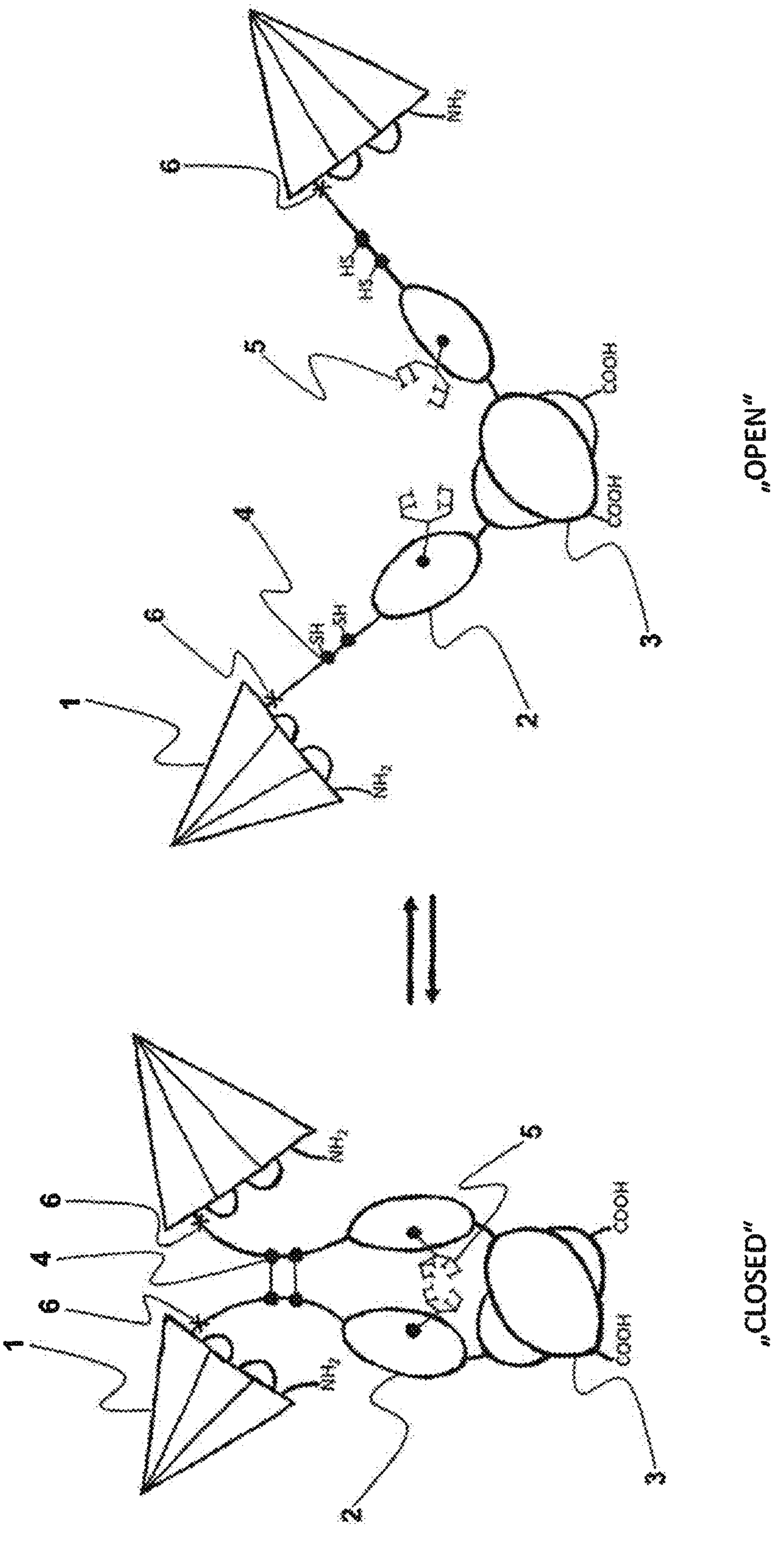

FIG. 5 Schematic representation of the hexavalent single chain CD27 receptor agonist fusion protein of the invention. CH2-Carbohydrates (5) present on the inner surface areas normally shield the CH2-subdomain sterically (2) from proteases during "open Fc-conformation transits" wherein hinge-interchain disulfide bonds (4) are reduced and the covalent interchain linkage is disrupted. This enables CH2-dissociation and exposure of the inner surface areas and the upper hinge lysine K223 (6) towards proteases. Dimer association in the "open stage" remains intact due to the high affinity of the CH3 domains (3) to each other.

(1) scCD27L-RBD; (2) CH2 domain; (3) CH3 domain; (4) Hinge-Cysteines (left side: oxidized to disulfid-bridges; right side reduced stage with free thiols); (5) CH2-Carbohydrates attached to N297 position (EU-numbering); (6) Upper Hinge Lysine (K223)

Figure 6:
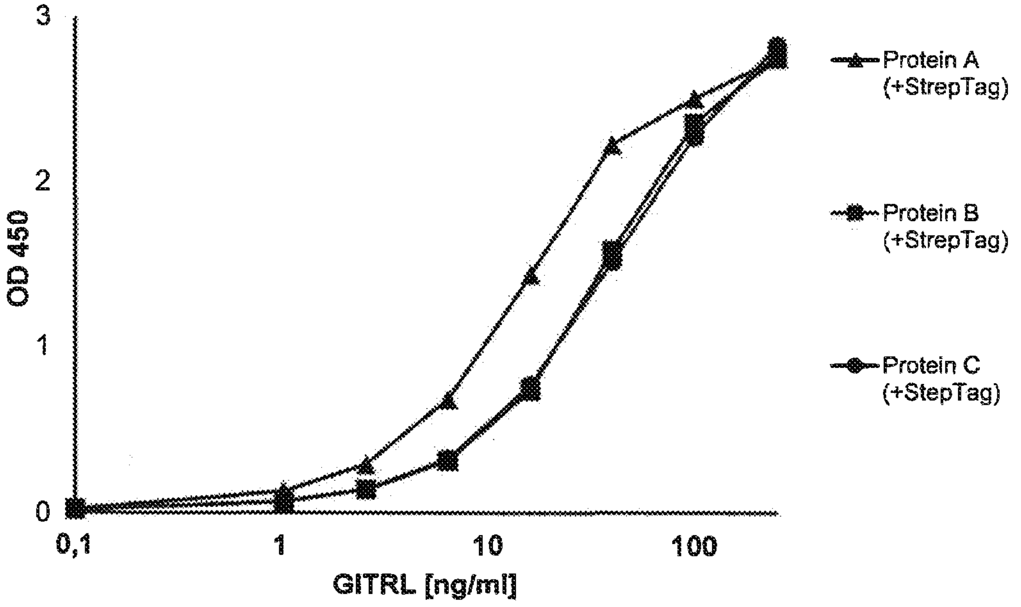

FIG. 6 ELISA assessing the binding of three different GITR receptor agonist proteins, Protein A, Protein B and Protein C (each one including a strep tag), to their receptor.

Figure 7:
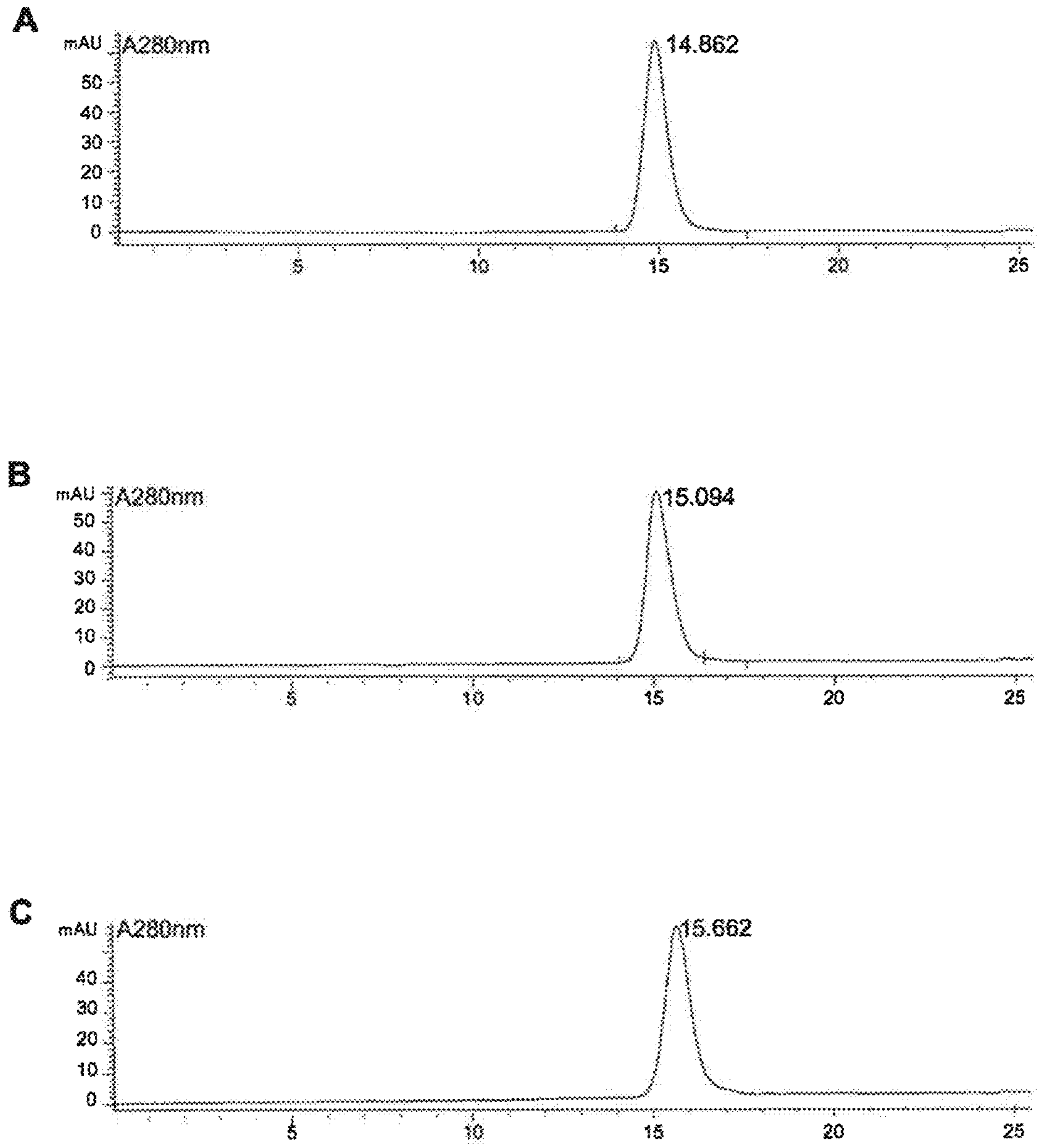

FIG. 7 Depicts an analytical size exclusion chromatography of strep tagged Protein A, Protein B and Protein C. Experiment performed on a 1260 Infinity HPLC system using a Tosoh TSKgelG3000SWxl column. The column was loaded with respective protein at a concentration of 1 mg/ml in a total volume of 20 μl. The flow rate was set to 0.5 ml/min.

Figure 8:
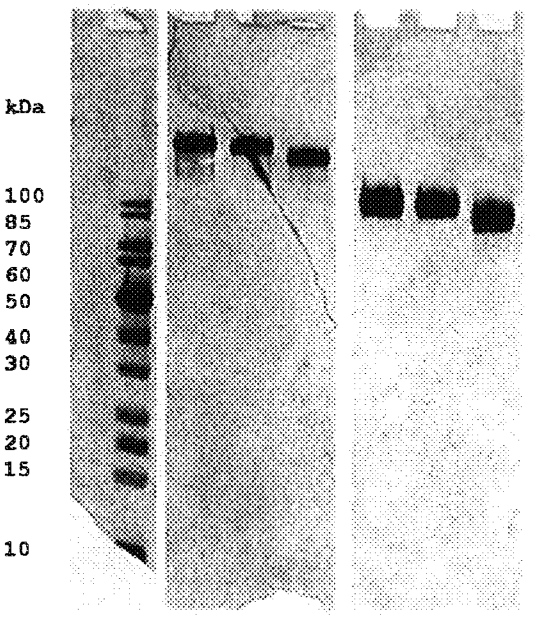

(A) For Protein A a single main peak at 14.86 min. was observed. (B) For Protein B a single main peak at 15.09 min. was observed. (C) For Protein C a single peak at 15.56 min. was observed FIG. 8 Depicts SDS-PAGE results of Protein A, Protein B and Protein C under non-reducing and reducing conditions. 240 ng of respective protein were loaded on an SDS-PAGE 4-12% Bis-Tris gel under non-reducing (lane 2-4) or reducing (lane 5-7) conditions containing DTT as reducing agent. Gels were run at 110V for 20 min followed by 190V for 60 min and were subsequently stained using a silver-stain protocol. One observes a molecular weight difference between the main bands in lanes 2-4 and lanes 5-7 of about 70-80 kDa. As this is about half the molecular weight as observed for the main band in lanes 2-4, this indicates that the homodimer in lanes 2-4 is covalently linked by disulfide bridges. The bonds are lost under reducing conditions in lanes 5-7.

DETAILED DESCRIPTION OF THE INVENTION

The present invention provides a single-chain fusion polypeptide comprising at least three soluble GITRL domains connected by two peptide linkers and N-terminally and/or C-terminally an antibody-derived dimerization domain. The inventors have discovered that dimerization of the two single-chain fusion polypeptides through the dimerization domain results in a hexavalent GITR receptor agonist, which provides high biological activity and good stability.

Preferably, the single-chain fusion polypeptide is non-aggregating. The term "non-aggregating" refers to a monomer content of the preparation of 50%, preferably 70% and more preferably 90%. The ratio of monomer content to aggregate content may be determined by examining the amount of aggregate formation using size-exclusion chromatography (SEC). The stability concerning aggregation may be determined by SEC after defined time periods, e.g. from a few to several days, to weeks and months under different storage conditions, e.g. at 4° C. or 25° C. For the fusion protein, in order to be classified as substantially non-aggregating, it is preferred that the "monomer" content is as defined above after a time period of several days, e.g. 10 days, more preferably after several weeks, e.g. 2, 3 or 4 weeks, and most preferably after several months, e.g. 2 or 3 months of storage at 4° C., or 25° C. With regard to the definition of "monomer" in the case of FC-fusion proteins, the assembly of two polypeptide chains is driven by the FC-part and the functional unit of the resulting assembled protein consists of two chains. This unit is defined as "monomer" in the case of Fc-fusion proteins regardless of being a dimerized single-chain fusion polypeptide.

The single-chain fusion polypeptide may comprise additional domains which may be located at the N- and/or C-termini thereof. Examples for additional fusion domains are e.g. an N-terminal signal peptide domain which may comprise a protease cleave site or a C-terminal element which may comprise and/or connect to a recognition/purification domain. According to a preferred embodiment, the fusion polypeptide comprises a Strep-tag at its C-terminus that is fused via a linker. An exemplary Strep-tag including a short serine linker is shown in SEQ ID NO: 18.

The GITR receptor agonist protein of the present invention comprises three soluble domains derived from GITRL. Preferably, those soluble domains are derived from a mammalian, particularly human GITRL including allelic variants and/or derivatives thereof. The soluble domains comprise the extracellular portion of GITRL including the receptor binding domain without membrane located domains. Like other proteins of the TNF superfamily, GITRL is anchored to the membrane via an N-terminal portion of 15-30 amino acids, the so-called stalk-region. The stalk region contributes to trimerization and provides a certain distance to the cell membrane. However, the stalk region is not part of the trimeric receptor binding domain (RBD) with the receptor binding sites located at the protomer interfaces.

Importantly, the RBD is characterized by a particular localization of its N- and C-terminal amino acids. Said amino acids are immediately adjacent and are located in close proximity to the axis of the trimer. The first N-terminal amino acids of the RBD (starting with Pro57 in the case of human GITRL) form an anti-parallel beta-strand with a C-terminal region of the RBD ending in the case of human GITRL with Ala171. Human GITRL contains a C-terminal extension (N172-S177) potentially involved in weak protomer contacts protruding into the interprotomer interface. The C-terminal Ser177 still is in close proximity to Pro57 of the neighboring protomer.

Thus, the aforementioned anti-parallel beta-strand of the RBD and the C-terminal extension form an interface with the cell membrane, which is connected to and anchored within the cell membrane via the amino acids of the stalk region. It is highly preferred that the soluble GITRL domains of the GITR receptor agonist protein comprise a receptor binding domain of the GITRL lacking any amino acids from the stalk region. Otherwise, a long linker connecting the C-terminus of one of the soluble domains with the N-terminus of the next soluble domain would be required to compensate for the N-terminal stalk-region of the next soluble domain, which might result in instability and/or formation of aggregates.

A further advantage of such soluble domains is that the N-terminal amino acids of the RBD are not accessible for any anti-drug antibodies. Preferably, the single-chain fusion polypeptide consisting of (i) a first soluble GITRL domain; (ii) a first peptide linker; (iii) a second soluble GITRL domain; (iv) a second peptide linker; (v) a third soluble GITRL domain is capable of forming an ordered structure mimicking the trimeric organization of its natural counterpart thereby comprising at least one functional binding site for the respective GITRL receptor. The single-chain fusion polypeptide comprising components (i)-(v) is therefore also termed single-chain-GITRL-receptor-binding-domain (scGITRL-RBD). Importantly, compared to homotrimeric wild type GITRL-RBD, the scGITRL-RBD comprises an enhanced stability as the soluble GITRL domains (i), (iii) and (v) are enforced to trimerize by the covalent linkage to each other provided by the linkers (ii) and (iv).

The GITR receptor agonist protein comprises three functional GITR receptor binding sites, i.e. amino acid sequences capable of forming a complex with a GITR receptor. Thus, the soluble domains are capable of binding to the corresponding GITR receptor. In one embodiment, at least one of the soluble domains is capable of receptor activation, whereby apoptotic and/or proliferative activity may be affected. In a further embodiment, one or more of the soluble domains are selected as not being capable of receptor activation.

The soluble GITRL domain may be derived from human GITRL as shown in SEQ ID NO: 1. Preferably, the soluble GITRL domains are derived from human GITRL, particularly starting from amino acids 52, 56 or 57 and comprise particularly amino acids 52-177 or 56-177 or 57-177 of SEQ ID NO: 1. Optionally, amino acid Glu56 of SEQ ID NO: 1 may be replaced by a non-charged amino acid, e.g. Ser or Gly or is replaced by Glutamine.

TABLE 1

Sequence of Wild-Type Human GITRL Protein

| SEQ ID NO | Sequence |
|---|---|
| 1 | MCLSHLENMPLSHSRTQGAQRSSWKLWLFCSIVMLLFLCS FSWLIFIFLQLETAKEPCMAKFGPLPSKWQMASSEPPCVN KVSdWKLEILQNGLYLIYGQVAPNANYNDVAPFEVRLYKN KDMIQTLTNKSKIQNVGGTYELHVGDTIDLIFNSEHQVLK NNTYWGIILLANPQFIS |

As indicated above, the soluble GITRL domains may comprise the wild-type sequences as indicated in SEQ ID NO: 1. It should be noted, however, that it is possible to introduce mutations in one or more of these soluble domains, e.g. mutations which alter (e.g. increase or decrease) the binding properties of the soluble domains. In one embodiment, soluble domains that cannot bind to the corresponding cytokine receptor can be selected.

In a further embodiment of the invention, the soluble GITRL domain (i) comprises a mutant of GITRL or a receptor binding domain thereof resulting in reduced affinity and/or reduced activation of GITR receptor.

GITRL-Muteins Affecting Receptor Binding and/or Activity

The mutant may be generated by any technique known by a skilled person. The substitution may affect at least one amino acid of GITRL, e.g., human GITRL (e.g., SEQ ID NO: 1) or a receptor binding domain thereof as described herein. Preferred substitutions in this regard affect at least one of the following amino acids of human GITRL of SEQ ID NO: 1: L65A, P66A, K68A, P77, N80, V82, E88, L90, Q91, N106, N120, N129, K121, D122, V144, L159, N161, N172, P173, and Q174. In a preferred embodiment N106 is mutated to A, S, R, D, E, Q or N and/or D122 is mutated to A, S, D, E or R.

In another preferred embodiment, the C-terminal region Q174-S177 is deleted from at least one of the soluble domains (i), (III) or (v).

The amino acid substitution(s) may affect the binding and/or activity of GITRL, e.g., human GITRL, to or on either the GITR binding or the GITR induced signaling. The binding and/or activity of the GITR may be affected positively, i.e., stronger, more selective or more specific binding and/or more activation of the receptor. Alternatively, the binding and/or activity of the GITR may be affected negatively, i.e., weaker, less selective or less specific binding and/or less or no activation of the receptor.

Thus one embodiment is a GITR receptor agonist protein as described herein wherein at least one of the soluble domains comprises a mutant of GITRL or a receptor binding domain thereof which binds and/or activates GITR to a lesser extent than the wildtype-GITRL.

GITRL-Muteins with Enhanced Stability/Solubility

In a further embodiment of the invention, one or more of the soluble GITRL domains (i), (iii), and (v) may comprise a mutant of GITRL or a receptor binding domain thereof resulting in reduced self-aggregation and/or prolonged in vivo stability. Preferred substitutions in this regard are V82[S, T], E88D and N129 [S, D]. The mutation(s) of each GITRL domain may be the same or different.

The single-chain fusion molecule of the present invention comprises three soluble GITRL domains, namely components (i), (iii) and (v). The stability of a single-chain GITRL fusion polypeptide against aggregation is enhanced, if the second and/or third soluble GITRL domain is an N-terminally shortened domain which optionally comprises amino acid sequence mutations. Thus, preferably, both the second and the third soluble GITRL domain are N-terminally shortened domains which optionally comprise amino acid sequence mutations in the N-terminal regions, preferably within the first five amino acids of the N-terminus of the soluble GITRL domain. These mutations may comprise replacement of basic amino acids, by neutral amino acids, particularly serine or glycine.

In contrast thereto, the selection of the first soluble GITRL domain is not as critical. Here, a soluble domain having a full-length N-terminal sequence may be used. It should be noted, however, that also the first soluble GITRL domain may have an N-terminally shortened and optionally mutated sequence.

In a further preferred embodiment of the present invention, the soluble GITRL domains (i), (iii) and (v) are soluble human GITRL domains. The first soluble GITRL domain (i) may be selected from native, shortened and/or mutated sequences. Thus, the first soluble GITRL domain (i) has an N-terminal sequence which may start at amino acid Glu56 or Pro57 of human GITRL, and wherein Glu56 may be replaced by a neutral amino acid, e.g. by Ser or Gly or by Gln to enable pyroglutamate formation during expression. The second and third soluble GITRL domains (iii) and (v) have a shortened N-terminal sequence which preferably starts with amino acid Glu56 or Pro57 of human GITRL (SEQ ID NO:1) and wherein Glu56 may be replaced by another amino acid, e.g. Ser or Gly.

Preferably, the N-terminal sequence of the soluble GITRL domains (iii) and (v) is selected from:

(a) Glu56 or Pro57

(b) (Gly/Ser) 56

The soluble GITRL domain preferably ends with amino acid S177 of human GITRL. In certain embodiments, the GITRL domain may comprise internal mutations as described above.

Components (ii) and (iv) of the GITR receptor agonist protein are peptide linker elements located between components (i) and (iii) or (iii) and (v), respectively. The flexible linker elements have a length of 3-8 amino acids, particularly a length of 3, 4, 5, 6, 7, or 8 amino acids. The linker elements are preferably glycine/serine linkers, i.e. peptide linkers substantially consisting of the amino acids glycine and serine. In cases in in which the soluble cytokine domain starts with S or G (N-terminus), the linker ends before this S or G.

It should be noted that linker (ii) and linker (iv) do not need to be of the same length. In order to decrease potential immunogenicity, it may be preferred to use shorter linkers. In addition it turned out that shorter linkers lead to single chain molecules with reduced tendency to form aggregates. Whereas linkers that are substantially longer than the ones disclosed here may exhibit unfavorable aggregations properties.

If desired, the linker may comprise an asparagine residue which may form a glycosylate site Asn-Xaa-Ser. In certain embodiments, one of the linkers, e.g. linker (ii) or linker (iv) comprises a glycosylation site. In other embodiments, both linkers (iv) comprise glycosylation sites. In order to increase the solubility of the GITRL agonist proteins and/or in order to reduce the potential immunogenicity, it may be preferred that linker (ii) or linker (iv) or both comprise a glycosylation site.

Preferred linker sequences are shown in Table 2. A preferred linker is GSGSGNGS (SEQ ID NO: 2).

TABLE 2

Example Linker Sequences

| SEQ ID NO | Sequence |
|---|---|
| 2 | GSGSGNGS |
| 3 | GSGSGSGS |
| 4 | GGSGSGSG |
| 5 | GGSGSG |
| 6 | GGSG |
| 7 | GGSGNGSG |

TABLE 2-continued

Example Linker Sequences

| SEQ ID NO | Sequence |
|---|---|
| 8 | GGNGSGSG |
| 9 | GGNGSG |
| 10 | GSGSGS |
| 11 | GSGS |
| 12 | GSG |

The GITR receptor agonist protein additionally comprises an antibody Fc fragment domain which may be located N-terminal to the first GITRL domain (i) and/or C-terminal to the third GITRL domain (v). Preferably, the antibody Fc fragment domain comprises a reduced capability to interact with Fc-gamma-R receptors in vivo. Preferably, the antibody Fc fragment domain comprises or consists of an amino acid sequence as shown in SEQ ID NO: 13 or 14 (see Table 3). Sequence ID NO: 13 has N297S mutation compared to wildtype human IGG1-Fc. Sequence ID NO: 14 is a glycosylated (N297 wildtype) human IGG1 Fc mutein with reduced Fc-gamma-R binding capability.

TABLE 3

Examples of Fc Fragment Domains

| SEQ ID NO | Sequence |
|---|---|
| 13 | PAPELLGGPSVFLFPPKPKDTLMISRTPEVTCVVVDVSHEDPE VKFNWYVDGVEVHNAKTKPREEQYSSTYRVVSVLTVLHQDWLN GKEYKCKVSNKALPAPIEKTISKAKGQPREPQVYTLPPSREEM TKNQVSLTCLVKGFYPSDIAVEWESNGQPENNYKTTPPVLDSD GSFFLYSKLTVDKSRWQQGNVFSCSVMHEALHNHYTQKSLSLS PGK |
| 14 | PAPPVAGPSVFLFPPKPKDTLMISRTPEVTCVVVDVSHEDPEV KFNWYVDGVEVHNAKTKPREEQYNSTYRVVSVLTVLHQDWLNG KEYKCKVSNKGLPSSIEKTISKAKGQPREPQVYTLPPSREEMT KNQVSLTCLVKGFYPSDIAVEWESNGQPENNYKTTPPVLDSDG SFFLYSKLTVDKSRWQQGNVFSCSVMHEALHNHYTQKSLSLSP GK |

Number of Glycosylation Sites and In Vivo Stability

The total number of glycosylation sites and the individual position of the carbohydrates in three dimensions impacts the in-vivo stability of GITR receptor agonist proteins.

Further, carbohydrate recognition depends on local density of the terminal saccharides, the branching of the carbohydrate tree and the relative position of the carbohydrates to each other matter.

Further, partially degraded carbohydrates reduce the in vivo half-life of GITR receptor agonist proteins through lectin-driven mechanisms. By reducing the total number of glycosylation sites on the molecule, the resulting compound is less accessible to these mechanisms, increasing half-life.

Depletion of the CH2-domain carbohydrates of the Fc-domain is necessary in order to avoid Fc-gamma-Receptor based binding. FcR-gamma-Receptors on cells could lead to hyper-crosslinking of the fusion-protein in vivo potential leading to GITR-receptor superclustering-based toxicity. Also, unwanted Fc-driven mechanisms like ADCC could lead to toxic events. Accordingly, in one embodiment, the overall number of glycosylation sites on the GITR receptor agonist proteins of the instant invention is reduced through the depletion of CH2 glycosylation sites, particularly the N-glycosylation site, resulting in GITR receptor agonist proteins comprising N297S equivalent mutations of SEQ ID NO: 15 (PROTEIN A) (according to the EU numbering system) creating aglycosl-CH2 domains. In another embodiment of the invention, one or more of the soluble GITRL domains (i), (iii), and (v) may comprise N129 exchanged to aspartate, serine or glycine resulting in GITR receptor agonistic fusion proteins with a reduced number of glycosylation sites. In a preferred embodiment, the N129[D,S,G] and N114[D,S,G] mutations are restricted to the soluble GITRL domains (iii) and (v) of the agonistic GITR receptor agonistic fusion proteins of the present invention.

CH2-Domain Destabilization is Compensated by an Additional Hinge-Cysteine

CH2-glycosylation present on the inner surface areas normally shields the subdomain from proteases during "open Fc-conformation transits" wherein hinge-interchain disulfide bonds are reduced and the covalent interchain linkage is disrupted. This enables CH2-dissociation and exposure of the inner surface area towards proteases. GITR receptor agonist proteins comprising an Fc-domain with a N297S equivalent mutation of SEQ ID NO: 15 (PROTEIN A) (according to the EU numbering system) creates an aglycosylated-CH2 and are therefore likely to be subject to protease digestion and less stable than equivalent structures with wild-type CH2 glycosylation. This would impact the compound's stability during USP/DSP/storage, where host cell proteases are present and have long-term access to the structure. Accordingly, in certain embodiments, the GITR receptor agonist lacks CH2 glycosylation sites, but comprises glycosylation sites in the linker sequences of each polypeptide chain (e.g., GSGSGNGS, SEQ ID NO: 2).

According to a preferred embodiment of the invention, the antibody Fc fragment domain is fused via a hinge-linker element. The hinge-linker element has a length of 10-30 amino acids, particularly a length of 15-25 amino acids, e.g. 22 amino acids. The term "hinge-linker" includes any linker long enough to allow the domains attached by the hinge-linker element to attain a biologically active confirmation. The hinge-linker element preferably comprises the hinge-region sequence of an immunoglobulin, herein referred to as "Ig hinge-region". The term "Ig hinge-region" means any polypeptide comprising an amino acid sequence that shares sequence identity or similarity with a portion of a naturally occurring Ig hinge-region sequence which includes one or more cysteine residues, e.g., two cysteine residues, at which the disulfide bonds link the two heavy chains of the immunoglobulin.

Derivatives and analogues of the hinge-region can be obtained by mutations. A derivative or analogue as referred to herein is a polypeptide comprising an amino acid sequence that shares sequence identity or similarity with the full length sequence of the wild type (or naturally occurring protein) except that it has one or more amino acid sequence differences attributable to a deletion, insertion and/or substitution.

The number of molecules with open Fc-conformation in an individual GITR receptor agonist protein depends on the number of interchain-disulfide bonds present in the hinge region. Accordingly, in one embodiment a third cysteine (C225 according to the EU numbering system) was introduced into the hinge region of the GITR receptor agonist proteins of the instant invention in order to ameliorate the effect of depleting the CH2-glycosites.

Exchange of a Lysine to Glycine in the Hinge Region Results in Enhanced Proteolytic Stability In one embodiment, the GITR receptor agonist proteins of the invention additionally comprise a mutation of the upper-hinge lysine (K223, according to the EU numbering system) to a glycine to reduce proteolytic processing at this site, thereby enhancing the overall stability of the fusion protein. Combining aforementioned introduction of a third cysteine (C225, according to the EU numbering system) with the aforementioned lysine to glycine mutation (K223G, according to the EU numbering system) within the hinge region results in an overall stabilized GITR receptor agonist protein of the instant invention.

A particularly preferred hinge-linker element including the aforementioned cysteine (C225) and the lysine to glycine mutation (K223G) comprises or consists of the amino acid sequence as shown in SEQ ID NO: 16 (Table 4).

Endogenous Cysteines Interfere with Hinge-Disulfide Formation

The interchain-disulfide connectivity of the hinge region stabilizing the homodimer of the hexavalent GITR receptor agonist protein is also affected by the free thiol groups of the GITRL subsequences. Free thiol groups can be created through reduction of surface exposed disulfide-bridges, e.g. by reduction of the C58-C78 disulfide of GITRL. This also leads to the aforementioned open FC-conformation due to self-reduction of the hinge disulfide-bridges of the structure by the endogenous free thiols of the preparation at high protein concentrations. In consequence, single-chain GITRL-FC fusion proteins comprising free thiols are expected to be less stable during manufacture and storage, when longtime exposure to oxygen and proteases occurs.

Therefore, to potentially enable manufacture of a hexavalent GITR receptor agonist at technical scale, the C58 and C78 residues are preferably mutated simultaneously to a different amino-acid (e.g. L, S, A or G).

The GITR receptor agonist protein may additionally comprise an N-terminal signal peptide domain, which allows processing, e.g. extracellular secretion, in a suitable host cell. Preferably, the N-terminal signal peptide domain comprises a protease cleavage site, e.g. a signal peptidase cleavage site and thus may be removed after or during expression to obtain the mature protein. A particularly preferred N-terminal signal peptide domain comprises the amino acid sequence as shown in SEQ ID NO: 17 (Table 4).

Further, the GITR receptor agonist protein may additionally comprise a C-terminal element, having a length of e.g. 1-50, preferably 10-30 amino acids which may include or connect to a recognition/purification domain, e.g. a FLAG domain, a Strep-tag or Strep-tag II domain and/or a poly-His domain. According to a preferred embodiment, the fusion polypeptide comprises a Strep-tag fused to the C-terminus via a short serine linker as shown in SEQ ID NO: 18 (Table 4).

Preferred hinge-linker elements (SEQ ID NO: 16, 19-24), a preferred N-terminal signal peptide domain (SEQ ID NO: 17) and a preferred serine linker-strep tag (SEQ ID NO: 18) are shown in Table 4.

TABLE 4

Exemplary domains and linkers

| SEQ ID NO | Sequence |
|---|---|
| 16 | GSSSSSSSSGSCDKTHTCPPC |
| 17 | METDTLLVFVLLVWVPAGNG |
| 18 | SSSSSSAWSHPQFEK |
| 19 | GSSSSSSSGSCDKTHTCPPC |
| 20 | GSSSSSSGSCDKTHTCPPC |
| 21 | GSSSSSGSCDKTHTCPPC |
| 22 | GSSSGSCDKTHTCPPC |
| 23 | GSSSGSCDKTHTCPPCGS |
| 24 | GSSSGSCDKTHTCPPCGSGS |

In one embodiment of the invention, the fusion polypeptide comprises three soluble GITRL domains fused by peptide linker elements of SEQ ID NO: 2. All three soluble GITRL domain (i), (iii), (v) consists of amino acids 52-177 of human GITRL according to SEQ ID NO: 1. The resulting scGITRL-RBD sequence module is shown in table 5b SEQ ID NO: 36.

In a further preferred embodiment of the invention, the fusion polypeptide comprises three soluble GITRL domains fused by peptide linker elements of SEQ ID NO: 2. All three soluble GITRL domain (i), (iii), (v) consists of amino acids 52-177 of human GITRL according to SEQ ID NO: 1 with E52Q mutation in the first domain (i). The resulting scGITRL-RBD sequence module is shown in table 5b SEQ ID NO: 39.

In another embodiment of the invention, the fusion polypeptide comprises three soluble GITRL domains fused by peptide linker elements of SEQ ID NO: 2. All three soluble GITRL domain (i), (iii), (v) consists of amino acids 56-177 of human GITRL according to SEQ ID NO: 1. The resulting scGITRL-RBD sequence module is shown in table 5b SEQ ID NO: 40.

In still another preferred embodiment of the invention, the fusion polypeptide comprises three soluble GITRL domains fused by peptide linker elements of SEQ ID NO: 2. All three soluble GITRL domain (i), (iii), (v) consists of amino acids 56-177 of human GITRL according to SEQ ID NO: 1 with E56Q mutation in the first domain (i). The resulting scGITRL-RBD sequence module is shown in table 5b SEQ ID NO: 41.

In another embodiment of the invention, the fusion polypeptide comprises three soluble GITRL domains fused by peptide linker elements of SEQ ID NO: 2. All three soluble GITRL domain (i), (iii), (v) consists of amino acids 55-177 of human GITRL according to SEQ ID NO: 1. The resulting scGITRL-RBD sequence module is shown in table 5b SEQ ID NO: 42.

In still another preferred embodiment of the invention, the fusion polypeptide comprises three soluble GITRL domains fused by peptide linker elements of SEQ ID NO: 2. All three soluble GITRL domain (i), (iii), (v) consists of amino acids 55-177 of human GITRL according to SEQ ID NO: 1 with K55Q mutation in the first domain (i). The resulting scGITRL-RBD sequence module is shown in table 5b SEQ ID NO: 43.

In another embodiment of the invention, the fusion polypeptide comprises three soluble GITRL domains fused by peptide linker elements of SEQ ID NO: 2. The first soluble GITRL domain (i) consists of amino acids 56-177 of human GITRL according to SEQ ID NO: 1 and the soluble GITRL domains (iii) and (v) consist of amino acids 57-177 of human GITRL according to SEQ ID NO: 1 The resulting scGITRL-RBD sequence module is shown in table 5b SEQ ID NO: 44

In another embodiment of the invention, the fusion polypeptide comprises three soluble GITRL domains fused by peptide linker elements of SEQ ID NO: 2. The first soluble GITRL domain (i) consists of amino acids 56-177 of human GITRL according to SEQ ID NO: 1 and the soluble GITRL domains (iii) and (v) consist of amino acids 57-177 of human GITRL according to SEQ ID NO: 1 with E56Q mutation in the first domain (i). The resulting scGITRL-RBD sequence module is shown in table 5b SEQ ID NO: 45

In another embodiment of the invention, the fusion polypeptide comprises three soluble GITRL domains fused by peptide linker elements of SEQ ID NO: 2. The first soluble GITRL domain (i) consists of amino acids 56-171 of human GITRL according to SEQ ID NO: 1 and the soluble GITRL domains (iii) and (v) consist of amino acids 57-171 of human GITRL according to SEQ ID NO: 1 with E56Q mutation in the first domain (i). The resulting scGITRL-RBD sequence module is shown in table 5b SEQ ID NO: 46.

In another embodiment of the invention, the fusion polypeptide comprises three soluble GITRL domains fused by peptide linker elements of SEQ ID NO: 2. The first soluble GITRL domain (i) consists of amino acids 56-173 of human GITRL according to SEQ ID NO: 1 and the soluble GITRL domains (iii) and (v) consist of amino acids 57-173 of human GITRL according to SEQ ID NO: 1 with E56Q mutation in the first domain (i). The resulting scGITRL-RBD sequence module is shown in table 5b SEQ ID NO: 47.

In another embodiment of the invention, the fusion polypeptide comprises three soluble GITRL domains fused by two different peptide linker elements. The first linker element (ii) consists of SEQ ID NO: 2. The second linker element (iv) consists of SEQ ID NO: 11. The first soluble GITRL domain (i) consists of amino acids 56-171 of human GITRL according to SEQ ID NO: 1 and the soluble GITRL domains (iii) and (v) consist of amino acids 57-171 of human GITRL according to SEQ ID NO: 1 with E56Q mutation in the first domain (i). The resulting scGITRL-RBD sequence module is shown in table 5b SEQ ID NO: 48.

The aforementioned scGITRL-RBD modules (SEQ ID: 36, 39-48) are well suited to generate fusion proteins with additional domains fused to either N- or C-terminal end employing the linkers described in Table 2 (SEQ ID NO: 2-12).

Preferred Configuration GITRL-Fc

Additionally, the fusion polypeptide comprises an antibody Fc fragment domain according to SEQ ID NO: 13 that is fused C-terminally to the soluble GITRL domain (v) via a hinge-linker according to SEQ ID NO: 16. The inventors surprisingly found that this particular fusion polypeptide provides improved biological activity compared to bivalent agonistic anti-GITR-mAB and has a prolonged stability as compared to fusion proteins comprising a lysine in position 223 and a N297S mutation in the CH2 domain (according to the EU numbering). The amino acid sequence of an exemplary embodiment of a GITR receptor agonist protein of the invention is set forth in SEQ ID NO: 27.

Further, the fusion polypeptide may comprise an N-terminal signal peptide domain e.g. according to SEQ ID NO: 17. A specific example of a GITR receptor agonist protein of the invention is shown in SEQ ID NO: 25.

According to another preferred embodiment, the fusion polypeptide may additionally comprise a C-terminal Strep-tag that is fused to the polypeptide of the invention via a short serine linker as shown in SEQ ID NO: 18. According to this aspect of the invention, the Fc fragment preferably consists of the amino acid sequence as shown in SEQ ID NO: 13 or 14. Further, the Fc fragment may consist of a shorter Fc fragment, for example including amino acids 1-217 of SEQ ID NO: 13. Particularly preferred examples of fusion polypeptides comprising a C-terminal Strep-tag are shown in SEQ ID NO: 15 (PROTEIN A).

The exemplary GITR receptor agonist proteins as shown in SEQ ID Nos: 15, 25, and 26, each comprises an N-terminal signal peptide domain, at amino acids 1-20 of each sequence. In each case, the mature protein starts with amino acid 21. Mature exemplary GITR receptor agonist proteins (without a signal peptide) of the instant invention are set forth in SEQ ID NO: 27-35, 49 and 50. Exemplary GITR receptor agonist proteins described above are shown in Table 5.

The GITR receptor agonist as set forth in SEQ ID NO: 27 has a reduced total number of glycosylation sites (the N297S mutation in the CH2 region providing an aglycosylated CH2 domain, according to the EU numbering system), an increased number of interchain disulfide bonds in the hinge region, and the mutation of an upper-hinge lysine to a glycine (K223G, according to the EU numbering system). These alterations provide a decrease in potential degradation and GITR receptor superclustering (along with concomitant toxicity).

The GITR receptor agonist as set forth in SEQ ID NO: 30 comprises the same layout as SEQ ID NO: 27 but with the E52Q mutation in the soluble GITRL domains (i) employing the scGITRL-RBD module shown SEQ ID NO: 39. The mature protein comprises the N-terminal E52Q mutation thereby enabling formation of pyroglutamate leading to protection of the N-terminus against aminopeptidases and subsequently enhancing the overall stability of the protein during manufacture and storage.

The GITR receptor agonist as set forth in SEQ ID NO: 31 comprises a scGITRL-RBD module with SEQ ID NO: 45, a third peptide linker with SEQ ID NO: 16 and (vii) an antibody Fc fragment with SEQ ID NO: 13.

The GITR receptor agonist as set forth in SEQ ID NO: 32 comprises a scGITRL-RBD module with SEQ ID NO: 41, a third peptide linker with SEQ ID NO: 21 and (vii) an antibody Fc fragment with SEQ ID NO: 13.

The GITR receptor agonist as set forth in SEQ ID NO: 33 comprises a scGITRL-RBD module with SEQ ID NO: 46, a third peptide linker with SEQ ID NO: 16 and (vii) an antibody Fc fragment with SEQ ID NO: 13.

The GITR receptor agonist as set forth in SEQ ID NO: 34 comprises a scGITRL-RBD module with SEQ ID NO: 43, a third peptide linker with SEQ ID NO: 16 and (vii) an antibody Fc fragment with SEQ ID NO: 13.

The GITR receptor agonist as set forth in SEQ ID NO: 35 comprises a scGITRL-RBD module with SEQ ID NO: 47, a third peptide linker with SEQ ID NO: 16 and (vii) an antibody Fc fragment with SEQ ID NO: 13.

A further exemplary GITR receptor agonist comprises a scGITRL-RBD module with SEQ ID NO: 45, a third peptide linker with SEQ ID NO: 16 and (vii) an antibody Fc fragment with SEQ ID NO: 13.

The GITR receptor agonist as set forth in SEQ ID NO: 49 (Protein B) comprises a scGITRL-RBD module with SEQ ID NO: 41, a third peptide linker with SEQ ID NO: 16 and (vii) an antibody Fc fragment with SEQ ID NO: 13.

The GITR receptor agonist as set forth in SEQ ID NO: 50 (Protein C) comprises a scGITRL-RBD module with SEQ ID NO: 48, a third peptide linker with SEQ ID NO: 16 and (vii) an antibody Fc fragment with SEQ ID NO: 13.

TABLE 5

Exemplary GITR receptor agonist Proteins

| SEQ ID NO | Sequence |
|---|---|
| 25 PROTEIN A without StrepTag | METDTLLVFVLLVWVPAGNGETAKEPCMAKFGPLPSKWQMASSEPPCVNKVSDWKLEILQNGLYLIYGQVAPNANYNDVAPFEVRLYKNKDMIQTLTNKSKIQNVGGTYELHVGDTIDLIFNSEHQVLKNNTYWGIILLANPQFISGSGSGNGSETAKEPCMAKFGPLPSKWQMASSEPPCVNKVSDWKLEILQNGLYLIYGQVAPNANYNDVAPFEVRLYKNKDMIQTLINKSKIQNVGGIYELHVGDTIDLIFNSEHQVLKNNTYWGIILLANPQFISGSGSGNGSETAKEPCMAKFGPLPSKWQMASSEPPCVNKVSDWKLEILQNGLYLIYGQVAPNANYNDVAPFEVRLYKNKDMIQTLTNKSKIQNVGGTYELHVGDTIDLIFNSEHQVLKNNTYWGIILLANPQFISGSSSSSSSSGSCDKTHTCPPCPAPELLGGPSVFLFPPKPKDTLMISRIPEVTCVVVDVSHEDPEVKFNWYVDGVEVHNAKTKPREEQYSSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 15 PROTEIN A | METDTLLVFVLLVWVPAGNGETAKEPCMAKFGPLPSKWQMASSEPPCVNKVSDWKLEILQNGLYLIYGQVAPNANYNDVAPFEVRLYKNKDMIQTLTNKSKIQNVGGTYELHVGDTIDLIFNSEHQVLKNNTYWGIILLANPQFISGSGSGNGSETAKEPCMAKFGPLPSKWQMASSEPPCVNKVSDWKLEILQNGLYLIYGQVAPNANYNDVAPFEVRLYKNKDMIQTLINKSKIQNVGGIYELHVGDTIDLIFNSEHQVLKNNTYWGIILLANPQFISGSGSGNGSETAKEPCMAKFGPLPSKWQMASSEPPCVNKVSDWKLEILQNGLYLIYGQVAPNANYNDVAPFEVRLYKNKDMIQTLTNKSKIQNVGGTYELHVGDTIDLIFNSEHQVLKNNTYWGIILLANPQFISGSSSSSSSSGSCDKTHTCPPCPAPELLGGPSVFLFPPKPKDTLMISRIPEVTCVVVDVSHEDPEVKFNWYVDGVEVHNAKTKPREEQYSSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGSSSSSSAWSHPQFEK |
| 26 GITRL-wt + SEQ14 | METDTLLVFVLLVWVPAGNGETAKEPCMAKFGPLPSKWQMASSEPPCVNKVSDWKLEILQNGLYLIYGQVAPNANYNDVAPFEVRLYKNKDMIQTLTNKSKIQNVGGTYELHVGDTIDLIFNSEHQVLKNNTYWGIILLANPQFISGSGSGNGSETAKEPCMAKFGPLPSKWQMASSEPPCVNKVSDWKLEILQNGLYLIYGQVAPNANYNDVAPFEVRLYKNKDMIQTLINKSKIQNVGGIYELHVGDTIDLIFNSEHQVLKNNTYWGIILLANPQFISGSGSGNGSETAKEPCMAKFGPLPSKWQMASSEPPCVNKVSDWKLEILQNGLYLIYGQVAPNANYNDVAPFEVRLYKNKDMIQTLTNKSKIQNVGGTYELHVGDTIDLIFNSEHQVLKNNTYWGIILLANPQFISGSSSSSSSSGSCDKTHTCPPCPAPPVAGPSVFLFPPKPKDTLMISRTPEVTCVVVDVSHEDPEVKFNWYVDGVEVHNAKTKPREEQYNSTYRVVSVLTVLHQDWLNGKEYKCKVSNKGLPSSIEKTISKAKGQPREPQVYTLPPSREEMTKNQVSLTCLVKGFYPSDIAVEWESNGQPENNYKITPPVLDSDGSFFLYSKLTVDKSRWQQGNVFSCSVMHEALHNHYTQKSLSLSPGK |
| 27 GITRL-wt + SEQ13(FC) No Signal No Strep No Glyco | ETAKEPCMAKFGPLPSKWQMASSEPPCVNKVSDWKLEILQNGLYLIYGQVAPNANYNDVAPFEVRLYKNKDMIQTLINKSKIQNVGGIYELHVGDTIDLIFNSEHQVLKNNTYWGIILLANPQFISGSGSGNGSETAKEPCMAKFGPLPSKWQMASSEPPCVNKVSDWKLEILQNGLYLIYGQVAPNANYNDVAPFEVRLYKNKDMIQTLTNKSKIQNVGGTYEL3HVGDTIDLIFNSEHQVLKNNTYWGIILLANPQFISGSGSGNGSETAKEPCMAKFGPLPSKWQMASSEPPCVNKVSDWKLEILQNGLYLIYGQVAPNANYNDVAPFEVRLYKNKDMIQTLTNKSKIQNVGGTYELHVGDTIDLIFNSEHQVLKNNTYWGIILLANPQFISGSSSSSSSSGSCDKTHTCPPCPAPELLGGPSVFLFPPKPKDTLMISRTPEVTCVVVDVSHEDPEVKFNWYVDGVEVHNAKTKPREEQYSSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 28 Deglyco-Fc No Signal StrepTag | ETAKEPCMAKFGPLPSKWQMASSEPPCVNKVSDWKLEILQNGLYLIYGQVAPNANYNDVAPFEVRLYKNKDMIQTLINKSKIQNVGGIYELHVGDTIDLIFNSEHQVLKNNTYWGIILLANPQFISGSGSGNGSETAKEPCMAKFGPLPSKWQMASSEPPCVNKVSDWKLEILQNGLYLIYGQVAPNANYNDVAPFEVRLYKNKDMIQTLTNKSKIQNVGGTYELHVGDTIDLIFNSEHQVLKNNTYWGIILLANPQFISGSGSGNGSETAKEPCMAKFGPLPSKWQMASSEPPCVNKVSDWKLEILQNGLYLIYGQVAPNANYNDVAPFEVRLYKNKDMIQTLINKSKIQNVGGIYELHVGDTIDLIFNSEHQVLKNNTYWGIILLANPQFISGSSSSSSSSGSCDKTHTCPPCPAPELLGGPSVFLFPPKPKDTLMISRTPEVTCVVVDVSHEDPEVKFNWYVDGVEVHNAKTKPREEQYSSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGSSSSSSAWSHPQFEK |
| 29 Glyco FC No Signal No strep | ETAKEPCMAKFGPLPSKWQMASSEPPCVNKVSDWKLEILQNGLYLIYGQVAPNANYNDVAPFEVRLYKNKDMIQTLINKSKIQNVGGIYELHVGDTIDLIFNSEHQVLKNNTYWGIILLANPQFISGSGSGNGSETAKEPCMAKFGPLPSKWQMASSEPPCVNKVSDWKLEILQNGLYLIYGQVAPNANYNDVAPFEVRLYKNKDMIQTLTNKSKIQNVGGTYELHVGDTIDLIFNSEHQVLKNNTYWGIILLANPQFISGSGSGNGSETAKEPCMAKFGPLPSKWQMASSEPPCVNKVSDWKLEILQNGLYLIYGQVAPNANYNDVAPFEVRLYKNKDMIQTLINKSKIQNVGGIYELHVGDTIDLIFNSEHQVLKNNTYWGIILLANPQFISGSSSSSSSSGSCDKTHTCPPCPAPPVAGPSVFLFPPKP |

TABLE 5-continued

| Exemplary GITR receptor agonist Proteins | |
|---|---|
| SEQ ID NO | Sequence |
| | KDTLMISRTPEVTCVVVDVSHEDPEVKFNWYVDGVEVHNAKTKPREEQYNSTYR<br>VVSVLTVLHQDWLNGKEYKCKVSNKGLPSSIEKTISKAKGQPREPQVYTLPPSR<br>EEMTKNQVSLTCLVKGFYPSDIAVEWESNGQPENNYKTTPPVLDSDGSFFLYSK<br>LTVDKSRWQQGNVFSCSVMHEALHNHYTQKSLSLSPGK |
| 30<br>SEQ39 +<br>FC13 | QTAKEPCMAKFGPLPSKWQMASSEPPCVNKVSDWKLEILQNGLYLIYGQVAPNA<br>NYNDVAPFEVRLYKNKDMIQTLINKSKIQNVGGIYELHVGDTIDLIFNSEHQVL<br>KNNTYWGIILLANPQFISGSGSGNGSETAKEPCMAKFGPLPSKWQMASSEPPCV<br>NKVSDWKLEILQNGLYLIYGQVAPNANYNDVAPFEVRLYKNKDMIQTLTNKSKI<br>QNVGGTYELHVGDTIDLIFNSEHQVLKNNTYWGIILLANPQFISGSGSGNGSET<br>AKEPCMAKFGPLPSKWQMASSEPPCVNKVSDWKLEILQNGLYLIYGQVAPNANY<br>NDVAPFEVRLYKNKDMIQTLINKSKIQNVGGIYELHVGDTIDLIFNSEHQVLKN<br>NTYWGIILLANPQFISGSSSSSSSSGSCDKTHTCPPCPAPELLGGPSVFLFPPK<br>PKDTLMISRTPEVTCVVVDVSHEDPEVKFNWYVDGVEVHNAKTKPREEQYSSTY<br>RVVSVLTVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSDGSFFLYS<br>KLTVDKSRWQQGNVFSCSVMHEALHNHYTQKSLSLSPGK |
| 31 | QPCMAKFGPLPSKWQMASSEPPCVNKVSDWKLEILQNGLYLIYGQVAPNANYND<br>VAPFEVRLYKNKDMIQTLINKSKIQNVGGIYELHVGDTIDLIFNSEHQVLKNNT<br>YWGIILLANPQFISGSGSGNGSPCMAKFGPLPSKWQMASSEPPCVNKVSDWKLE<br>ILQNGLYLIYGQVAPNANYNDVAPFEVRLYKNKDMIQTLTNKSKIQNVGGTYEL<br>HVGDTIDLIFNSEHQVLKNNTYWGIILLANPQFISGSGSGNGSPCMAKFGPLPS<br>KWQMASSEPPCVNKVSDWKLEILQNGLYLIYGQVAPNANYNDVAPFEVRLYKNK<br>DMIQTLTNKSKIQNVGGTYELHVGDTIDLIFNSEHQVLKNNTYWGIILLANPQF<br>ISGSSSSSSSSGSCDKTHTCPPCPAPELLGGPSVFLFPPKPKDTLMISRTPEVT<br>CVVVDVSHEDPEVKFNWYVDGVEVHNAKTKPREEQYSSTYRVVSVLTVLHQDWL<br>NGKEYKCKVSNKALPAPIEKTISKAKGQPREPQVYTLPPSREEMTKNQVSLTCL<br>VKGFYPSDIAVEWESNGQPENNYKTTPPVLDSDGSFFLYSKLTVDKSRWQQGNV<br>FSCSVMHEALHNHYTQKSLSLSPGK |
| 32 | QPCMAKFGPLPSKWQMASSEPPCVNKVSDWKLEILQNGLYLIYGQVAPNANYND<br>VAPFEVRLYKNKDMIQTLINKSKIQNVGGIYELHVGDTIDLIFNSEHQVLKNNT<br>YWGIILLANPQFISGSGSGNGSEPCMAKFGPLPSKWQMASSEPPCVNKVSDWKL<br>EILQNGLYLIYGQVAPNANYNDVAPFEVRLYKNKDMIQTLTNKSKIQNVGGTYE<br>LHVGDTIDLIFNSEHQVLKNNTYWGIILLANPQFISGSGSGNGSEPCMAKFGPL<br>PSKWQMASSEPPCVNKVSDWKLEILQNGLYLIYGQVAPNANYNDVAPFEVRLYK<br>NKDMIQTLTNKSKIQNVGGTYELHVGDTIDLIFNSEHQVLKNNTYWGIILLANP<br>QFISGSSSSSGSCDKTHTCPPCPAPELLGGPSVFLFPPKPKDTLMISRTPEVIC<br>VVVDVSHEDPEVKFNWYVDGVEVHNAKTKPREEQYSSTYRVVSVLTVLHQDWLN<br>GKEYKCKVSNKALPAPIEKTISKAKGQPREPQVYTLPPSREEMTKNQVSLTCLV<br>KGFYPSDIAVEWESNGQPENNYKITPPVLDSDGSFFLYSKLTVDKSRWQQGNVF<br>SCSVMHEALHNHYTQKSLSLSPGK |
| 33 | QPCMAKFGPLPSKWQMASSEPPCVNKVSDWKLEILQNGLYLIYGQVAPNANYND<br>VAPFEVRLYKNKDMIQTLINKSKIQNVGGIYELHVGDTIDLIFNSEHQVLKNNT<br>YWGIILLAGSGSGNGSPCMAKFGPLPSKWQMASSEPPCVNKVSDWKLEILQNGL<br>YLIYGQVAPNANYNDVAPFEVRLYKNKDMIQTLTNKSKIQNVGGTYELHVGDTI<br>DLIFNSEHQVLKNNTYWGIILLAGSGSGNGSPCMAKFGPLPSKWQMASSEPPCV<br>NKVSDWKLEILQNGLYLIYGQVAPNANYNDVAPFEVRLYKNKDMIQTLTNKSKI<br>QNVGGTYELHVGDTIDLIFNSEHQVLKNNTYWGIILLAGSSSSSSSSGSCDKTH<br>TCPPCPAPELLGGPSVFLFPPKPKDTLMISRIPEVTCVVVDVSHEDPEVKFNWY<br>VDGVEVHNAKTKPREEQYSSTYRVVSVLTVLHQDWLNGKEYKCKVSNKALPAPI<br>EKTISKAKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHNHYTQKS<br>LSLSPGK |
| 34 | QEPCMAKFGPLPSKWQMASSEPPCVNKVSDWKLEILQNGLYLIYGQVAPNANYN<br>DVAPFEVRLYKNKDMIQTLTNKSKIQNVGGTYELHVGDTIDLIFNSEHQVLKNN<br>TYWGIILLANPQFISGSGSGNGSKEPCMAKFGPLPSKWQMASSEPPCVNKVSDW<br>KLEILQNGLYLIYGQVAPNANYNDVAPFEVRLYKNKDMIQTLTNKSKIQNVGGT<br>YELHVGDTIDLIFNSEHQVLKNNTYWGIILLANPQFISGSGSGNGSKEPCMAKF<br>GPLPSKWQMASSEPPCVNKVSDWKLEILQNGLYLIYGQVAPNANYNDVAPFEVR<br>LYKNKDMIQTLTNKSKIQNVGGTYELHVGDTIDLIFNSEHQVLKNNTYWGIILL<br>ANPQFISGSSSSSSSSGSCDKTHTCPPCPAPELLGGPSVFLFPPKPKDTLMISR<br>TPEVTCVVVDVSHEDPEVKFNWYVDGVEVHNAKTKPREEQYSSTYRVVSVLTVL<br>HQDWLNGKEYKCKVSNKALPAPIEKTISKAKGQPREPQVYTLPPSREEMTKNQV<br>SLTCLVKGFYPSDIAVEWESNGQPENNYKTTPPVLDSDGSFFLYSKLTVDKSRW<br>QQGNVFSCSVMHEALHNHYTQKSLSLSPGK |
| 35 | QPCMAKFGPLPSKWQMASSEPPCVNKVSDWKLEILQNGLYLIYGQVAPNANYND<br>VAPFEVRLYKNKDMIQTLINKSKIQNVGGIYELHVGDTIDLIFNSEHQVLKNNT<br>YWGIILLANPQGSGSGNGSPCMAKFGPLPSKWQMASSEPPCVNKVSDWKLEILQ<br>NGLYLIYGQVAPNANYNDVAPFEVRLYKNKDMIQTLTNKSKIQNVGGTYELHVG<br>DTIDLIFNSEHQVLKNNTYWGIILLANPGSGSGNGSPCMAKFGPLPSKWQMASS<br>EPPCVNKVSDWKLEILQNGLYLIYGQVAPNANYNDVAPFEVRLYKNKDMIQTLT |

TABLE 5-continued

Exemplary GITR receptor agonist Proteins

| SEQ ID NO | Sequence |
|---|---|
| | NKSKIQNVGGTYELHVGDTIDLIFNSEHQVLKNNTYWGIILLANPQGSSSSSS SGSCDKTHTCPPCPAPELLGGPSVFLFPPKPKDTLMISRIPEVTCVVVDVSHED PEVKFNWYVDGVEVHNAKTKPREEQYSSTYRVVSVLTVLHQDWLNGKEYKCKVS NKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEAL HNHYTQKSLSLSPGK |
| 49 L1-8 L2-8 | QPCMAKFGPLPSKWQMASSEPPCVNKVSDWKLEILQNGLYLIYGQVAPN ANYNDVAPFEVRLYKNKDMIQTLTNKSKIQNVGGTYELHVGDTIDLIFN SEHQVLKNNTYWGIILLANPQFISGSGSGNGSEPCMAKFGPLPSKWQMA SSEPPCVNKVSDWKLEILQNGLYLIYGQVAPNANYNDVAPFEVRLYKNK DMIQTLTNKSKIQNVGGTYELHVGDTIDLIFNSEHQVLKNNTYWGIILL ANPQFISGSGSGNGSEPCMAKFGPLPSKWQMASSEPPCVNKVSDWKLEI LQNGLYLIYGQVAPNANYNDVAPFEVRLYKNKDMIQTLTNKSKIQNVGG TYELHVGDTIDLIFNSEHQVLKNNTYWGIILLANPQFISGSSSSSSSSG SCDKTHTCPPCPAPELLGGPSVFLFPPKPKDTLMISRTPEVTCVVVDVS HEDPEVKFNWYVDGVEVHNAKTKPREEQYSSTYRVVSVLTVLHQDWLNG KEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDK SRWQQGNVFSCSVMHEALHNHYTQKSLSLSPGK |
| 50 EQ C-del L1-8 L2-4 | QPCMAKFGPLPSKWQMASSEPPCVNKVSDWKLEILQNGLYLIYGQVAPN ANYNDVAPFEVRLYKNKDMIQTLTNKSKIQNVGGTYELHVGDTIDLIFN SEHQVLKNNTYWGIILLAGSGSGNGSPCMAKFGPLPSKWQMASSEPPCV NKVSDWKLEILQNGLYLIYGQVAPNANYNDVAPFEVRLYKNKDMIQTLT NKSKIQNVGGTYELHVGDTIDLIFNSEHQVLKNNTYWGIILLAGSGSPC MAKFGPLPSKWQMASSEPPCVNKVSDWKLEILQNGLYLIYGQVAPNANY NDVAPFEVRLYKNKDMIQTLTNKSKIQNVGGTYELHVGDTIDLIFNSEH QVLKNNTYWGIILLAGSSSSSSSSGSCDKTHTCPPCPAPELLGGPSVFL FPPKPKDTLMISRTPEVTCVVVDVSHEDPEVKFNWYVDGVEVHNAKTKP REEQYSSTYRVVSVLTVLHQDWLNGKEYKCKVSNKALPAPIEKTISKAK GQPREPQVYTLPPSREEMTKNQVSLTCLVKGFYPSDIAVEWESNGQPEN NYKTTPPVLDSDGSFFLYSKLTVDKSRWQQGNVFSCSVMHEALHNHYTQ KSLSLSPGK |

TABLE 5B

Exemplary scGITRL-RBD modules

| | |
|---|---|
| 36 | ETAKEPCMAKFGPLPSKWQMASSEPPCVNKVSDWKLEILQNGLYLIYGQVAPNA NYNDVAPFEVRLYKNKDMIQTLINKSKIQNVGGIYELHVGDTIDLIFNSEHQVL KNNTYWGIILLANPQFISGSGSGNGSETAKEPCMAKFGPLPSKWQMASSEPPCV NKVSDWKLEILQNGLYLIYGQVAPNANYNDVAPFEVRLYKNKDMIQTLTNKSKI QNVGGTYELHVGDTIDLIFNSEHQVLKNNTYWGIILLANPQFISGSGSGNGSET AKEPCMAKFGPLPSKWQMASSEPPCVNKVSDWKLEILQNGLYLIYGQVAPNANY NDVAPFEVRLYKNKDMIQTLINKSKIQNVGGIYELHVGDTIDLIFNSEHQVLKN NTYWGIILLANPQFIS |
| 39 | QTAKEPCMAKFGPLPSKWQMASSEPPCVNKVSDWKLEILQNGLYLIYGQVAPNA NYNDVAPFEVRLYKNKDMIQTLINKSKIQNVGGIYELHVGDTIDLIFNSEHQVL KNNTYWGIILLANPQFISGSGSGNGSETAKEPCMAKFGPLPSKWQMASSEPPCV NKVSDWKLEILQNGLYLIYGQVAPNANYNDVAPFEVRLYKNKDMIQTLTNKSKI QNVGGTYELHVGDTIDLIFNSEHQVLKNNTYWGIILLANPQFISGSGSGNGSET AKEPCMAKFGPLPSKWQMASSEPPCVNKVSDWKLEILQNGLYLIYGQVAPNANY NDVAPFEVRLYKNKDMIQTLINKSKIQNVGGIYELHVGDTIDLIFNSEHQVLKN NTYWGIILLANPQFIS |

TABLE 5B-continued

| Exemplary scGITRL-RBD modules | |
|---|---|
| 40 | EPCMAKFGPLPSKWQMASSEPPCVNKVSDWKLEILQNGLYLIYGQVAPNANYND VAPFEVRLYKNKDMIQTLINKSKIQNVGGIYELHVGDTIDLIFNSEHQVLKNNT YWGIILLANPQFISGSGSGNGSEPCMAKFGPLPSKWQMASSEPPCVNKVSDWKL EILQNGLYLIYGQVAPNANYNDVAPFEVRLYKNKDMIQTLTNKSKIQNVGGTYE LHVGDTIDLIFNSEHQVLKNNTYWGIILLANPQFISGSGSGNGSEPCMAKFGPL PSKWQMASSEPPCVNKVSDWKLEILQNGLYLIYGQVAPNANYNDVAPFEVRLYK NKDMIQTLTNKSKIQNVGGTYELHVGDTIDLIFNSEHQVLKNNTYWGIILLANP QFIS |
| 41 | QPCMAKFGPLPSKWQMASSEPPCVNKVSDWKLEILQNGLYLIYGQVAPNANYND VAPFEVRLYKNKDMIQTLINKSKIQNVGGIYELHVGDTIDLIFNSEHQVLKNNT YWGIILLANPQFISGSGSGNGSEPCMAKFGPLPSKWQMASSEPPCVNKVSDWKL EILQNGLYLIYGQVAPNANYNDVAPFEVRLYKNKDMIQTLTNKSKIQNVGGTYE LHVGDTIDLIFNSEHQVLKNNTYWGIILLANPQFISGSGSGNGSEPCMAKFGPL PSKWQMASSEPPCVNKVSDWKLEILQNGLYLIYGQVAPNANYNDVAPFEVRLYK NKDMIQTLTNKSKIQNVGGTYELHVGDTIDLIFNSEHQVLKNNTYWGIILLANP QFIS |
| 42 | KEPCMAKFGPLPSKWQMASSEPPCVNKVSDWKLEILQNGLYLIYGQVAPNANYN DVAPFEVRLYKNKDMIQTLTNKSKIQNVGGTYELHVGDTIDLIFNSEHQVLKNN TYWGIILLANPQFISGSGSGNGSKEPCMAKFGPLPSKWQMASSEPPCVNKVSDW KLEILQNGLYLIYGQVAPNANYNDVAPFEVRLYKNKDMIQTLTNKSKIQNVGGT YELHVGDTIDLIFNSEHQVLKNNTYWGIILLANPQFISGSGSGNGSKEPCMAKF GPLPSKWQMASSEPPCVNKVSDWKLEILQNGLYLIYGQVAPNANYNDVAPFEVR LYKNKDMIQTLTNKSKIQNVGGTYELHVGDTIDLIFNSEHQVLKNNTYWGIILL ANPQFIS |
| 43 | QEPCMAKFGPLPSKWQMASSEPPCVNKVSDWKLEILQNGLYLIYGQVAPNANYN DVAPFEVRLYKNKDMIQTLTNKSKIQNVGGTYELHVGDTIDLIFNSEHQVLKNN TYWGIILLANPQFISGSGSGNGSKEPCMAKFGPLPSKWQMASSEPPCVNKVSDW KLEILQNGLYLIYGQVAPNANYNDVAPFEVRLYKNKDMIQTLTNKSKIQNVGGT YELHVGDTIDLIFNSEHQVLKNNTYWGIILLANPQFISGSGSGNGSKEPCMAKF GPLPSKWQMASSEPPCVNKVSDWKLEILQNGLYLIYGQVAPNANYNDVAPFEVR LYKNKDMIQTLTNKSKIQNVGGTYELHVGDTIDLIFNSEHQVLKNNTYWGIILL ANPQFIS |
| 44 | EPCMAKFGPLPSKWQMASSEPPCVNKVSDWKLEILQNGLYLIYGQVAPNANYND VAPFEVRLYKNKDMIQTLINKSKIQNVGGIYELHVGDTIDLIFNSEHQVLKNNT YWGIILLANPQFISGSGSGNGSPCMAKFGPLPSKWQMASSEPPCVNKVSDWKLE ILQNGLYLIYGQVAPNANYNDVAPFEVRLYKNKDMIQTLTNKSKIQNVGGTYEL HVGDTIDLIFNSEHQVLKNNTYWGIILLANPQFISGSGSGNGSPCMAKFGPLPS |

TABLE 5B-continued

| Exemplary scGITRL-RBD modules | |
|---|---|
| | KWQMASSEPPCVNKVSDWKLEILQNGLYLIYGQVAPNANYNDVAPFEVRLYKNK<br>DMIQTLTNKSKIQNVGGTYELHVGDTIDLIFNSEHQVLKNNTYWGIILLANPQF<br>IS |
| 45 | QPCMAKFGPLPSKWQMASSEPPCVNKVSDWKLEILQNGLYLIYGQVAPNANYND<br>VAPFEVRLYKNKDMIQTLINKSKIQNVGGIYELHVGDTIDLIFNSEHQVLKNNT<br>YWGIILLANPQFISGSGSGNGSPCMAKFGPLPSKWQMASSEPPCVNKVSDWKLE<br>ILQNGLYLIYGQVAPNANYNDVAPFEVRLYKNKDMIQTLTNKSKIQNVGGTYEL<br>HVGDTIDLIFNSEHQVLKNNTYWGIILLANPQFISGSGSGNGSPCMAKFGPLPS<br>KWQMASSEPPCVNKVSDWKLEILQNGLYLIYGQVAPNANYNDVAPFEVRLYKNK<br>DMIQTLTNKSKIQNVGGTYELHVGDTIDLIFNSEHQVLKNNTYWGIILLANPQF<br>IS |
| 46 | QPCMAKFGPLPSKWQMASSEPPCVNKVSDWKLEILQNGLYLIYGQVAPNANYND<br>VAPFEVRLYKNKDMIQTLINKSKIQNVGGIYELHVGDTIDLIFNSEHQVLKNNT<br>YWGIILLAGSGSGNGSPCMAKFGPLPSKWQMASSEPPCVNKVSDWKLEILQNGL<br>YLIYGQVAPNANYNDVAPFEVRLYKNKDMIQTLTNKSKIQNVGGTYELHVGDTI<br>DLIFNSEHQVLKNNTYWGIILLAGSGSGNGSPCMAKFGPLPSKWQMASSEPPCV<br>NKVSDWKLEILQNGLYLIYGQVAPNANYNDVAPFEVRLYKNKDMIQTLTNKSKI<br>QNVGGTYELHVGDTIDLIFNSEHQVLKNNTYWGIILLA |
| 47 | QPCMAKFGPLPSKWQMASSEPPCVNKVSDWKLEILQNGLYLIYGQVAPNANYND<br>VAPFEVRLYKNKDMIQTLINKSKIQNVGGIYELHVGDTIDLIFNSEHQVLKNNT<br>YWGIILLANPQGSGSGNGSPCMAKFGPLPSKWQMASSEPPCVNKVSDWKLEILQ<br>NGLYLIYGQVAPNANYNDVAPFEVRLYKNKDMIQTLTNKSKIQNVGGTYELHVG<br>DTIDLIFNSEHQVLKNNTYWGIILLANPGSGSGNGSPCMAKFGPLPSKWQMASS<br>EPPCVNKVSDWKLEILQNGLYLIYGQVAPNANYNDVAPFEVRLYKNKDMIQTLT<br>NKSKIQNVGGTYELHVGDTIDLIFNSEHQVLKNNTYWGIILLANPQ |
| 48 | QPCMAKFGPLPSKWQMASSEPPCVNKVSDWKLEILQNGLYLIYGQVAPNANYND<br>VAPFEVRLYKNKDMIQTLINKSKIQNVGGIYELHVGDTIDLIFNSEHQVLKNNT<br>YWGIILLAGSGSGNGSPCMAKFGPLPSKWQMASSEPPCVNKVSDWKLEILQNGL<br>YLIYGQVAPNANYNDVAPFEVRLYKNKDMIQTLTNKSKIQNVGGTYELHVGDTI<br>DLIFNSEHQVLKNNTYWGIILLAGSGSPCMAKFGPLPSKWQMASSEPPCVNKVS<br>DWKLEILQNGLYLIYGQVAPNANYNDVAPFEVRLYKNKDMIQTLTNKSKIQNVG<br>GTYELHVGDTIDLIFNSEHQVLKNNTYWGIILLA |

Furthermore, it has to be noted that the scGITRL-RBD module (SEQ ID NO: 36) is well suited to generate fusion proteins with additional domains fused to either N- or C-terminal end employing the linkers described in Table 2 (SEQ ID NO: 2-12).

A further aspect of the present invention relates to a nucleic acid molecule encoding a GITR receptor agonist protein as described herein. The nucleic acid molecule may be a DNA molecule, e.g. a double-stranded or single-stranded DNA molecule, or an RNA molecule. The nucleic acid molecule may encode the GITR receptor agonist protein or a precursor thereof, e.g. a pro- or pre-proform of the GITR receptor agonist protein which may comprise a signal sequence or other heterologous amino acid portions for secretion or purification which are preferably located at the N- and/or C-terminus of the GITR receptor agonist protein. The heterologous amino acid portions may be linked to the first and/or second domain via a protease cleavage site, e.g. a Factor X3, thrombin or IgA protease cleavage site. A specific example of a nucleic acid sequence of the invention is shown in Table 6 as SEQ ID NO: 37. This nucleic acid molecule comprises the open reading frame encoding the fusion polypeptide of SEQ ID NO: 25.

TABLE 6

Nucleic Acid Sequence of Exemplary GITR receptor agonist Protein

| SEQ ID NO | Sequence |
|---|---|
| 37 | AAGCTTTAGGGATAACAGGGTAATAGCCGCCACCATGGAGACTGAC<br>ACCCTGCTGGTGTTCGTGCTGCTGGTCTGGGTGCCTGCAGGAAATG<br>GAGAAACTGCCAAAGAGCCCTGTATGGCCAAGTTTGGCCCTCTTCC<br>CTCTAAGTGGCAGATGGCTTCCTCTGAACCACCATGCGTGAACAAA<br>GTGAGCGACTGGAAACTGGAGATCTTGCAGAACGGGCTGTATTTGA<br>TCTACGGCCAGGTGGCCCCTAATGCTAACTATAACGATGTAGCCCC<br>ATTTGAGGTCAGACTGTATAAGAATAAGGACATGATTCAGACTCTG<br>ACCAATAAGTCCAAGATCCAGAATGTGGGAGGCACTTACGAATTGC<br>ACGTGGGTGATACCATCGATTTGATCTTCAACAGCGAACATCAGGT<br>GCTCAAGAACAATACATACTGGGGAATTATACTGCTGGCAAACCCA<br>CAGTTCATTTCCGGGTCCGGTTCTGGTAACGGCTCTGAGACAGCAA<br>AAGAGCCCTGCATGGCAAAATTCGGTCCTCTGCCCAGTAAGTGGCA<br>AATGGCATCATCCGAACCTCCCTGTGTGAATAAGGTGTCAGACTGG<br>AAACTTGAGATCCTTCAGAATGGACTCTACCTCATCTATGGACAGG<br>TTGCTCCTAACGCTAATTACAATGATGTGGCTCCCTTCGAAGTTCG<br>GCTGTACAAGAATAAGGATATGATACAGACCCTTACTAACAAAAGC<br>AAAATTCAGAACGTGGGCGGAACATACGAGCTGCATGTCGGTGACA<br>CGATTGATCTGATCTTCAACTCAGAGCATCAGGTCCTGAAGAATAA<br>CACCTACTGGGGCATTATTCTGCTCGCCAATCCCCAATTTATATCC<br>GGGAGCGGGTCAGGCAACGGCAGTGAGACAGCCAAGGAACCATGTA<br>TGGCTAAATTTGGGCCCCTGCCATCTAAATGGCAGATGGCATCTAG<br>GCGAACCTCCCTGCGTTAACAAGGTATCCGACTGGAAATTGGAGAT<br>CCTCCAGAACGGACTGTACCTGATCTATGGCCAAGTCGCCCCAAAT<br>GCCAATTACAATGACGTAGCTCCCTTTGAGGTCAGGCTCTATAAGA<br>ACAAAGACATGATTCAAACACTTACCAACAAAGTAAGATACAGAAT<br>GTGGGCGGAACCTATGAACTGCACGTTGGGGATACCATTGACCTGA<br>TCTTCAACAGTGAGCACCAAGTCCTCAAGAATAACACTTATTGGGG<br>TATCATCCTGCTGGCCAACCCTCAGTTTATCAGCggatcctcgagT<br>TCATCGTCCTCATCCGGCTCATGTGATAAGACCCACACCTGCCCTC<br>CCTGTCCTGCCCCTGAGCTGCTGGGCGGACCTTCTGTGTTCCTGTT<br>CCCCCCCAAGCCTAAGGACACCCTGATGATCTCCAGGACCCCTGAG<br>GTGACCTGTGTGGTGGTGGACGTGTCTCACGAAGATCCCGAGGTGA<br>AGTTCAACTGGTACGTGGACGGCGTGGAGGTCCACAACGCCAAGAC<br>CAAGCCTAGGGAGGAGCAGTACAGCTCCACCTACCGGGTGGTGTCT<br>GTGCTGACCGTGCTGCACCAGGATTGGCTGAACGGAAAGGAGTATA<br>AGTGTAAGGTCTCCAACAAGGCCCTGCCTGCCCCCATCGAGAAAAC<br>CATCTCCAAGGCCAAGGGCCAGCCTCGGGAGCCTCAGGTGTACACC<br>CTGCCTCCTAGCAGGGAGGAGATGACCAAGAACCAGGTGTCCCTGA<br>CCTGTCTGGTGAAGGGCTTCTACCCTTCCGATATCGCCGTGGAGTG<br>GGAGTCTAATGGCCAGCCCGAGAACAACTACAAGACCACCCCTCCT<br>GTGCTGGACTCTGACGGCTCCTTCTTCCTGTACTCCAAGCTGACCG<br>TGGACAAGTCCAGATGGCAGCAGGGCAACGTGTTCTCCTGCTCCGT<br>GATGCACGAGGCCCTGCACAATCACTACACCCAGAAGTCCCTGTCT<br>CTGAGTCCGGGCAAGTAATAggcgcgcc |

The nucleic acid molecule may be operatively linked to an expression control sequence, e.g. an expression control sequence which allows expression of the nucleic acid molecule in a desired host cell. The nucleic acid molecule may be located on a vector, e.g. a plasmid, a bacteriophage, a viral vector, a chromosomal integration vector, etc. Examples of suitable expression control sequences and vectors are described for example by Sambrook et al. (1989) Molecular Cloning, A Laboratory Manual, Cold Spring Harbor Press, and Ausubel et al. (1989), Current Protocols in Molecular Biology, John Wiley & Sons or more recent editions thereof.

Various expression vector/host cell systems may be used to express the nucleic acid sequences encoding the GITR receptor agonist proteins of the present invention. Suitable host cells include, but are not limited to, prokaryotic cells such as bacteria, e.g. *E. coli*, eukaryotic host cells such as yeast cells, insect cells, plant cells or animal cells, preferably mammalian cells and, more preferably, human cells. Further, the invention relates to a non-human organism transformed or transfected with a nucleic acid molecule as described above. Such transgenic organisms may be generated by known methods of genetic transfer including homologous recombination.

A further aspect of the present invention relates to a pharmaceutical or diagnostic composition comprising as the active agent at least one GITR receptor agonist protein, a respective nucleic acid encoding therefore, or a transformed or transfected cell, all as described herein.

In another aspect, the present invention provides a pharmaceutical composition comprising a GITR receptor agonist protein disclosed herein and one or more pharmaceutically acceptable carriers, diluents, excipients, and/or adjuvants.

In another aspect, the present invention provides a nucleic acid molecule encoding the GITR receptor agonist protein. In another embodiment, the present invention provides an expression vector comprising the nucleic acid molecule. In another embodiment, the present invention provides a cell comprising the nucleic acid molecule. In a further embodiment, the cell is a eukaryotic cell. In another embodiment, the cell is a mammalian cell. In another embodiment, the cell is a Chinese Hamster Ovary (CHO) cell. In other embodiments, the cell is selected from the group consisting of CHO-DBX11, CHO-DG44, CHO-S, and CHO-K1 cells. In other embodiments, the cell is selected from the group consisting of Vero, BHK, HeLa, COS, MDCK, HEK-293, NIH-3T3, W138, BT483, Hs578T, HTB2, BT20, T47D, NSO, CRL7030, HsS78Bst, PER.C6, SP2/0-Agl4, and hybridoma cells.

In another aspect, the present invention provides a method of treating a subject having a GITRL-associated disease or disorder, the method comprising administering to the subject an effective amount of the GITR receptor agonist protein. In one embodiment, the GITR receptor agonist protein is administered alone. In another embodiment, the GITR receptor agonist protein is administered before, concurrently, or after the administration of a second agent. In another embodiment, the disease or disorder is selected from the group consisting of: tumors, infectious diseases, inflammatory diseases, metabolic diseases, autoimmune disorders, degenerative diseases, apoptosis-associated diseases, and transplant rejections. In one embodiment, the tumors are solid tumors. In one embodiment, the tumors arise from the group of cancers consisting of sarcoma, esophageal cancer, and gastric cancer. In another embodiment, the tumors arise from Ewing's sarcoma or fibrosarcoma. In another embodiment, the tumors arise from the group of cancers consisting of Non-Small Cell Lung Carcinoma (NSCLC), pancreatic cancer, colorectal cancer, breast cancer, ovarian cancer, head and neck cancers, and Small Cell Lung Cancer (SCLC). In another embodiment, the tumors are lymphatic tumors. In one embodiment, the tumors are hematologic tumors.

In another embodiment, the tumors arise from non-Hodgkin's lymphoma, leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), or hairy cell leukemia. In another embodiment, the autoimmune disorders are rheumatoid diseases, arthritic diseases, or rheumatoid and arthritic diseases. In a further embodiment, the disease or disorder is rheumatoid arthritis. In another embodiment, the degenerative disease is a neurodegenerative disease. In a further embodiment, the neurodegenerative disease is multiple sclerosis.

In one embodiment, the second agent is a chemotherapeutic, radiotherapeutic, or biological agent. In one embodiment, the second agent is selected from the group consisting of Duvelisib, Ibrutinib, Navitoclax, and Venetoclax, In another embodiment, the second agent is an apoptotic agent. In one embodiment, the apoptotic second agent is selected from the group consisting of Bortezomib, Azacitidine, Dasatinib, and Gefitinib. In a particular embodiment, the pharmaceutical compositions disclosed herein are administered to a patient by intravenous or subcutaneous administration. In other embodiments, the disclosed pharmaceutical compositions are administered to a patient byoral, parenteral, intramuscular, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal administration.

In one embodiment, the GITR receptor agonist protein is administered as a single bolus. In another embodiment, GITR receptor agonist protein may be administered over several divided doses. The GITR receptor agonist protein can be administered at about 0.1-100 mg/kg. In one embodiment, the GITR receptor agonist protein can be administered at a dosage selected from the group consisting of: about 0.1-0.5, 0.1-1, 0.1-10, 0.1-20, 0.1-50, 0.1-75, 1-10, 1-15, 1-7.5, 1.25-15, 1.25-7.5, 2.5-7.5, 2.5-15, 5-15, 5-7.5, 1-20, 1-50, 7-75, 1-100, 5-10, 5-15, 5-20, 5-25, 5-50, 5-75, 10-20, 10-50, 10-75, and 10-100 mg/kg. In other embodiments, the GITR receptor agonist protein is present in pharmaceutical compositions at about 0.1-100 mg/ml. In one embodiment, the GITR receptor agonist protein is present in pharmaceutical compositions at an amount selected from the group consisting of: about 0.1-0.5, 0.1-1, 0.1-10, 0.1-20, 0.1-50, 0.1-75, 1-10, 1-20, 1-50, 1-75, 1-100, 5-10, 5-15, 5-20, 5-25, 5-50, 5-75, 10-20, 10-50, 10-75, or 10-100 mg/ml. In other embodiments, a therapeutically effective amount of GITR receptor agonist protein is administered to a subject. In another embodiment, a prophylactically effective amount of GITR receptor agonist protein is administered to a subject.

The term "GITRL-associated disease or disorder" as used herein is any disease or disorder which may be ameliorated by administering an effective amount of an GITR receptor agonist to a subject in need thereof. At least one GITR receptor agonist protein, respective nucleic acid encoding therefore, or transformed or transfected cell, all as described herein may be used in therapy, e.g., in the prophylaxis and/or treatment of disorders caused by, associated with and/or accompanied by dysfunction of GITRL, particularly proliferative disorders, such as tumors, e.g. solid or lymphatic tumors; infectious diseases; inflammatory diseases; metabolic diseases; autoimmune disorders, e.g. rheumatoid and/or arthritic diseases; degenerative diseases, e.g. neurodegenerative diseases such as multiple sclerosis; apoptosis-associated diseases or transplant rejections.

The term "dysfunction of GITRL" as used herein is to be understood as any function or expression of GITRL that deviates from the normal function or expression of GITRL, e.g., overexpression of the GITRL gene or protein, reduced or abolished expression of the GITRL gene or protein compared to the normal physiological expression level of GITRL, increased activity of GITRL, reduced or abolished activity of GITRL, increased binding of GITRL to any binding partners, e.g., to a receptor, particularly a GITRL receptor or another cytokine molecule, reduced or abolished binding to any binding partner, e.g. to a receptor, particularly a GITRL receptor or another cytokine molecule, compared to the normal physiological activity or binding of GITRL.

In various embodiments, a method is provided for diagnosing and/or treating a human subject suffering from a disorder which can be diagnosed and/or treated by targeting GITRL receptors comprising administering to the human subject a GITR receptor agonist protein disclosed herein such that the effect on the activity of the target, or targets, in the human subject is agonistic, one or more symptoms is alleviated, and/or treatment is achieved. The GITR receptor agonist proteins provided herein can be used to diagnose and/or treat humans suffering from primary and metastatic cancers, including carcinomas of breast, colon, rectum, lung (e.g., small cell lung cancer "SCLC" and non-small cell lung cancer "NSCLC"), oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), tumors arising from hematopoietic malignancies, acute leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), hairy cell leukemia, Hodgkin's and non-Hodgkin's lymphomas, DLBCL, follicular lymphomas, hematopoietic malignancies, Kaposi's sarcoma, malignant lymphoma, malignant histiocytosis, malignant melanoma, multiple myeloma, paraneoplastic syndrome/hypercalcemia of malignancy, or solid tumors.

A pharmaceutical composition comprising a GITR receptor agonist protein disclosed herein and a pharmaceutically acceptable carrier is provided. In some embodiments, the pharmaceutical composition comprises at least one additional therapeutic agent for treating a disorder. For example, the additional agent may be a therapeutic agent, a chemotherapeutic agent; an imaging agent, a cytotoxic agent, an angiogenesis inhibitor, a kinase inhibitor (including but not limited to a KDR and a TIE-2 inhibitor), a co-stimulation molecule modulator or an immune checkpoint inhibitor (including but not limited to anti-B7.1, anti-B7.2, anti-B7.3, anti-B7.4, anti-CD28, anti-B7RP1, CTLA4-Ig, anti-CTLA-4, anti-PD-1, anti-PD-L1, anti-PD-L2, anti-ICOS, anti-LAG-3, anti-Tim3, anti-VISTA, anti-HVEM, anti-BTLA, LIGHT fusion protein, anti-CD137, anti-CD137L, anti-OX40, anti-OX40L, anti-CD70, anti-CD27, anti-CD27L, anti-GAL9, anti-A2AR, anti-KIR, anti-IDO-1, anti-CD20), a dendritic cell/antigen-presenting cell modulator (including but not limited to anti-CD40 antibody, anti-CD40L, anti-DC-SIGN, anti-Dectin-1, anti-CD301, anti-CD303, anti-CD123, anti-CD207, anti-DNGR1, anti-CD205, anti-DCIR, anti-CD206, anti-ILT7), a modulator for Toll-like receptors (including but not limited to anti-TLR-1, anti-TLR-2, anti-TLR-3, anti-TLR-4, anti-TLR-4, anti-TLR-5, anti-TLR-6, anti-TLR-7, anti-TLR-8, anti-TLR-9), an adhesion molecule blocker (including but not limited to an anti-LFA-1 antibody, an anti-E/L selectin antibody, a small molecule inhibitor), an anti-cytokine antibody or functional fragment thereof (including but not limited to an anti-IL-18, an anti-TNF, or an anti-IL-6/cytokine receptor antibody), a bispecific redirected T cell or NK cell cytotoxicity (including but not limited to a BiTE®), a chimeric T cell receptor (CAR-T) based therapy, a T cell receptor (TCR)-based therapy, a therapeutic cancer vaccine, methotrexate, cyclosporin, rapamycin, FK506, a detectable label or reporter, a TNF antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

In an embodiment, a method of treating a cancer or in the prevention or inhibition of metastases from the tumors described herein, the GITR receptor agonist protein(s) can be used alone or in combination with one or more additional agents, e.g., a chemotherapeutic, radiotherapy, or biological agent. In some embodiments, the agent can include the following: 13-cis-Retinoic Acid; 2-CdA; 2-Chlorodeoxyadenosine; 5-Azacitidine; 5-Fluorouracil; 5-FU; 6-Mercaptopurine; 6-MP; 6-TG; 6-Thioguanine; Abraxane; Accutane®; Actinomycin-D; Adriamycin®; Adrucil®; Afinitor®; Agrylin®; Ala-Cort®; Aldesleukin; Alemtuzumab; ALIMTA; Alitretinoin; Alkaban-AQ®; Alkeran®; All-transretinoic Acid; Alpha Interferon; Altretamine; Amethopterin; Amifostine; Aminoglutethimide; Anagrelide; Anandron®; Anastrozole; Arabinosylcytosine; Ara-C Aranesp®; Aredia®; Arimidex®; Aromasin®; Arranon®; Arsenic Trioxide; Arzerra™ Asparaginase; ATRA; Avastin®; Azacitidine; BCG; BCNU; Bendamustine; Bevacizumab; Bexarotene; BEXXAR®; Bicalutamide; BiCNU; Blenoxane®; Bleomycin; Bortezomib; Busulfan; Busulfex®; C225; Calcium Leucovorin; Campath®; Camptosar®; Camptothecin-11; Capecitabine Carac™; Carboplatin; Carmustine; Carmustine Wafer; Casodex®; CC-5013; CCI-779; CCNU; CDDP; CeeNU; Cerubidine®; Cetuximab; Chlorambucil; Cisplatin; Citrovorum Factor; Cladribine; Cortisone; Cosmegen®; CPT-11; Cyclophosphamide; Cytadren®; Cytarabine; Cytarabine Liposomal; Cytosar-U®; Cytoxan®; Dacarbazine; Dacogen; Dactinomycin; Darbepoetin Alfa; Dasatinib; Daunomycin; Daunorubicin; Daunorubicin Hydrochloride; Daunorubicin Liposomal; DaunoXome®; Decadron; Decitabine; Delta-Cortef®; Deltasone®; Denileukin; Diftitox; DepoCyt™; Dexamethasone; Dexamethasone Acetate; Dexamethasone Sodium Phosphate; Dexasone; Dexrazoxane; DHAD; DIC; Diodex; Docetaxel; Doxil®; Doxorubicin; Doxorubicin Liposomal; Droxia™; DTIC; DTIC-Dome®; Duralone®; Duvelisib; Efudex®; Eligard™; Ellence™; Eloxatin™; Elspar®; Emcyt®; Epirubicin; Epoetin Alfa; Erbitux; Erlotinib; Erwinia L-asparaginase; Estramustine; Ethyol Etopophos®; Etoposide; Etoposide Phosphate; Eulexin®; Everolimus; Evista®; Exemestane; Fareston®; Faslodex®; Femara®; Filgrastim; Floxuridine; Fludara®; Fludarabine; Fluoroplex®; Fluorouracil; Fluorouracil (cream); Fluoxymesterone; Flutamide; Folinic Acid; FUDR®; Fulvestrant; Gefitinib; Gemcitabine; Gemtuzumab ozogamicin; Gemzar; Gleevec™; Gliadel® Wafer; GM-CSF; Goserelin; Granulocyte-Colony Stimulating Factor (G-CSF); Granulocyte Macrophage Colony Stimulating Factor (G-MCSF); Halotestin®; Herceptin®; Hexadrol; Hexalen®; Hexamethylmelamine; HMM; Hycamtin®; Hydrea®; Hydrocort Acetate®; Hydrocortisone; Hydrocortisone Sodium Phosphate; Hydrocortisone Sodium Succinate; Hydrocortone Phosphate; Hydroxyurea; Ibrutinib; Ibritumomab; Ibritumomab Tiuxetan; Idamycin®; Idarubicin Ifex®; Interferon-alpha; Interferon-alpha-2b (PEG Conjugate); Ifosfamide; Interleukin-11 (IL-11); Interleukin-2 (IL-2); Imatinib mesylate; Imidazole Carboxamide; Intron A®; ipilimumab, Iressa®; Irinotecan; Isotretinoin; Ixabepilone; Ixempra™; KADCYCLA®; Kidrolase (t) Lanacort®; Lapatinib; L-asparaginase; LCR; Lenalidomide; Letrozole; Leucovorin; Leukeran; Leukine™; Leuprolide; Leurocristine; Leustatin™; Lirilumab; Liposomal Ara-C; Liquid Pred®; Lomustine; L-PAM; L-Sarcolysin; Lupron®; Lupron Depot®; Matulane®; Maxidex; Mechlorethamine; Mechlorethamine Hydrochloride; Medralone®; Medrol®; Megace®; Megestrol; Megestrol Acetate; MEK inhibitors; Melphalan; Mercaptopurine; Mesna; Mesnex™; Methotrexate; Methotrexate Sodium; Methylprednisolone; Meticorten®; Mitomycin; Mitomycin-C; Mitoxantrone M-Prednisol®; MTC; MTX; Mustargen®; Mustine; Mutamycin®; Myleran®; Mylocel™; Mylotarg®; Navitoclax; Navelbine®; Nelarabine; Neosar®; Neulasta™; Neumega®; Neupogen®; Nexavar®; Nilandron®; Nilotinib; Nilutamide; Nipent®; Nitrogen Mustard Novaldex®; Nivolumab; Novantrone®; Nplate; Octreotide; Octreotide acetate; Ofatumumab; Oncospar®; Oncovin®; Ontak®; Onxal™; Oprelvekin; Orapred®; Orasone®; Oxaliplatin; Paclitaxel; Paclitaxel Protein-bound; Pamidronate; Panitumumab; Panretin®; Paraplatin®; Pazopanib; Pediapred®; PEG Interferon; Pegaspargase; Pegfilgrastim; PEG-INTRON™; PEG-L-asparaginase; PEMETREXED; Pembrolizumab; Pentostatin; Pertuzumab; Phenylalanine Mustard; Pidilizumab; Platinol®; Platinol-AQ®; Prednisolone; Prednisone; Prelone®; Procarbazine; PROCRIT®; Proleukin®; Prolifeprospan 20 with Carmustine Implant; Purinethol®; BRAF inhibitors; Raloxifene; Revlimid®; Rheumatrex®; Rituxan®; Rituximab; Roferon-A®; Romiplostim; Rubex®; Rubidomycin hydrochloride; Sandostatin®; Sandostatin LAR®; Sargramostim; Solu-Cortef®; Solu-Medrol®; Sorafenib; SPRYCEL™; STI-571; STIVAGRA™, Streptozocin; SU11248; Sunitinib; Sutent®; Tamoxifen Tarceva®; Targretin®; Tasigna®; Taxol®; Taxotere®; Temodar®; Temozolomide Temsirolimus; Teniposide; TESPA; Thalidomide; Thalomid®; TheraCys®; Thioguanine; Thioguanine Tabloid®; Thiophosphoamide; Thioplex®; Thiotepa; TICE®; Toposar®; Topotecan; Toremifene; Torisel®; Tositumomab; Trastuzumab; Treanda®; Tremelimumab; Tretinoin; Trexall™; Trisenox®; TSPA; TYKERB®; Urelumab; VCR; Vectibix™; Velban®; Velcade®; Venetoclax; VePesid®; Vesanoid®; Viadur™; Vidaza®; Vinblastine; Vinblastine Sulfate; Vincasar Pfs®; Vincristine; Vinorelbine; Vinorelbine tartrate; VLB; VM-26; Vorinostat; Votrient; VP-16; Vumon®; Xeloda®; Zanosar®; Zevalin™; Zinecard®; Zoladex®; Zoledronic acid; Zolinza; or Zometa®, and/or any other agent not specifically listed here that target similar pathways.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more than one, or all of the substances or principles to be administered, while still achieving the desired therapeutic action. This may, e.g., be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In various embodiments, pharmaceutical compositions comprising one or more GITR receptor agonist proteins, either alone or in combination with prophylactic agents, therapeutic agents, and/or pharmaceutically acceptable carriers are provided herein. In various embodiments, nonlimiting examples of the uses of the pharmaceutical compositions disclosed herein include diagnosing, detecting, and/or monitoring a disorder, preventing, treating, managing, and/or ameliorating a disorder or one or more symptoms thereof, and/or in research. The formulation of pharmaceutical compositions, either alone or in combination with prophylactic agents, therapeutic agents, and/or pharmaceutically acceptable carriers, are known to one skilled in the art (US Patent Publication No. 20090311253 A1).

As used herein, the phrase "effective amount" means an amount of GITRL agonist protein that results in a detectable improvement (e.g., at least about 5%, 10%, 15%, 20%, 25%, 30%, 35%, 40%, 45%, 50%, 55%, 60%, 65%, 70%, 75%, or more from baseline) in one or more parameters associated with a dysfunction of GITRL or with a GITRL-associated disease or disorder.

Methods of administering a therapeutic agent provided herein include, but are not limited to, oral administration, parenteral administration (e.g., intradermal, intramuscular, intraperitoneal, intravenous and subcutaneous), epidural administration, intratumoral administration, mucosal administration (e.g., intranasal and oral routes) and pulmonary administration (e.g., aerosolized compounds administered with an inhaler or nebulizer). The formulation of pharmaceutical compositions for specific routes of administration, and the materials and techniques necessary for the various methods of administration are available and known to one skilled in the art (US Patent Publication No. 20090311253 A1).

In various embodiments, dosage regimens may be adjusted to provide for an optimum desired response (e.g., a therapeutic or prophylactic response). For example, a single bolus may be administered, several divided doses may be administered over time or the dose may be proportionally reduced or increased as indicated by the exigencies of the therapeutic situation. In some embodiments, parenteral compositions are formulated in dosage unit form for ease of administration and uniformity of dosage. The term "dosage unit form" refers to physically discrete units suited as unitary dosages for the mammalian subjects to be treated; each unit containing a predetermined quantity of active compound calculated to produce the desired therapeutic effect in association with the required pharmaceutical carrier.

An exemplary, non-limiting range for a therapeutically or prophylactically effective amount of a GITR receptor agonist protein provided herein is about 0.1-100 mg/kg, (e.g., about 0.1-0.5, 0.1-1, 0.1-10, 0.1-20, 0.1-50, 0.1-75, 1-10, 1-15, 1-7.5, 1.25-15, 1.25-7.5, 2.5-7.5, 2.5-15, 5-15, 5-7.5, 1-20, 1-50, 7-75, 1-100, 5-10, 5-15, 5-20, 5-25, 5-50, 5-75, 10-20, 10-50, 10-75, or 10-100 mg/kg, or any concentration in between). In some embodiments, the GITR receptor agonist protein is present in a pharmaceutical composition at a therapeutically effective concentration, e.g., a concentration of about 0.1-100 mg/ml (e.g., about 0.1-0.5, 0.1-1, 0.1-10, 0.1-20, 0.1-50, 0.1-75, 1-10, 1-20, 1-50, 1-75, 1-100, 5-10, 5-15, 5-20, 5-25, 5-50, 5-75, 10-20, 10-50, 10-75, or 10-100 mg/ml, or any concentration in between). Note that dosage values may vary with the type and/or severity of the condition to be alleviated. It is to be further understood that for any particular subject, specific dosage regimens may be adjusted over time according to the individual need and/or the professional judgment of the person administering or supervising the administration of the compositions, and that dosage ranges set forth herein are exemplary only and are not intended to limit the scope or practice of the claimed composition.

EXAMPLES

Example 1. Manufacture of a GITR Receptor Agonist Protein 1.1 Polypeptide Structure A) Amino acids Met1-Gly20

Ig-Kappa-signal peptide, assumed signal peptidase cleavage site after amino acid Gly20.

B) Amino acids Glu21-Ser146

First soluble cytokine domain of the human GITRL ligand (GITRL, amino acid 52-177 of SEQ ID NO: 1).

C) Amino acids Gly147-Ser154 First peptide linker element of SEQ ID NO: 2.

D) Amino acids Glu155-Ser280

Second soluble cytokine domain of the human GITRL ligand (GITRL, amino acid 52-177 of SEQ ID NO: 1).

E) Amino acids Gly281-Ser288.

Second peptide linker element of SEQ ID NO: 2.

F) Amino acids Glu289-Ser414

Third soluble cytokine domain of the human GITRL ligand (GITRL, amino acid 55-133 of SEQ ID NO: 1).

G) Amino acids Gly415-Cys435

Hinge-linker element of SEQ ID NO: 16.

H) Amino acids Pro436-Lys653 ◘

Antibody Fc fragment domain of SEQ ID NO: 13.

The above GITR receptor agonist protein is shown in SEQ ID NO: 25.

The indicated linkers may be replaced by other preferred linkers, e.g. as shown in SEQ ID NOs: 3-12.

The indicated Hinge-linker element may be replaced by other preferred Hinge-linkers, e.g. as shown in SEQ ID NOs: 19-24.

It should be noted that the first and second peptide linkers do not need to be identical.

The signal peptide sequence (A) may be replaced by any other suitable, e.g. mammalian signal peptide sequence.

1.2 Gene Cassette Encoding the Polypeptide

The synthetic gene may be optimized in view of its codon usage for the expression in suitable host cells, e.g. insect cells or mammalian cells. A preferred nucleic acid sequence is shown in SEQ ID NO: 37.

Example 2. Expression and Purification 2.1 Cloning, Expression and Purification of Fusion Polypeptides The aforementioned fusion proteins are expressed recombinantly in different eukaryotic host cells employing the methods described below:

Method for Small Scale Expression of GITR Receptor Agonist Fusion Proteins:

For small scale analysis of aforementioned GITR receptor agonist fusion proteins, Hek293 cells are grown in DMEM+ GLUTAMAX® (nutritional dietary supplements, GibCo) supplemented with 10% FBS, 100 units/ml Penicillin and 100 [mu]g/ml Streptomycin and are transiently transfected with a plasmid containing an expression cassette for a fusion polypeptide and an appropriate selection marker, e.g. a functional expression cassette comprising a blasticidine, puromycin or hygromycin resistance gene. In those cases, where a plurality of polypeptide chains is necessary to achieve the final product, the expression cassettes are either combined on one plasmid or positioned on different plasmids during the transfection. Cell culture supernatant containing recombinant fusion polypeptide are harvested three days post transfection and clarified by centrifugation at 300×g followed by filtration through a 0.22 μm sterile filter.

Method for Large Scale Expression and Purification of GITR Receptor Agonist Fusion Proteins For larger scale expression of GITR receptor agonist fusion proteins, synthetic DNA cassettes encoding the aforementioned proteins are inserted into eukaryotic expression vectors comprising appropriate selection markers (e.g. a functional expression cassette comprising a blasticidin, puromycin or hygromycin resistance gene) and genetic elements suitable to enhance the number of transcriptionally active insertion sites within the host cells genome. The sequence verified expression vectors is introduced by electroporation into suspension adapted Chinese Hamster Ovary cells (CHO-S, Invitrogen). Appropriate selection pressure will be applied three days post-transfection to transfected cells. Surviving cells carrying the vector derived resistance gene(s) are recovered by subsequent cultivation under selection pressure. Upon stable growth of the selected cell pools in chemically defined medium (PowerCHO2-CD, Lonza) at 37° C. and 7% CO2 atmosphere in an orbital shaker incubator (100 rpm, 50 mm shaking throw), the individual supernatants are analyzed by ELISA-assays detecting the aforementioned proteins and the cell pools with the highest specific productivity are expanded in shake flasks prior to protein production (orbital shaker, 100 rpm, shaking throw 50 mm).

For lab-scale protein production, individual cell pools are cultured for 7-12 days in chemically defined medium (PowerCHO2-CD, Lonza) at 37° C. and 7% CO2 atmosphere in a Wave bioreactor 20/50 EHT (GE-Healthcare). The basal medium is PowerCHO2-CD supplemented with 4 mM GLUTAMAX®. Wave culture is started with a viable cell concentration of 0.3 to 0.4×10e6 cells/ml and the following settings (for a five- or ten-liter bag): shaking frequency 18 rpm, shaking ankle 7°, gas current 0.2-0.3 L/min, 7% CO2, 36.5° C. During the Wave run, the cell culture is fed twice with POWERFEED® A (cell culture media, Lonza), usually on day 2 (20% feed) and day 5 (30% feed). After the second feed, shaking frequency is increased to 22 rpm, as well as the shaking ankle to 8°.

The bioreactor is usually harvested in between day 7 to day 12 when the cell viability drops below 80%. First, the culture supernatant is clarified using a manual depth filtration system (Millipore MILLISTAK® Pod, filter, MC0HC 0.054 $m^2$). For Strep-tagged proteins, Avidin is added to a final concentration of 0.5 mg/L. Finally, the culture supernatant containing the GITR receptor agonist fusion protein is sterile filtered using a bottle top filter (0.22 μm, PES, Corning) and stored at 2-8° C. until further processing. For affinity purification Streptactin SEPHAROSE® (high molecular weight substance for separation by gel filtration of macromolecules) is packed to a column (gel bed 2 ml), equilibrated with 15 ml buffer W (100 mM Tris-HCl, 150 mM NaCl, pH 8.0) or PBS pH 7.4 and the cell culture supernatant is applied to the column with a flow rate of approx. 4 ml/min. Subsequently, the column is washed with 15 ml buffer W and bound polypeptide is eluted stepwise by addition of 7×1 ml buffer E (100 mM Tris HCl, 150 mM NaCl, 2.5 mM Desthiobiotin, pH 8.0). Alternately, PBS pH 7.4 containing 2.5 mM Desthiobiotin can be used for this step.

Alternately to the Streptactin SEPHAROSE®-based method, the affinity purification is performed employing a column with immobilized Protein-A as affinity ligand and an Akta chromatography system (GE-Healthcare). A solid phase material with high affinity for the FC-domain of the fusion protein is chosen: MABSELECT SURE® (packing media for chromatograph, GE Healthcare). Briefly, the clarified cell culture supernatant is loaded on a HITRAP® (packed column) MABSELECT SURE® column (CV=5 ml) equilibrated in wash-buffer-1 (20 mM Pi, 95 mM NaCl, pH7.2) not exceeding a load of 10 mg fusion protein per ml column-bed. The column is washed with ten column-volumes (10CV) of aforementioned equilibration buffer followed by four column-volumes (4CV) of wash-buffer-2 (20 mM Pi, 95 mM NaCl, pH 8.0) to deplete host-cell protein and host-cell DNA. The column is then eluted with elution buffer (20 mM Pi, 95 mM NaCl, pH 3.5) and the eluate is collected in up to ten fractions with each fraction having a volume equal to column-bed volume (5 ml). Each fraction is neutralized with an equal volume of aforementioned wash-buffer-2. The linear velocity is set to 150 cm/h and kept constant during the aforementioned affinity chromatography method.

The protein amount of the eluate fractions is quantitated and peak fractions are concentrated by ultrafiltration and further purified by size exclusion chromatography (SEC).

SEC is performed on SUPERDEX® (gel filtration material) 200 10/300 GL or HiLoad 26/60 columns using an Akta chromatography system (GE-Healthcare). The columns are equilibrated with phosphate buffered saline and the concentrated, affinity-purified polypeptide is loaded onto the SEC column with the sample volume not exceeding 2% (v/v) of the column-volume. In the case of SUPERDEX® 200 10/300 GL columns (GE Healthcare), a flow rate of 0.5 ml per minute is applied. In the case of HILOAD® (chromatography column) 26/60 SUPERDEX® 200 columns, a flow rate of 2.5 ml per minute is applied. The elution profile of the polypeptide is monitored by absorbance at 280 nm.

For determination of the apparent molecular weight of purified fusion polypeptide under native conditions a SUPERDEX® 200 column is loaded with standard proteins of known molecular weight. Based on the elution volume of the standard proteins a calibration curve is plotted and the molecular weight of purified fusion polypeptide is determined. The FC-domain comprising GITR receptor agonist fusion proteins elutes from the SUPERDEX® 200 columns with an apparent molecular weight of approx. 140-180 kDa, which would confirm the homodimerization of the mature GITR receptor agonist fusion polypeptide by the Fc domain.

Example 3: Trivalent Control Protein

To compare the relative binding between hexavalent GITR receptor agonist fusion proteins and the, homotrimeric trivalent GITR receptor agonist fusion proteins stabilized with bacteriophage RB69-FOLDON is expressed in CHO-S cells and purified as described in the former section. The sequence is shown in the table below:

| SEQ ID NO | Sequence |
|---|---|
| 38 (Trivalent control protein) | METDTLLVFVLLVWVPAGNGETAKEPCMAKFGPLPSKWQ MASSEPPCVNKVSDWKLEILQNGLYLIYGQVAPNANYND VAPFEVRLYKNKDMIQTLTNKSKIQNVGGTYELHVGDTI DLIFNSEHQVLKNNTYWGIILLANPQFISGSGSSGSSGS SGSGYIEDAPSDGKFYVRKDGAWVELPTASGPSSSSSSA WSHPQFEK |

Example 4: Determination of the In Vitro Stability of GITR Receptor Agonist Proteins by Limited Protease Digestion All GITR receptor agonist proteins to be investigated will be expressed and purified as hexavalent Fc-Fusion protein as described in Example 1. The set will include GITR receptor agonist proteins comprising the N297S mutation [according to the EU numbering system] in the CH2-domain and a hinge region that enables the formation of three disulfide bridges and additionally lack the upper hinge lysine [K223, according to the EU numbering system] which is mutated to glycine [K223G]. In a limited protease digestion assay, the aforementioned GITR receptor agonist proteins comprising the N297S mutation and the K223G mutation simultaneously in context of a three disulfide enabling hinge will be compared to GITR receptor agonist proteins comprising the N297S mutation but have the K223 wildtype present either in the context of a two disulfide or three disulfide enabling hinge region.

In addition GITR receptor agonist proteins with the second linker element (iv) reduced to 4 amino-acids and the shortened hinge element (vi) will be investigated (e.g. SEQ ID NO: 32 and 34). Both engineering strategies (N297S combined with K223G mutation in context of a three disulfide enabling hinge region) and shortage of linker elements (iv and vi) have a potential impact on the stability of the respective molecules.

The stability of different GITR agonistic proteins of the present invention can be addressed by limited protease digestion in vitro. For this analysis, the aforementioned GITR receptor agonist proteins are incubated with low concentrations of proteases (e.g. Trypsin, V8 protease) at different temperatures (e.g. 4° C., 25° C., 37° C.) for different amounts of time. Quantification of specific proteolytic fragments and their appearance over time can be subsequently measured by different methods, like SDS-PAGE, analytical SEC or analytical Mass-Spectrometry methods known in the art (e.g Nano-RP-HPLC-ESI-MSMS). As the investigated proteins have most of their sequences in common, the faster appearance and enlarged quantities of specific proteolytic fragments from individual proteins over time can then be used to judge their relative stability and rank them to each other. With regard to protease-based decoy kinetics of the aforementioned GITR receptor agonist proteins investigated, the following order regarding their proteolytic stability is to be expected:

The GITR receptor agonist proteins comprising the N297S and the K223G and the three disulfide enabling hinge region simultaneously have a prolonged stability as compared to the GITR receptor agonist proteins comprising the N297S and wildtype K223 in the hinge region. The GITR receptor agonist proteins comprising the SEQ ID NO: 21 as hinge linker have a prolonged stability as compared to GITR receptor agonist proteins comprising the SEQ ID NO: 16 as hinge linker element.

Example 5: Stability/Aggregation Test

The contents of monomers and aggregates are determined by analytical SEC as described in Example 2. For this particular purpose the analysis is performed in buffers containing physiological salt concentrations at physiological pH (e.g. 0.9% NaCl, pH 7.4; PBS pH 7.4). A typical aggregation analysis is done on a SUPERDEX® 200 column (GE Healthcare). This column separates proteins in the range between 10 to 800 kDa.

For determination of the apparent molecular weight of purified fusion polypeptide under native conditions a SUPERDEX® 200 column is loaded with standard proteins of known molecular weight. Based on the elution volume of the standard proteins a calibration curve is plotted and the apparent molecular weight of purified fusion proteins of unknown molecular weight is calculated based on the elution volume.

SEC analysis of soluble, non-aggregated protein typically shows a distinct single protein peak at a defined elution volume (measured at OD at 280 nm or at OD 214 nm). This elution volume corresponds to the apparent native molecular weight of the particular protein. With regard to the definition of "monomer" in the case of FC-fusion proteins, the assembly of two polypeptide-chains is driven by the FC-part of the protein and the functional unit is a protein consisting of two chains. This unit that contains two FC-linked polypeptide chains is defined as "monomer" in the case of Fc-fusion proteins regardless of being a dimerized single-chain fusion polypeptide.

If protein aggregation occurs, the SEC analysis shows additional protein peaks with lower retention volumes. Protein oligomers potentially serve as aggregation seeds and a high content of oligomers potentially leads to aggregation of the protein. Oligomers of large molecular weight and aggregates elute in the void volume of the Superdex200 column and cannot be analyzed by SEC with respect to their native molecular weight.

Purified preparations of GITR receptor agonist fusion proteins should preferably contain only defined monomeric protein and only a very low amount of oligomeric protein. The degree of aggregation/oligomerization of a particular GITR receptor agonist fusion protein preparation is determined on basis of the SEC analysis by calculating the peak areas of the OD280 diagram for the defined monomer and the oligomer/aggregate fraction, respectively. Based on the total peak area the percentage of defined monomer protein is calculated as follows:

monomer content [%]=[Peak area monomer protein]/[Total peak area]×100)

Example 6: Determination of the Equilibrium Binding Constants for Tri- and Hexavalent GITR Receptor Ligand Constructs by QCM Analysis The equilibrium binding constants ($K_D$) of trivalent and hexavalent constructs of GITR receptor ligand are calculated based on kinetic binding data ($k_{on}$ and $k_{off}$) that are determined with an automated biosensor system (Attana A100). The A100 allows to investigate molecular interactions in real-time based on the Quartz Crystal Microbalance (QCM) technique.

For this purpose, the human GITR receptor is immobilized to the surface of a carboxyl-activated QCM-chip. Subsequently the tri- or hexavalent GITR receptor ligand, respectively, is used as an analyte at different concentrations (e.g. 0.5, 1, 2, 5, and 10 μg/ml) for analyzing the kinetic binding data for ligand-receptor binding ($k_{on}$) and dissociation ($k_{off}$). The analysis is done in real time and the respective $K_D$ can be calculated: $K_D=k_{off}/k_{on}$.

The QCM analysis shows that the trivalent GITR receptor ligand binds to the respective immobilized GITR receptor with a $K_D$ in the low nM-range with an expected $K_D$ of 1–500 nM. However, hexavalent constructs of GITR receptor ligand show a higher binding affinity in the pM-range towards the respective immobilized GITR receptor with an expected $K_D$ of 1 pM-500 nM. A common characteristic of the kinetic binding data ($k_{on}$ and $k_{off}$) is that the hexavalent constructs show faster $k_{on}$ in comparison to the trivalent constructs. In addition slower dissociation ($k_{off}$) is commonly observed for the hexavalent ligands if compared to the trivalent ligand.

Example 7: T Cell Proliferation Assay

To assess the T cell activation capability of the GITR receptor agonist, T cells are purified from human buffy coat preparations by negative selection using magnetic beads. Cells are labeled with CFSE and incubated with or without varying amounts of the GITR receptor agonist and combined with an anti-human CD3 antibody for 2-5 days at 37° C. Data on CFSE dilution as a means to measure cell division is acquired on a flow cytometer. IFNγ production is measured by an ELISA assay using cell culture supernatants and an anti-human IFNγ antibody for capture.

One expects to observe a clear augmentation of IFNγ secretion by both CD4+ and CD8+ T cells when the GITR receptor agonist is present in the T cell cultures along with the anti-human CD3 antibody. As well as higher IFNγ production one expects to see more T cells to be driven into cell cycle by measuring CFSE dilution using flow cytometry. This would demonstrate a co-stimulatory effect of the GITR receptor agonist in the context of T cell activation.

Example 8: GITR Agonist Binding Assay

Primary, human T cells are isolated from fresh buffy coat preparations using negative selection and magnetic beads. Cells are seeded into 24-well plates at 2×10e6 cells per well. T cells are incubated with an anti-human CD3 antibody (clone HIT3a, 1 μg/ml), anti-human CD28 antibody (clone CD28.2, 5 μg/ml) and varying amounts of Protein A (GITRL, 10-1000 ng/ml) or simply left in medium as control. After 3 days at 37° C. cells are fluorescently labeled with anti-human GITR and anti-human CD4 or anti-human CD8 antibodies. GITR fluorescence is assessed on a guava easyCyte flow cytometer within CD4+ and CD8+ T cell populations.

When comparing T cell populations incubated with anti-CD3 and anti-CD28 antibodies to control cells left in medium alone, one expects to observe a lower flourescent signal for GITR indicating an activation-induced downregulation of the receptor. This effect can be stronger and dose-dependent, when cells are co-incubated with the GITR agonist (Protein A), which indicates a supplementary effect caused by the GITR agonist (Protein A). Such results would suggest a binding of the GITR agonist (Protein A) to its receptor in vitro.

Example 9: Human In Vitro T Cell Proliferation Assay

Total T cells (human) purified by negative selection and magnetic beads (pan T cell isolation kit, Miltenyi Biotec) from the peripheral blood of healthy donors and stained with CFSE (CellTrace™ CFSE Cell Proliferation Kit, for flow cytometry, ThermoFisher) and seeded into 24-well plates at 2×10e6 cells per well. Cells were incubated at 37° C. for 5 days with media alone, soluble anti-CD3 antibody (clone OKT3 at 1 μg/ml) alone, anti-CD3 antibody plus anti-CD28 antibody (clone 28.2 at 1 μg/ml) or anti-CD3 antibody plus Protein A at 10, 100 or 1000 ng/ml, respectively.

On day 5, cells were washed and stained with DAPI (to exclude dead cells) and specific antibodies. Expression of Forward Scatter (FSC or size) and CFSE dilution (a measurement of proliferation) was measured by flow cytometry with a Guava EasyCyte 12 Flow Cytometer (EMD Millipore). Data analysis was performed on a minimum of ten thousand recorded events per sample with FlowJo 10.1 software (FlowJo, LLC). The percentage of responding cells was determined by gating on Forward Scatter and CFSE using the media control to determine proper gate location. Cells that had either increased cell size or decreased CFSE levels were labeled as responding cells. The individual data from two biological replicates from one donor is shown in the table below. These results are consistent with results from additional donors and clearly shows that treatment of human T cells in vitro with Protein A enhances T cell activation and proliferation as compared to antibody stimulation alone.

Quantification of Enhanced Human T Cell Activation:

Human T cell activation following treatment with PROTEIN A in vitro

| Stimulation | % of cells responding Sample 1 | Sample 2 |
|---|---|---|
| Media | 3 | 3 |
| anti-CD3 | 56 | 62 |
| anti-CD3/28 | 87 | 85 |
| anti-CD3 + Protein A 10 ng/ml | 65 | 62 |
| anti-CD3 + Protein A 100 ng/ml | 66 | 65 |
| anti-CD3 + Protein A 1000 ng/ml | 65 | 63 |

Example 10: Receptor Binding Assay

For ELISA assays assessing functional binding of OX40L to its corresponding receptor, coating of microtiter plates was performed with 1 μg/ml OX40-Fc (Bio-Techne GmbH, Wiesbaden-Nordenstadt, Germany). After blocking with StartingBlock (Life Technologies GmbH, Darmstadt, Germany), wells were incubated with indicated concentrations of GITRL compound of different configuration (Protein A, Protein B and Protein C). GITRL bound to its corresponding receptor was detected via its Strep Tag II employing the anti-StrepTag-peroxidase StrepTactin-HRP (1:5000, IBA GmbH, Goettingen, Germany) and subsequent detection of the converted Peroxidase-substrate TMB one (Kem-En-Tec Diagnostics, Taastrup, Denmark) at a wavelength of 450 nm in an ELISA reader. FIG. 6 clearly demonstrates functional binding of all tested protein configurations of the invention. Binding capacity of N- and C-terminal shortened variants is comparable to Protein A.

The invention claimed is:

1. A glucocorticoid-induced tumor necrosis factor receptor (GITR) receptor agonist protein comprising a single-chain fusion polypeptide comprising:

(i) a first soluble GITRL (GITR ligand) domain, (ii) a first peptide linker, (iii) a second soluble GITRL domain, (iv) a second peptide linker, (v) a third soluble GITRL domain, (vi) a hinge-linker selected from the group consisting SEQ ID NOs: 16 and 19-24, and (vii) an antibody Fc fragment, wherein the antibody Fc fragment (vii) consists of the amino acid sequence of SEQ ID NO: 14 or amino acids 1-217 of SEQ ID NO: 14.

2. The GITR receptor agonist protein of claim 1, wherein the antibody Fc fragment (vii) is fused to the C-terminal end of the third GITRL domain (v) via a hinge-linker (vi).

3. The GITR receptor agonist protein of claim 1, which is substantially non-aggregating.

4. The GITR receptor agonist protein of claim 1, wherein the second and/or third soluble GITRL domain is an N-terminally shortened domain which optionally comprises only one amino acid mutation.

5. The GITR receptor agonist protein of claim 1, wherein at least one of the soluble GITRL domains is a soluble GITRL domain with an N-terminal sequence which starts with amino acid E52 or A54 or K55 or E56 or P57 of human GITRL according to SEQ ID NO: 1 and wherein E52 or A54 or K55 or E56 is optionally replaced by a neutral amino acid.

6. The GITR receptor agonist protein of claim 5, wherein at least one of the soluble GITRL domains is a soluble GITRL domain with an N-terminal sequence selected from the group consisting of: (a) E52-P57 and (b) (Gly/Ser)56-P57.

7. The GITR receptor agonist protein of claim 5, wherein the soluble GITRL domain ends with amino acid 5177 of SEQ ID NO: 1 and/or optionally comprises one or two mutations at position E52, A54, K55, L65A, P66A, K68A, P77, N80, V82, E88, L90, Q91, N106, N120, N129, K121, D122, V144, L159, N161, N172, P173, Q174.

8. The GITR receptor agonist protein of claim 5, wherein at least the soluble GITRL domain (iii), is a C-terminal-shortened GITRL domain ending with A170, P171 or Q174 according to SEQ ID NO: 1.

9. The GITR receptor agonist protein of claim 6, wherein the soluble GITRL domains (i), (iii) and (v) consist of amino acids E52-S177 of human GITRL according to SEQ ID NO: 1.

10. The GITR receptor agonist protein of claim 1, wherein the first and second peptide linkers (ii) and (iv) independently have a length of 3-8 amino acids.

11. The GITR receptor agonist protein of claim 10, wherein the first and the second peptide linkers (ii) and (iv) consist of the amino acid sequence according to SEQ ID NO: 2.

12. The GITR receptor agonist protein of claim 1, which additionally comprises an N terminal signal peptide domain.

13. The GITR receptor agonist protein of claim 1, comprising the amino acid sequence of SEQ ID NO: 26 or 29.

14. The GITR receptor agonist protein of claim 1, comprising two polypeptides each having the amino acid sequence as set forth in SEQ ID NO: 29, wherein the two polypeptides are dimerized via disulfide bridges of the hinge linker.

15. The GITR receptor agonist protein of claim 14, wherein the two polypeptides are covalently linked through three interchain disulfide bonds formed at positions 406, 412, and 415 of SEQ ID NO: 29.

16. The GITR receptor agonist protein of claim 1, wherein the polypeptide is further post-translationally modified.

17. The GITR receptor agonist protein of claim 16, wherein the post-translational modification comprises modification of the N-terminal glutamine to pyroglutamate.

18. A nucleic acid molecule encoding the GITR receptor agonist protein of claim 1, in operative linkage with an expression control sequence.

19. An expression vector comprising the nucleic acid molecule of claim 18.

20. A cell or a non-human organism transformed or transfected with a nucleic acid molecule of claim 18.

21. A pharmaceutical or diagnostic composition comprising as an active agent of the GITR receptor agonist protein of claim 1, and one or more pharmaceutically acceptable carriers, diluents, excipients and/or adjuvants.

* * * * *